(12) United States Patent
Dumbauld et al.

(10) Patent No.: US 8,668,689 B2
(45) Date of Patent: Mar. 11, 2014

(54) IN-LINE VESSEL SEALER AND DIVIDER

(75) Inventors: Patrick L. Dumbauld, Lyons, CO (US); David M. Garrison, Longmont, CO (US); Paul Guerra, Boulder, CO (US); Dylan Hushka, Boulder, CO (US)

(73) Assignee: Covidien AG (CH)

(*) Notice: Subject to any disclaimer, the term of this patent is extended or adjusted under 35 U.S.C. 154(b) by 960 days.

(21) Appl. No.: 12/762,482

(22) Filed: Apr. 19, 2010

(65) Prior Publication Data
US 2010/0204697 A1    Aug. 12, 2010

Related U.S. Application Data

(60) Division of application No. 11/594,396, filed on Nov. 8, 2006, now Pat. No. 7,722,607, which is a continuation-in-part of application No. 11/540,335, filed on Sep. 29, 2006, now Pat. No. 7,789,878.

(60) Provisional application No. 60/722,177, filed on Sep. 30, 2005.

(51) Int. Cl.
*A61B 18/14*    (2006.01)
(52) U.S. Cl.
USPC ............................................. 606/51; 606/52
(58) Field of Classification Search
USPC ................................................ 606/41, 45–52
See application file for complete search history.

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| CA | 2104423 | 2/1994 |
| DE | 2415263 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Michael Peffley

(57) ABSTRACT

An endoscopic forceps includes a housing having a shaft attached thereto, the shaft including a pair of jaw members disposed at a distal end thereof. The forceps also includes a drive assembly disposed in the housing which moves the jaw members relative to one another from a first position wherein the jaw members are disposed in spaced relation relative to one another to a second position wherein the jaw members are closer to one another for manipulating tissue. A pair of handles is operatively connected to the drive assembly and the handles are movable relative to the housing to actuate the drive assembly to move the jaw members. Each of the jaw members is adapted to connect to a source of electrical energy such that the jaw members are capable of conducting energy for treating tissue. The forceps also includes a first switch disposed on the housing which is activatable to selectively deliver energy of a first electrical potential to at least one jaw member for treating tissue in a monopolar fashion. A second switch is disposed on the housing and is activatable to selectively deliver energy of a first electrical potential to one jaw member and selectively deliver energy of a second electrical potential to the other jaw member for treating tissue in a bipolar fashion.

7 Claims, 31 Drawing Sheets

(56) References Cited

U.S. PATENT DOCUMENTS

| | | | |
|---|---|---|---|
| 728,883 | A | 5/1903 | Downes |
| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 2,002,594 | A | 5/1935 | Wappler et al. |
| 2,011,169 | A | 8/1935 | Wappler |
| 2,031,682 | A | 2/1936 | Wappler et al. |
| 2,054,149 | A | 9/1936 | Wappler |
| 2,176,479 | A | 10/1939 | Willis |
| 2,305,156 | A | 4/1941 | Grubel |
| 2,279,753 | A | 4/1942 | Knopp |
| 2,327,353 | A | 8/1943 | Karle |
| 2,632,661 | A | 8/1948 | Cristofv |
| 2,668,538 | A | 2/1954 | Baker |
| 2,796,065 | A | 6/1957 | Kapp |
| 3,073,311 | A | 1/1963 | Tibbs et al. |
| 3,100,489 | A | 8/1963 | Bagley |
| 3,372,288 | A | 3/1968 | Wigington |
| 3,459,187 | A | 8/1969 | Pallotta |
| 3,643,663 | A | 2/1972 | Sutter |
| 3,648,001 | A | 3/1972 | Anderson et al. |
| 3,651,811 | A | 3/1972 | Hildebrandt et al. |
| 3,678,229 | A | 7/1972 | Osika |
| 3,720,896 | A | 3/1973 | Beierlein |
| 3,763,726 | A | 10/1973 | Hildebrand |
| 3,779,918 | A | 12/1973 | Ikeda et al. |
| 3,801,766 | A | 4/1974 | Morrison, Jr. |
| 3,862,630 | A | 1/1975 | Balamuth |
| 3,863,339 | A | 2/1975 | Reaney et al. |
| 3,866,610 | A | 2/1975 | Kletschka |
| 3,875,945 | A | 4/1975 | Friedman |
| 3,897,786 | A | 8/1975 | Garnett et al. |
| 3,911,766 | A | 10/1975 | Fridolph et al. |
| 3,920,021 | A | 11/1975 | Hiltebrandt |
| 3,921,641 | A | 11/1975 | Hulka |
| 3,938,527 | A * | 2/1976 | Rioux et al. ................. 606/42 |
| 3,952,749 | A | 4/1976 | Fridolph et al. |
| 3,970,088 | A | 7/1976 | Morrison |
| 3,987,795 | A | 10/1976 | Morrison |
| 4,005,714 | A | 2/1977 | Hiltebrandt |
| 4,016,881 | A | 4/1977 | Rioux et al. |
| 4,041,952 | A | 8/1977 | Morrison, Jr. et al. |
| 4,043,342 | A | 8/1977 | Morrison, Jr. |
| 4,074,718 | A | 2/1978 | Morrison, Jr. |
| 4,076,028 | A | 2/1978 | Simmons |
| 4,080,820 | A | 3/1978 | Allen |
| 4,088,134 | A | 5/1978 | Mazzariello |
| 4,112,950 | A | 9/1978 | Pike |
| 4,127,222 | A | 11/1978 | Adams |
| 4,128,099 | A | 12/1978 | Bauer |
| 4,165,746 | A | 8/1979 | Burgin |
| 4,187,420 | A | 2/1980 | Piber |
| 4,200,104 | A | 4/1980 | Harris |
| 4,233,734 | A | 11/1980 | Bies |
| 4,236,470 | A | 12/1980 | Stenson |
| 4,274,413 | A | 6/1981 | Hahn et al. |
| 4,300,564 | A | 11/1981 | Furihata |
| 4,311,145 | A | 1/1982 | Esty et al. |
| D263,020 | S | 2/1982 | Rau, III |
| 4,370,980 | A | 2/1983 | Lottick |
| 4,375,218 | A | 3/1983 | DiGeronimo |
| 4,416,276 | A | 11/1983 | Newton et al. |
| 4,418,692 | A | 12/1983 | Guay |
| 4,443,935 | A | 4/1984 | Zamba et al. |
| 4,452,246 | A | 6/1984 | Bader et al. |
| 4,470,786 | A | 9/1984 | Sano et al. |
| 4,492,231 | A | 1/1985 | Auth |
| 4,493,320 | A | 1/1985 | Treat |
| 4,503,855 | A | 3/1985 | Maslanka |
| 4,506,669 | A | 3/1985 | Blake, III |
| 4,509,518 | A | 4/1985 | McGarry et al. |
| 4,513,271 | A | 4/1985 | Reisem |
| 4,552,143 | A | 11/1985 | Lottick |
| 4,574,804 | A | 3/1986 | Kurwa |
| 4,597,379 | A | 7/1986 | Kihn et al. |
| 4,600,007 | A | 7/1986 | Lahodny et al. |
| 4,619,258 | A | 10/1986 | Pool |
| 4,624,254 | A | 11/1986 | McGarry et al. |
| 4,644,950 | A | 2/1987 | Valli |
| 4,655,215 | A | 4/1987 | Pike |
| 4,655,216 | A | 4/1987 | Tischer |
| 4,657,016 | A | 4/1987 | Garito et al. |
| 4,662,372 | A | 5/1987 | Sharkany et al. |
| 4,671,274 | A | 6/1987 | Sorochenko |
| 4,674,499 | A | 6/1987 | Pao |
| 4,685,459 | A | 8/1987 | Xoch et al. |
| 4,733,662 | A | 3/1988 | DeSatnick et al. |
| D295,893 | S | 5/1988 | Sharkany et al. |
| D295,894 | S | 5/1988 | Sharkany et al. |
| 4,754,892 | A | 7/1988 | Retief |
| 4,763,669 | A | 8/1988 | Jaeger |
| 4,805,616 | A | 2/1989 | Pao |
| 4,827,929 | A | 5/1989 | Hodge |
| 4,829,313 | A | 5/1989 | Taggart |
| 4,846,171 | A | 7/1989 | Kauphusman et al. |
| 4,887,612 | A | 12/1989 | Esser et al. |
| 4,938,761 | A | 7/1990 | Ensslin |
| 4,947,009 | A | 8/1990 | Osika et al. |
| 4,985,030 | A | 1/1991 | Melzer et al. |
| 5,007,908 | A | 4/1991 | Rydell |
| 5,026,370 | A | 6/1991 | Lottick |
| 5,026,371 | A | 6/1991 | Rydell et al. |
| 5,035,695 | A | 7/1991 | Weber, Jr. et al. |
| 5,037,433 | A | 8/1991 | Wilk et al. |
| 5,042,707 | A | 8/1991 | Taheri |
| 5,047,046 | A | 9/1991 | Bodoia |
| 5,078,716 | A | 1/1992 | Doll |
| 5,084,057 | A | 1/1992 | Green et al. |
| 5,085,659 | A | 2/1992 | Rydell |
| 5,099,840 | A | 3/1992 | Goble et al. |
| 5,100,430 | A | 3/1992 | Avellanet et al. |
| 5,108,392 | A | 4/1992 | Spingler |
| 5,112,343 | A | 5/1992 | Thornton |
| 5,116,332 | A | 5/1992 | Lottick |
| 5,122,139 | A | 6/1992 | Sutter |
| 5,147,357 | A | 9/1992 | Rose et al. |
| 5,151,102 | A | 9/1992 | Kamiyama et al. |
| 5,151,978 | A | 9/1992 | Bronikowski et al. |
| 5,176,695 | A | 1/1993 | Dulebohn |
| 5,190,541 | A | 3/1993 | Abele et al. |
| 5,196,009 | A | 3/1993 | Kirwan, Jr. |
| 5,197,964 | A | 3/1993 | Parins |
| 5,209,747 | A | 5/1993 | Knoepfler |
| 5,211,655 | A | 5/1993 | Hasson |
| 5,215,101 | A | 6/1993 | Jacobs et al. |
| 5,217,457 | A | 6/1993 | Delahuerga et al. |
| 5,217,458 | A | 6/1993 | Parins |
| 5,217,460 | A | 6/1993 | Knoepfler |
| 5,219,354 | A | 6/1993 | Choudhury et al. |
| 5,244,462 | A | 9/1993 | Delahuerga et al. |
| 5,250,047 | A | 10/1993 | Rydell |
| 5,250,063 | A | 10/1993 | Abidin et al. |
| 5,258,001 | A | 11/1993 | Corman |
| 5,258,006 | A | 11/1993 | Rydell et al. |
| 5,261,918 | A | 11/1993 | Phillips et al. |
| 5,275,615 | A | 1/1994 | Rose |
| 5,277,201 | A | 1/1994 | Stern |
| 5,282,799 | A | 2/1994 | Rydell |
| 5,282,800 | A | 2/1994 | Foshee et al. |
| 5,282,826 | A | 2/1994 | Quadri |
| 5,290,286 | A | 3/1994 | Parins |
| 5,300,082 | A | 4/1994 | Sharpe et al. |
| 5,304,203 | A | 4/1994 | El-Mallawany et al. |
| 5,308,353 | A | 5/1994 | Beurrier |
| 5,308,357 | A | 5/1994 | Lichtman |
| 5,313,027 | A | 5/1994 | Inoue et al. |
| 5,314,445 | A | 5/1994 | Degwitz et al. |
| 5,318,589 | A | 6/1994 | Lichtman |
| 5,324,289 | A | 6/1994 | Eggers |
| D348,930 | S | 7/1994 | Olson |
| 5,326,806 | A | 7/1994 | Yokoshima et al. |
| 5,330,471 | A | 7/1994 | Eggers |
| 5,330,502 | A | 7/1994 | Hassler et al. |

(56) References Cited

U.S. PATENT DOCUMENTS

| | | |
|---|---|---|
| D349,341 S | 8/1994 | Lichtman et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,359,993 A | 11/1994 | Slater et al. |
| 5,366,477 A | 11/1994 | LeMarie, III et al. |
| 5,367,250 A | 11/1994 | Whisenand |
| 5,368,600 A | 11/1994 | Failla et al. |
| 5,374,277 A | 12/1994 | Hassler |
| 5,376,089 A | 12/1994 | Smith |
| 5,376,094 A | 12/1994 | Kline |
| D354,564 S | 1/1995 | Medema |
| 5,383,875 A | 1/1995 | Bays et al. |
| 5,383,880 A | 1/1995 | Hooven |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,395,360 A | 3/1995 | Manoukian |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,417,709 A | 5/1995 | Slater |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,809 A | 10/1995 | Janssen |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,512,721 A | 4/1996 | Young et al. |
| 5,514,134 A | 5/1996 | Rydell et al. |
| 5,520,702 A | 5/1996 | Sauer et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsukagoshi et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,599,350 A | 2/1997 | Schulze et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,607,436 A | 3/1997 | Pratt et al. |
| 5,609,573 A * | 3/1997 | Sandock .................... 604/22 |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A * | 11/1997 | Yates et al. .................... 606/51 |
| 5,690,652 A | 11/1997 | Wurster |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |

(56) References Cited

U.S. PATENT DOCUMENTS

| | | |
|---|---|---|
| 5,702,390 A | 12/1997 | Austin et al. |
| 5,707,369 A | 1/1998 | Vaitekunas et al. |
| 5,709,680 A | 1/1998 | Yates et al. |
| 5,713,896 A * | 2/1998 | Nardella ............ 606/50 |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,762,255 A | 6/1998 | Chrisman et al. |
| 5,762,609 A | 6/1998 | Benaron et al. |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| 5,779,727 A | 7/1998 | Orejola |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,083 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,830,212 A | 11/1998 | Cartmell et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,938,589 A | 8/1999 | Wako et al. |
| 5,941,869 A | 8/1999 | Patterson et al. |
| 5,944,718 A | 8/1999 | Dafforn et al. |
| 5,951,545 A | 9/1999 | Schilling et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,354 A | 1/2000 | Culp et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,090,123 A | 7/2000 | Culp et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |

(56) References Cited

U.S. PATENT DOCUMENTS

| | | |
|---|---|---|
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | VanDeMoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,329,778 B1 | 12/2001 | Culp et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,361,534 B1 | 3/2002 | Chen et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| D465,281 S | 11/2002 | Lang |
| D466,209 S | 11/2002 | Bon |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,654 B2 | 9/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B2 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |

(56) References Cited

U.S. PATENT DOCUMENTS

| | | |
|---|---|---|
| 6,818,000 B2 | 11/2004 | Muller et al. |
| 6,818,007 B1 | 11/2004 | Dampney et al. |
| 6,821,285 B2 | 11/2004 | Laufer et al. |
| 6,835,200 B2 | 12/2004 | Laufer et al. |
| 6,857,357 B2 | 2/2005 | Fujii |
| D502,994 S | 3/2005 | Blake, III |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,976,492 B2 | 12/2005 | Ingle et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| 7,137,980 B2 | 11/2006 | Buysse et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 * | 1/2007 | Sartor et al. ............. 606/37 |
| 7,156,846 B2 | 1/2007 | Dycus et al. |
| 7,160,298 B2 | 1/2007 | Lawes et al. |
| 7,160,299 B2 | 1/2007 | Baily |
| 7,166,106 B2 | 1/2007 | Bartel et al. |
| 7,169,145 B2 | 1/2007 | Isaacson et al. |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,264 B2 | 5/2007 | Daniel et al. |
| 7,223,265 B2 | 5/2007 | Keppel |
| D545,432 S | 6/2007 | Watanabe |
| 7,232,440 B2 | 6/2007 | Dumbauld et al. |
| 7,238,184 B2 | 7/2007 | Megerman et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| D567,943 S | 4/2008 | Moses et al. |
| 7,354,440 B2 | 4/2008 | Truckal et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,425,835 B2 | 9/2008 | Eisele |
| 7,431,721 B2 | 10/2008 | Paton et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,503,474 B2 | 3/2009 | Hillstead et al. |
| 7,503,917 B2 * | 3/2009 | Sartor et al. ............. 606/45 |
| 7,510,556 B2 | 3/2009 | Nguyen et al. |
| 7,513,898 B2 | 4/2009 | Johnson et al. |
| 7,517,351 B2 | 4/2009 | Culp et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 7,582,087 B2 | 9/2009 | Tetzlaff et al. |
| 7,588,565 B2 | 9/2009 | Marchitto et al. |
| 7,594,916 B2 | 9/2009 | Weinberg |
| 7,597,693 B2 | 10/2009 | Garrison |
| 7,621,910 B2 | 11/2009 | Sugi |
| 7,628,791 B2 | 12/2009 | Garrison et al. |
| 7,628,792 B2 | 12/2009 | Guerra |
| 7,641,653 B2 | 1/2010 | Dalla Betta et al. |
| 7,651,493 B2 | 1/2010 | Arts et al. |
| 7,651,494 B2 | 1/2010 | McClurken et al. |

(56) References Cited

U.S. PATENT DOCUMENTS

| | | |
|---|---|---|
| 7,655,007 B2 | 2/2010 | Baily |
| 7,678,111 B2 | 3/2010 | Mulier et al. |
| 7,686,804 B2 | 3/2010 | Johnson et al. |
| 7,686,827 B2 | 3/2010 | Hushka |
| 2002/0107517 A1 | 8/2002 | Witt et al. |
| 2002/0111624 A1 | 8/2002 | Witt et al. |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0082952 A1 | 4/2004 | Dycus |
| 2004/0115296 A1 | 6/2004 | Duffin |
| 2004/0143263 A1 | 7/2004 | Schechter et al. |
| 2004/0148035 A1 | 7/2004 | Barrett et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0236326 A1 | 11/2004 | Schulze et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059858 A1 | 3/2005 | Frith et al. |
| 2005/0059934 A1 | 3/2005 | Wenchell et al. |
| 2005/0096645 A1 | 5/2005 | Wellman et al. |
| 2005/0101952 A1 | 5/2005 | Lands et al. |
| 2005/0113824 A1 * | 5/2005 | Sartor et al. ............ 606/42 |
| 2005/0113827 A1 * | 5/2005 | Dumbauld et al. ......... 606/45 |
| 2005/0149017 A1 | 7/2005 | Dycus |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0052778 A1 | 3/2006 | Chapman et al. |
| 2006/0052779 A1 | 3/2006 | Hammill |
| 2006/0064086 A1 | 3/2006 | Odom |
| 2006/0079888 A1 | 4/2006 | Mulier et al. |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0116675 A1 | 6/2006 | McClurken et al. |
| 2006/0129146 A1 | 6/2006 | Dycus et al. |
| 2006/0167452 A1 | 7/2006 | Moses et al. |
| 2006/0173452 A1 | 8/2006 | Buysse et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0173804 A1 | 7/2007 | Wham et al. |
| 2007/0173811 A1 | 7/2007 | Couture et al. |
| 2007/0173813 A1 | 7/2007 | Odom |
| 2007/0173814 A1 | 7/2007 | Hixson et al. |
| 2007/0198011 A1 | 8/2007 | Sugita |
| 2007/0208339 A1 | 9/2007 | Arts et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039831 A1 | 2/2008 | Odom et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0125767 A1 | 5/2008 | Blaha |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0036881 A1 | 2/2009 | Artale et al. |
| 2009/0036899 A1 | 2/2009 | Carlton et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0182329 A1 | 7/2009 | Dycus |
| 2009/0187188 A1 | 7/2009 | Guerra et al. |
| 2009/0198233 A1 | 8/2009 | Chojin |
| 2009/0204114 A1 | 8/2009 | Odom |
| 2009/0209957 A1 | 8/2009 | Schmaltz et al. |
| 2009/0209960 A1 | 8/2009 | Chojin |

(56) References Cited

U.S. PATENT DOCUMENTS

| | | |
|---|---|---|
| 2009/0234354 A1 | 9/2009 | Johnson et al. |
| 2009/0248021 A1 | 10/2009 | Mckenna |
| 2009/0261804 A1 | 10/2009 | Mckenna et al. |
| 2009/0306660 A1 | 12/2009 | Johnson et al. |
| 2010/0016857 A1 | 1/2010 | Mckenna et al. |
| 2010/0023009 A1 | 1/2010 | Moses et al. |
| 2010/0036375 A1 | 2/2010 | Regadas |
| 2010/0042100 A1 | 2/2010 | Tetzlaff et al. |
| 2010/0042140 A1 | 2/2010 | Cunningham |
| 2010/0042142 A1 | 2/2010 | Cunningham |
| 2010/0042143 A1 | 2/2010 | Cunningham |
| 2010/0049187 A1 | 2/2010 | Carlton et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0087818 A1 | 4/2010 | Cunningham |

FOREIGN PATENT DOCUMENTS

| | | |
|---|---|---|
| DE | 2514501 | 10/1976 |
| DE | 2627679 | 1/1977 |
| DE | 3423356 | 1/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 4/2002 |
| DE | 20 2007 009317 | 10/2007 |
| DE | 19738457 | 1/2009 |
| EP | 0364216 | 4/1990 |
| EP | 0467501 | 1/1992 |
| EP | 0509670 | 10/1992 |
| EP | 0518230 | 12/1992 |
| EP | 0541930 | 5/1993 |
| EP | 0572131 | 12/1993 |
| EP | 0584787 | 3/1994 |
| EP | 0589453 | 3/1994 |
| EP | 0589555 | 3/1994 |
| EP | 0623316 | 11/1994 |
| EP | 0624348 | 11/1994 |
| EP | 0650701 | 5/1995 |
| EP | 0694290 | 3/1996 |
| EP | 0717966 | 6/1996 |
| EP | 0754437 | 3/1997 |
| EP | 0517243 | 9/1997 |
| EP | 0853922 | 7/1998 |
| EP | 0875209 | 11/1998 |
| EP | 0878169 | 11/1998 |
| EP | 0887046 | 1/1999 |
| EP | 0923907 | 6/1999 |
| EP | 0950378 | 10/1999 |
| EP | 0986990 | 3/2000 |
| EP | 1034747 | 9/2000 |
| EP | 1034748 | 9/2000 |
| EP | 1025807 | 10/2000 |
| EP | 1034746 | 10/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1159926 | 12/2001 |
| EP | 1177771 | 2/2002 |
| EP | 1278007 | 1/2003 |
| EP | 1301135 | 4/2003 |
| EP | 1330991 | 7/2003 |
| EP | 1486177 | 6/2004 |
| EP | 1472984 | 11/2004 |
| EP | 0774232 | 1/2005 |
| EP | 1527747 | 5/2005 |
| EP | 1530952 | 5/2005 |
| EP | 1532932 | 5/2005 |
| EP | 1535581 | 6/2005 |
| EP | 1609430 | 12/2005 |
| EP | 1632192 | 3/2006 |
| EP | 1642543 | 4/2006 |
| EP | 1645238 | 4/2006 |
| EP | 1645240 | 4/2006 |
| EP | 1649821 | 4/2006 |
| EP | 1707143 | 10/2006 |
| EP | 1767163 | 3/2007 |
| EP | 1769765 | 4/2007 |
| EP | 1769766 | 4/2007 |
| EP | 1785101 | 5/2007 |
| EP | 1810625 | 7/2007 |
| EP | 1810628 | 7/2007 |
| EP | 1842500 | 10/2007 |
| EP | 1878400 | 1/2008 |
| EP | 1929970 | 6/2008 |
| EP | 1990019 | 11/2008 |
| EP | 1683496 | 12/2008 |
| EP | 1527744 | 2/2009 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 6-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/19681 | 10/1993 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 95/20360 | 8/1995 |
| WO | WO 96/05776 | 2/1996 |
| WO | WO 9605776 | 2/1996 |
| WO | WO 96/11635 | 4/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/18768 | 5/1997 |
| WO | WO 97/24073 | 7/1997 |

(56) References Cited

FOREIGN PATENT DOCUMENTS

| | | |
|---|---|---|
| WO | WO 97/24993 | 7/1997 |
| WO | WO 98/14124 | 4/1998 |
| WO | WO 98/27880 | 7/1998 |
| WO | WO 98/43264 | 10/1998 |
| WO | WO 99/03407 | 1/1999 |
| WO | WO 99/03408 | 1/1999 |
| WO | WO 99/03409 | 1/1999 |
| WO | WO 99/03414 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/01847 | 1/2001 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/028585 | 4/2004 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/009255 | 2/2005 |
| WO | WO 2005/048809 | 6/2005 |
| WO | WO 2005/050151 | 6/2005 |
| WO | WO 2005/110264 | 11/2005 |
| WO | WO 2008/045348 | 4/2008 |
| WO | WO 2008/045350 | 4/2008 |
| WO | WO 2008/112147 | 9/2008 |
| WO | WO 2009/005850 | 1/2009 |
| WO | WO 2009/039510 | 3/2009 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.

(56) References Cited

OTHER PUBLICATIONS

Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 10175559.3 dated May 15, 2012.

* cited by examiner

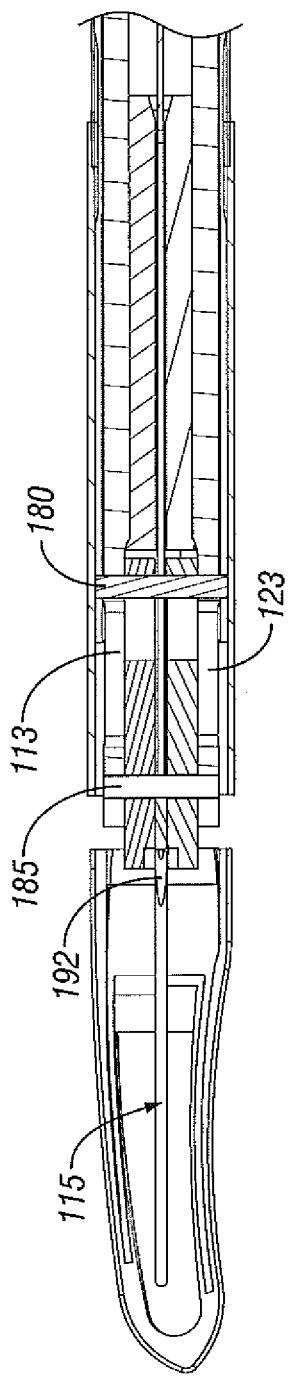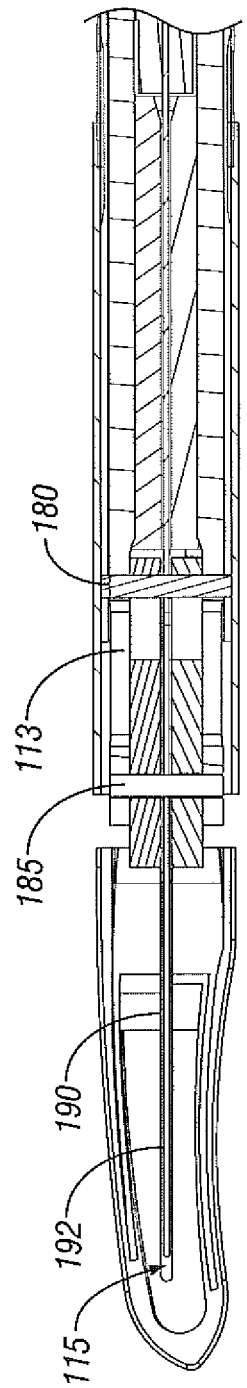
FIG. 8A
FIG. 8B

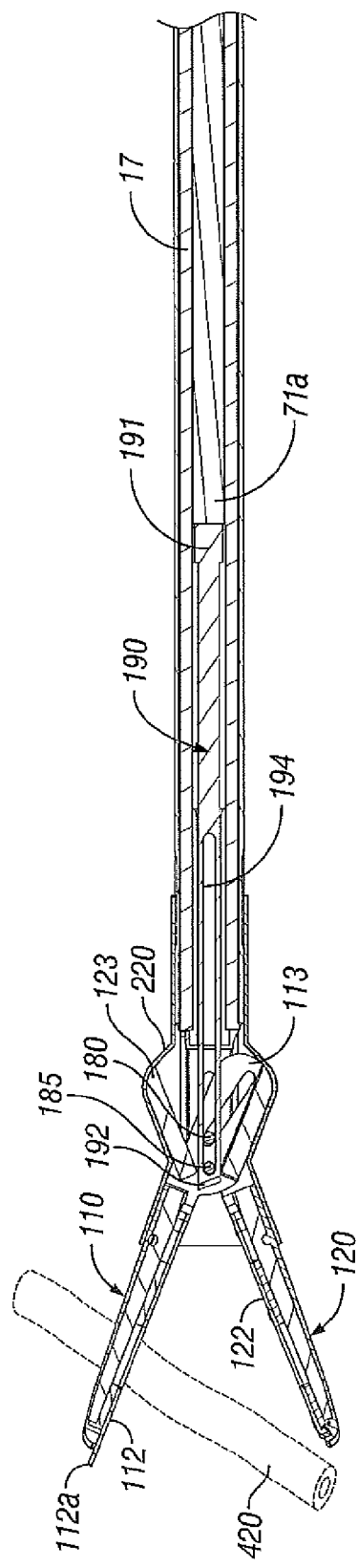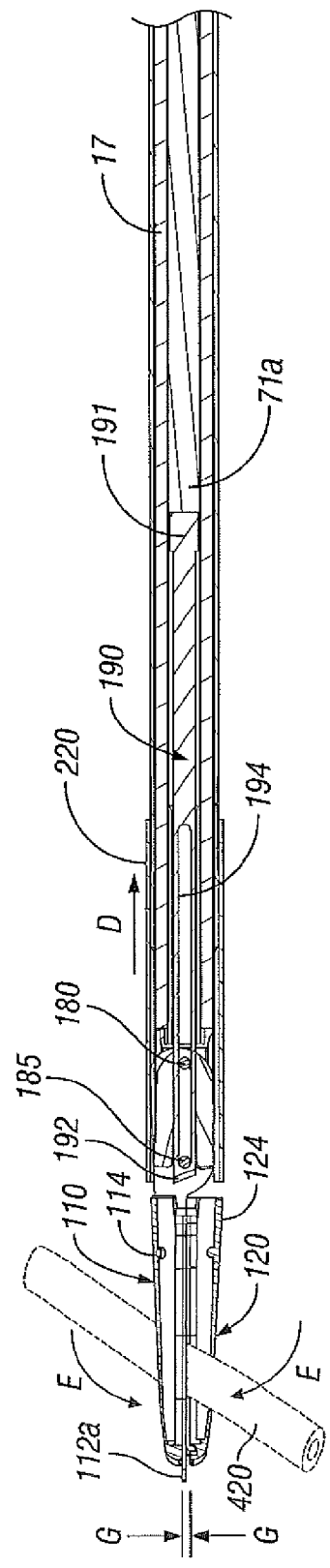
FIG. 10A
FIG. 10B

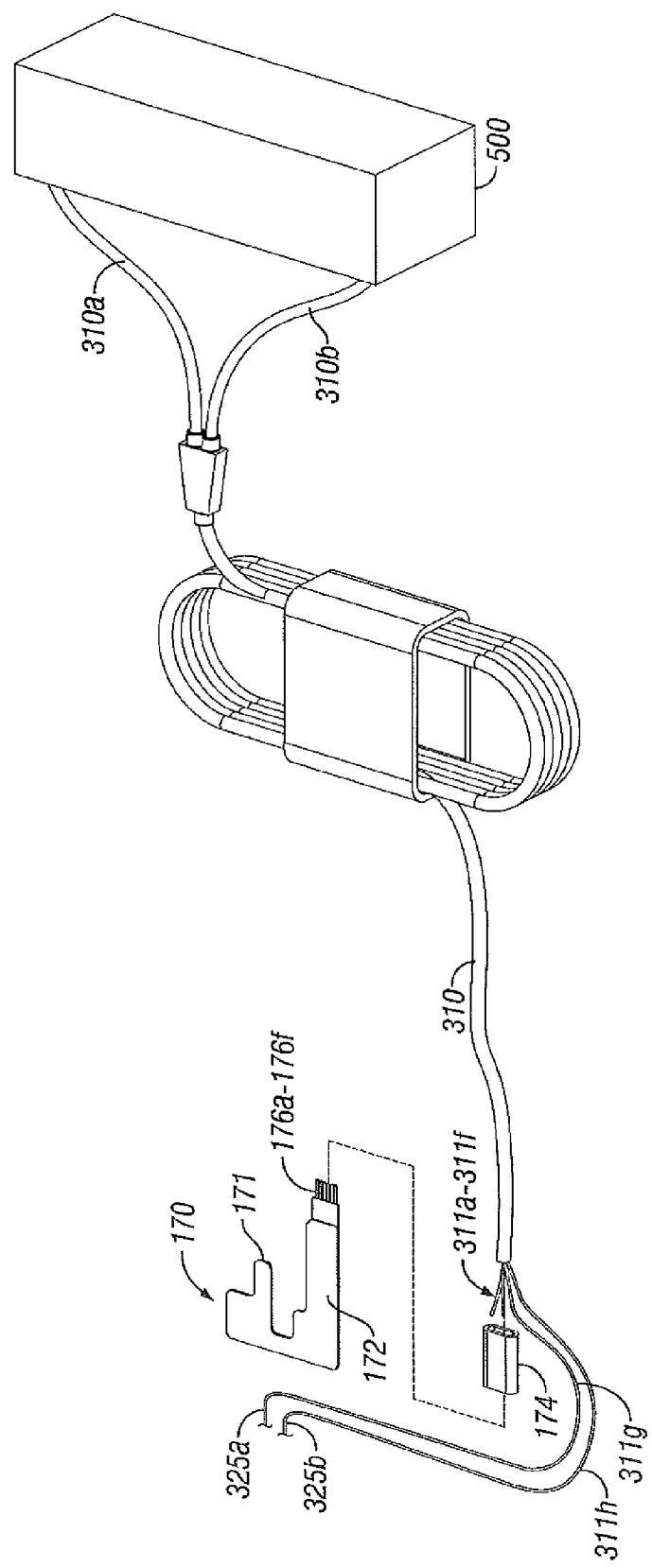

IN-LINE VESSEL SEALER AND DIVIDER

CROSS REFERENCE TO RELATED APPLICATIONS

The present application is a divisional of U.S. patent application Ser. No. 11/594,396, filed on Nov. 8, 2006, entitled "IN-LINE VESSEL SEALER AND DIVIDER" by Patrick L. Dumbauld et al., now U.S. Pat. No. 7,722, 607, which is a continuation-in-part of U.S. patent application Ser. No. 11/540,335, filed on Sep. 29, 2006, entitled "IN-LINE VESSEL SEALER AND DIVIDER" by Patrick L. Dumbauld et al., now U.S. Pat. No. 7,789, 878, which claims the benefit of and priority to U.S. Provisional Application No. 60/722,177, filed on Sep. 30, 2005, entitled "IN-LINE VESSEL SEALER AND DIVIDER" by Patrick L. Dumbauld, the entire contents of each of these applications being incorporated by reference herein.

BACKGROUND

The present disclosure relates to an electrosurgical forceps and more particularly, the present disclosure relates to an elongated endoscopic combination bipolar and monopolar electrosurgical forceps for sealing and/or cutting tissue.

Technical Field

Electrosurgical forceps utilize both mechanical clamping action and electrical energy to affect hemostasis by heating tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

In order to effectively seal larger vessels (or tissue) two predominant mechanical parameters must be accurately controlled—the pressure applied to the vessel (tissue) and the gap distance between the electrodes or tissue sealing surfaces—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical jaw gap for fusing vessel walls is optimum between 0.001 and 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

Many known instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied the tissue may pre-maturely move prior to activation and sealing and/or a thicker, less reliable seal may be created.

As mentioned above, in order to properly and effectively seal larger vessels or tissue, a greater closure force between opposing jaw members is required. It is known that a large closure force between the jaws typically requires large actuation forces which are necessary to create a large moment about the pivot for each jaw. This presents a design challenge for instrument manufacturers who must weigh the advantages of manufacturing an overly-simplified design against the disadvantages of a design that may require the user to exert a large closure force to effectively seal tissue. As a result, designers must compensate for these large closure forces by either designing instruments with metal pins and/or by designing instruments which at least partially offload these closure forces to reduce the chances of mechanical failure and reduce fatigue for the end user (i.e., surgeon).

Increasing the closure forces between electrodes may have other undesirable effects, e.g., it may cause the opposing electrodes to come into close contact with one another which may result in a short circuit and a small closure force may cause pre-mature movement of the tissue during compression and prior to activation. As a result thereof, providing an instrument which consistently provides the appropriate closure force between opposing electrode within a preferred pressure range will enhance the chances of a successful seal. As can be appreciated, relying on a surgeon to manually provide the appropriate closure force within the appropriate range on a consistent basis would be difficult and the resultant effectiveness and quality of the seal may vary. Moreover, the overall success of creating an effective tissue seal is greatly reliant upon the user's expertise, vision, dexterity, and experience in judging the appropriate closure force to uniformly, consistently and effectively seal the vessel. In other words, the success of the seal would greatly depend upon the ultimate skill of the surgeon rather than the efficiency of the instrument.

It has been found that the pressure range for assuring a consistent and effective seal is between about 3 kg/cm$^2$ to about 16 kg/cm$^2$ and, preferably, within a working range of 7 kg/cm$^2$ to 13 kg/cm$^2$. Manufacturing an instrument which is capable of providing a closure pressure within this working range has been shown to be effective for sealing arteries, tissues and other vascular bundles.

Various force-actuating assemblies have been developed in the past for providing the appropriate closure forces to effect vessel sealing. For example, one such actuating assembly has been developed by Valleylab, Inc. of Boulder, Colo., a division of Tyco Healthcare LP, for use with Valleylab's vessel sealing and dividing instrument commonly sold under the trademark LIGASURE ATLAS®. This assembly includes a four-bar mechanical linkage, a spring and a drive assembly which cooperate to consistently provide and maintain tissue pressures within the above working ranges. Co-pending U.S. application Ser. Nos. 10/179,863 entitled "VESSEL SEALER AND DIVIDER" (now U.S. Pat. No. 7,101,371), 10/116,944 entitled "VESSEL SEALER AND DIVIDER" (now U.S. Pat. No. 7,083,618), 10/472,295 entitled "VESSEL SEALER AND DIVIDER" (now U.S. Pat. No. 7,101,372) and PCT Application Ser. Nos. PCT/US01/01890 entitled "VESSEL SEALER AND DIVIDER and PCT/US01/11340 entitled "VESSEL SEALER AND DIVIDER" all describe in detail various operating features of the LIGASURE ATLAS® and various methods relating thereto. The contents of all of these applications are hereby incorporated by reference herein.

Other force-actuating mechanisms or assemblies are described in commonly-owned U.S. application Ser. Nos. 10/460,926 entitled "VESSEL SEALER AND DIVIDER FOR USE WITH SMALL TROCARS AND CANNULAS" and 10/953,757 entitled "VESSEL SEALER AND DIVIDER HAVING ELONGATED KNIFE STROKE AND SAFETY FOR CUTTING MECHANISM", the entire contents of both are hereby incorporated by reference herein. As described therein, simpler and more mechanically advantageous actuating and drive assemblies are described therein which facilitate grasping and manipulating vessels and tissue and which reduce user fatigue.

In certain surgical operations, a bipolar forceps is used in combination with a monopolar forceps or monopolar coagulator to treat tissue and control bleeding during the surgery. As such and during the course of a particular operation, a surgeon may be required to substitute a monopolar instrument for the bipolar instrument which would typically involve substitution through the trocar or cannula. As can be appreciated this may occur on more than one occasion over the course of the operation which can be quite time consuming and which may unnecessarily subject the instruments to possible non-sterile environments.

It would be desirous to develop a small, simple and cost effective combination bipolar and monopolar instrument which can be utilized with small cannulas. Moreover, it would be desirous to provide an instrument which includes an easily manipulatable handle and instrument body which includes a mechanically advantageous force-actuating assembly to reduce user fatigue.

SUMMARY

The present disclosure relates to an endoscopic forceps having a housing with a shaft attached thereto, the shaft including a pair of jaw members disposed at a distal end thereof. The forceps also includes a drive assembly disposed in the housing which is configured to move the jaw members relative to one another from a first position wherein the jaw members are disposed in spaced relation relative to one another to a second position wherein the jaw members are closer to one another for manipulating tissue. A pair of handles is operatively connected to the drive assembly and the handles are configured to move relative to the housing to actuate the drive assembly to move the jaw members. Each jaw member is adapted to connect to a source of electrical energy such that the jaw members are capable of conducting energy for treating tissue.

A first switch is disposed on the housing and is activatable to selectively deliver energy of a first electrical potential to at least one jaw member for treating tissue in a monopolar fashion. A second switch is disposed on the housing and is activatable to selectively deliver energy of a first electrical potential to one jaw member and selectively deliver energy of a second electrical potential to the other jaw member for treating tissue in a bipolar fashion.

In one embodiment according to the present disclosure, the forceps also includes a knife assembly which is operatively associated with the housing. The knife assembly is selectively actuatable to advance a knife through tissue disposed between the jaw members when the jaw members are disposed in the second position. In yet another embodiment, at least one of the jaw members may include a monopolar extension which extends beyond the insulative housing of the jaw member to permit delicate dissection of tissue.

In one particularly useful embodiment, at least one of the handles includes a knife lockout which prevents the knife assembly from being actuated when the jaw members are disposed in the second position. The knife lockout mechanism may include a mechanical interface extending from at least one of the handles. The mechanical interface is dimensioned to impede movement of the knife assembly when the handles are disposed in a first (i.e., open) position relative to the housing and the mechanical interface is dimensioned to permit actuation of the knife assembly when the handles are disposed in a second position relative to the housing.

In another embodiment according to the present disclosure, the forceps includes a monopolar lockout which prevents activation of the first switch when the jaw members are disposed in the first position. In one particularly useful embodiment, the monopolar lockout includes a mechanical interface disposed on at least one of the handles which prevents activation of the first switch when the handles are disposed in a first position relative to the housing and permits activation of the first switch when the handles are disposed in a second position relative to the housing. The monopolar lockout may include a pressure activated switch disposed in the housing such that movement of the handles from a first position relative to the housing to a second position relative to the housing closes the pressure activated switch to allow activation of the first switch.

In still yet another embodiment according to the present disclosure, the handles of the forceps are disposed on opposite sides of the housing and are movable from a first, spaced position relative to the housing to a second closer position relative to the housing. The housing may also be configured to include a pair of slits defined on opposite sides of the housing and the handles may be dimensioned to move relative to the housing within the slits. In one particularly useful embodiment, the housing includes a longitudinal axis defined therethrough and the handles are disposed at an angle "α" relative to the longitudinal axis to facilitate handling.

In yet another embodiment according to the present disclosure, an intensity controller is included which regulates the intensity of electrosurgical energy to the forceps during activation. In a particularly useful embodiment, the intensity controller is a slide potentiometer and is operable only in a monopolar mode.

In still another embodiment, the forceps may include an electrical safety which regulates the forceps to operating in either a bipolar fashion or a monopolar fashion during any given time. In a particularly useful embodiment, the first switch and the second switch are independently and exclusively activatable relative to one another.

The present disclosure also relates to an electrosurgical system having an electrosurgical generator and an endoscopic forceps. The forceps includes a housing having a shaft attached thereto with a pair of jaw members disposed at a distal end thereof. The jaw members are adapted to connect to the electrosurgical generator. The forceps also includes a drive assembly disposed in the housing which moves the jaw members relative to one another from a first position wherein the jaw members are disposed in spaced relation relative to one another to a second position wherein the jaw members are closer to one another for manipulating tissue. A pair of handles is operatively connected to the drive assembly to actuate the drive assembly to move the jaw members.

A first switch is disposed on the housing and is activatable to selectively deliver energy of a first electrical potential to at least one jaw member for treating tissue in a monopolar fashion. A second switch is disposed on the housing and is activatable to selectively deliver energy of a first electrical potential to one jaw member and selectively deliver energy of a second electrical potential to the other jaw member for treating tissue in a bipolar fashion.

In one embodiment, the generator includes a control circuit having a safety circuit which permits independent and exclusive activation of the forceps in either a bipolar or monopolar fashion. The safety circuit may be electrical or electro-mechanical and activated upon movement to the pair of handles relative to the housing. The generator may also include a control circuit having an isolation circuit operably connected to the second switch which regulates the energy to the jaw members while bypassing the second switch to protect the integrity of the second switch from current overload.

The present disclosure also relates to an endoscopic forceps having a housing with a shaft attached thereto. The shaft includes a pair of jaw members disposed at a distal end thereof. Each jaw member is adapted to connect to a source of electrical energy such that the jaw members are capable of conducting energy for treating tissue. A drive assembly is disposed in the housing and is operable to move the jaw members relative to one another from a first position, wherein the jaw members are disposed in spaced relation relative to one another, to a second position, wherein the jaw members are closer to one another, for manipulating tissue. A pair of handles operatively connects to the drive assembly and is movable relative to the housing to actuate the drive assembly to move the jaw members.

A knife assembly is included which is operatively associated with the housing. The knife assembly is selectively actuatable to advance a knife through tissue disposed between the jaw members when the jaw members are disposed in the second position. The knife assembly includes at least one safety mechanism to prevent damaging the knife upon selective actuation thereof.

In one embodiment, the safety mechanism includes a mechanical fuse which fractures upon exertion of excessive force (a force of about 9 lbf or greater) to actuate the knife assembly. In another embodiment, the knife assembly includes a pinion gear interdisposed between a set of gear teeth and a track which cooperate to advance the knife distally through the jaw members. The mechanical fuse may be operatively associated with the pinion gear, gear teeth and/or the track. In one particular embodiment, an axle of the pinion gear is designed to fracture upon excessive force to actuate the knife assembly. In another embodiment according to the present disclosure, first and second switches may be included to deliver energy to the jaw members as described mentioned above.

The present disclosure also relates to an endoscopic forceps having a housing with a shaft attached thereto. The shaft includes a pair of jaw members disposed at a distal end thereof, each jaw member adapted to connect to a source of electrical energy such that the jaw members are capable of conducting energy for treating tissue. A drive assembly is disposed in the housing and is operable to move the jaw members relative to one another from a first position, wherein the jaw members are disposed in spaced relation relative to one another, to a second position, wherein the jaw members are closer to one another, for manipulating tissue. A pair of handles is included which operatively connects to the drive assembly and is movable relative to the housing to actuate the drive assembly to move the jaw members.

A switch is included which is disposed on the housing and is activatable to selectively deliver energy of a first electrical potential to at least one jaw member for treating tissue. The switch is operatively coupled to an intensity control mechanism disposed within the housing which is selectively adjustable to regulate the level of electrosurgical energy to at least one jaw member. In one embodiment, the intensity control mechanism is selectively adjustable in discrete increments. In another embodiment, the intensity control mechanism includes a first mechanical interface (e.g., a detent) configured to engage a series of corresponding mechanical interfaces (e.g., recesses) defined in the housing to regulate the level of electrosurgical energy in discrete increments. The detent may be disposed in a cantilevered fashion atop the intensity control mechanism and the intensity control mechanism may be disposed atop a railway to facilitate movement thereof.

In yet another embodiment, the intensity control mechanism includes a second mechanical interface (e.g., a slide bump) that cooperates with the detent to mechanically engage a circuit board disposed within the housing at discrete locations when the detent engages a corresponding one of the series of recesses.

The present disclosure also relates to an endoscopic forceps having a housing with a shaft attached thereto. The shaft includes a pair of jaw members disposed at a distal end thereof, each jaw member adapted to connect to a source of electrical energy such that the jaw members are capable of conducting energy for treating tissue. A drive assembly is disposed in the housing and is operable to move the jaw members relative to one another from a first position, wherein the jaw members are disposed in spaced relation relative to one another, to a second position, wherein the jaw members are closer to one another, for manipulating tissue. A pair of handles operatively connects to the drive assembly and is movable relative to the housing to actuate the drive assembly to move the jaw members.

A switch is disposed on the housing and is activatable to selectively deliver energy of a first electrical potential to at least one jaw member for treating tissue. First and second toggle links are included which operatively connect each one of the pair of handles to the drive assembly. Each of the toggle links includes first and second anchoring elements, the first anchoring element operatively engaging the handle and the second anchoring element operatively engaging the drive assembly.

In one embodiment, the first and second anchoring elements each include a pair of tapered double tangs which operatively engage the handle and the drive assembly, respectively, in a snap-fit manner. Each pair of double tangs may include a step at a proximal end thereof for seating each pair of double tangs within a respective aperture defined within the handle and the drive assembly.

A slot may be defined between each pair double tangs. The slots may be oriented such that the greatest cross sectional area of the double tangs offsets an applied load on the forceps thereby preventing failure of the toggle links during actuation of the handles.

BRIEF DESCRIPTION OF THE DRAWINGS

Various embodiments of the subject instrument are described herein with reference to the drawings wherein:

FIG. 8A is a greatly-enlarged, top cross sectional view of an end effector of the end effector assembly showing a knife of the knife actuator in a proximal-most or unactuated position;

FIG. 8B is a greatly-enlarged, top cross sectional view of the end effector assembly of FIG. 8A showing the position of the knife after actuation;

FIG. 10A is a greatly-enlarged, side cross sectional view of the end effector assembly shown in an open configuration;

FIG. 10B is a greatly-enlarged, side cross sectional view of the end effector assembly shown in a closed configuration;

FIG. 16 is an enlarged, perspective view of a circuit board for use with the forceps according to the present disclosure;

DETAILED DESCRIPTION

Figure 1A:
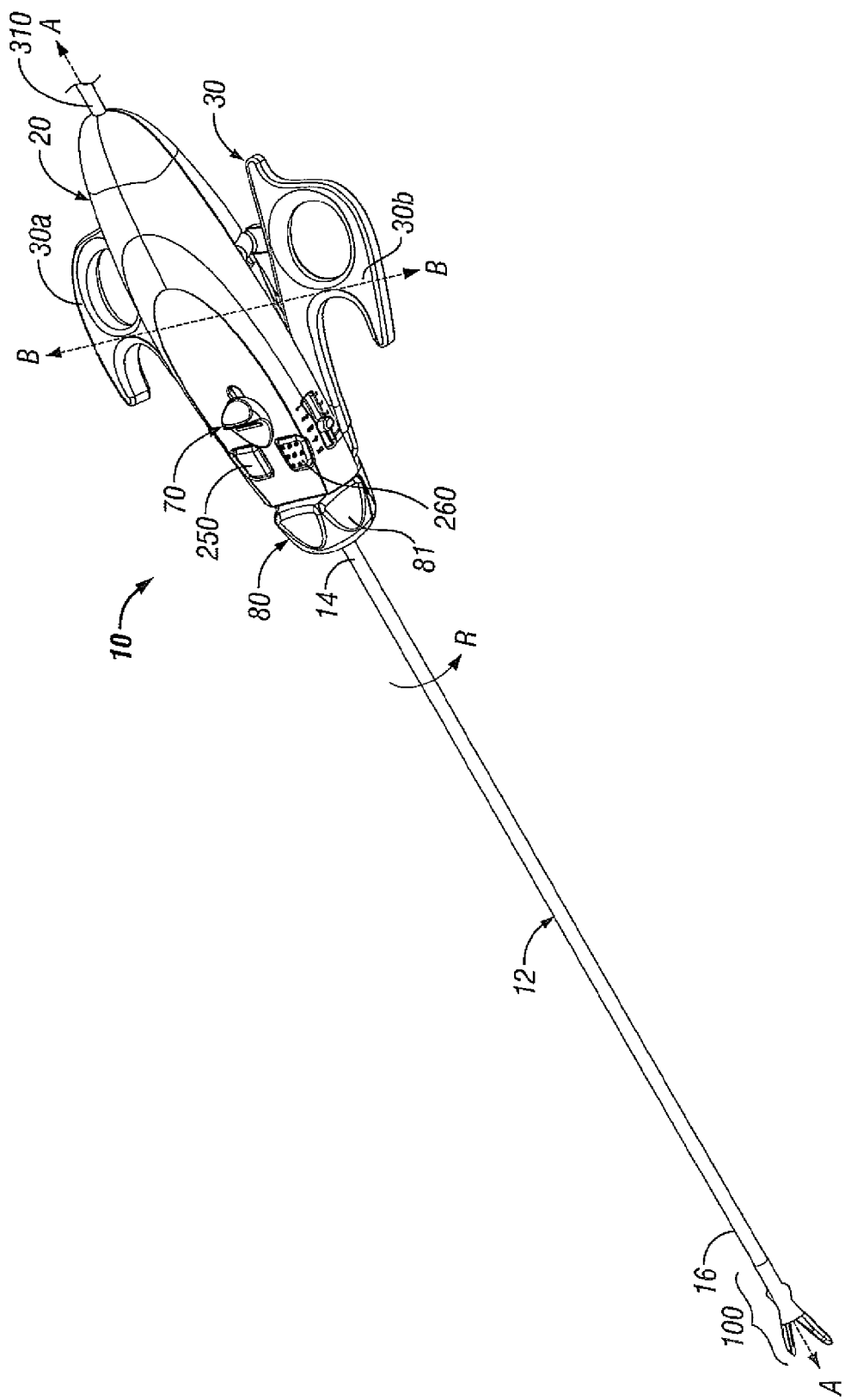
FIG. 1A is a top, perspective view of an endoscopic forceps shown in an open configuration and including a housing, a handle assembly, a shaft and an end effector assembly according to the present disclosure.
Figure 1B:
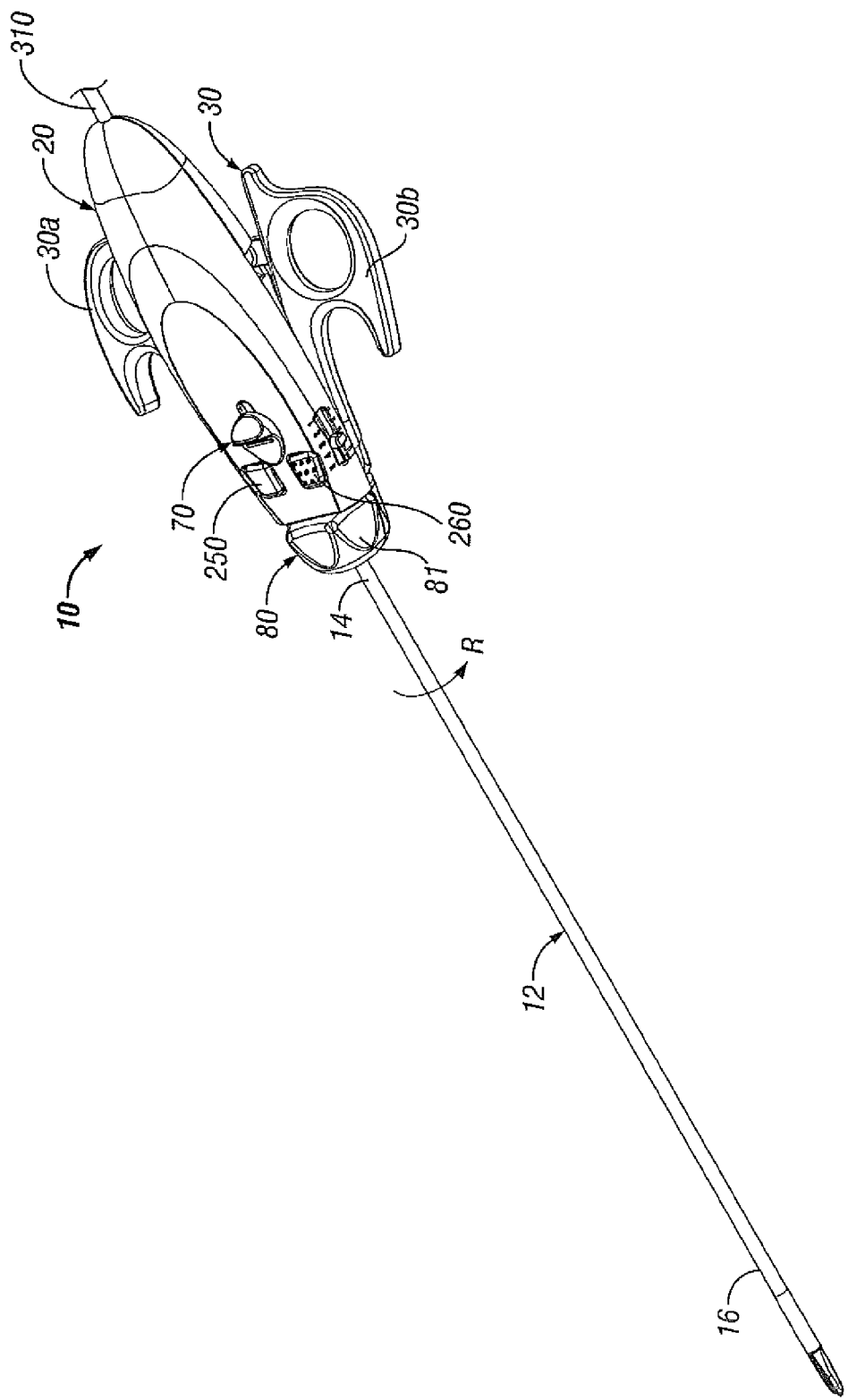
FIG. 1B is a top, perspective view of the endoscopic forceps of FIG. 1A showing the end effector assembly in a closed configuration according to the present disclosure.
Figure 2:
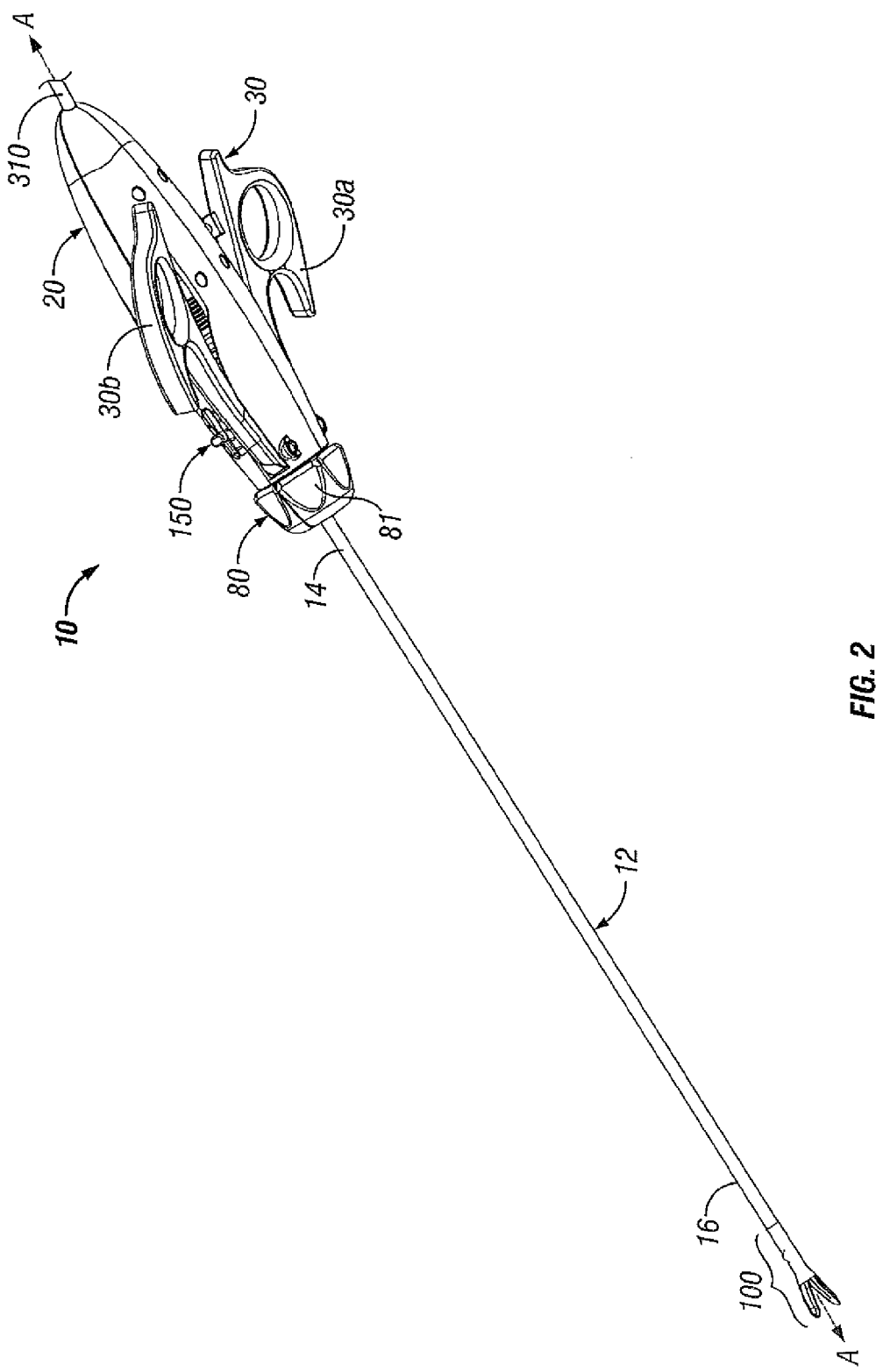
FIG. 2 is a bottom, perspective view of the endoscopic forceps of FIG. 1A.
Figure 10C:
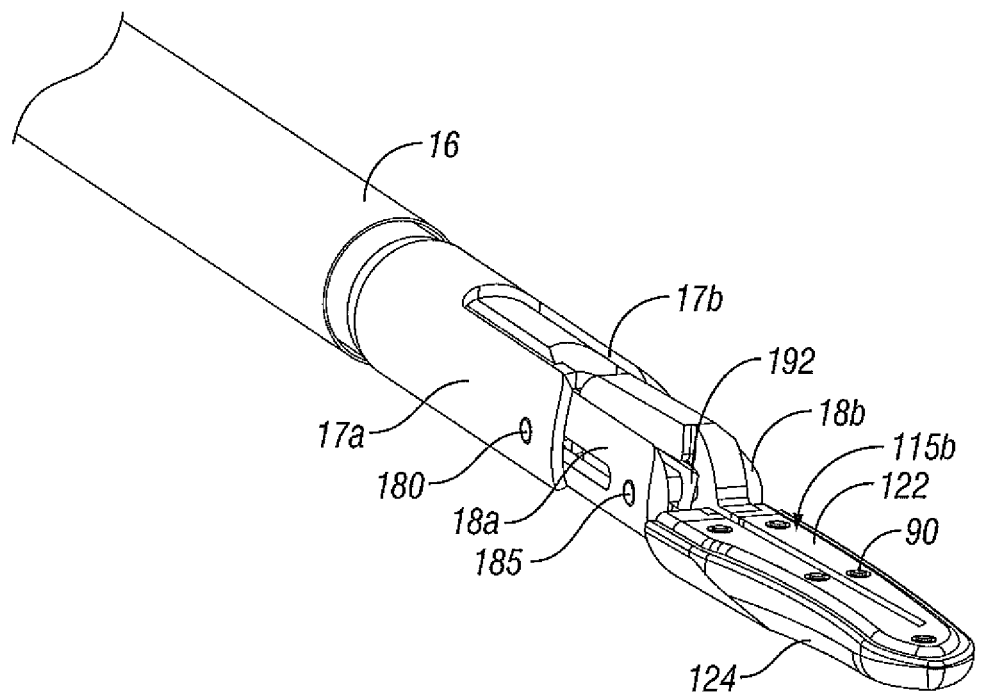
FIG. 10C is a greatly-enlarged, front perspective view of a bottom jaw member of the end effector assembly showing the knife of the knife actuator in a proximal-most or unactuated position.
Figure 10D:
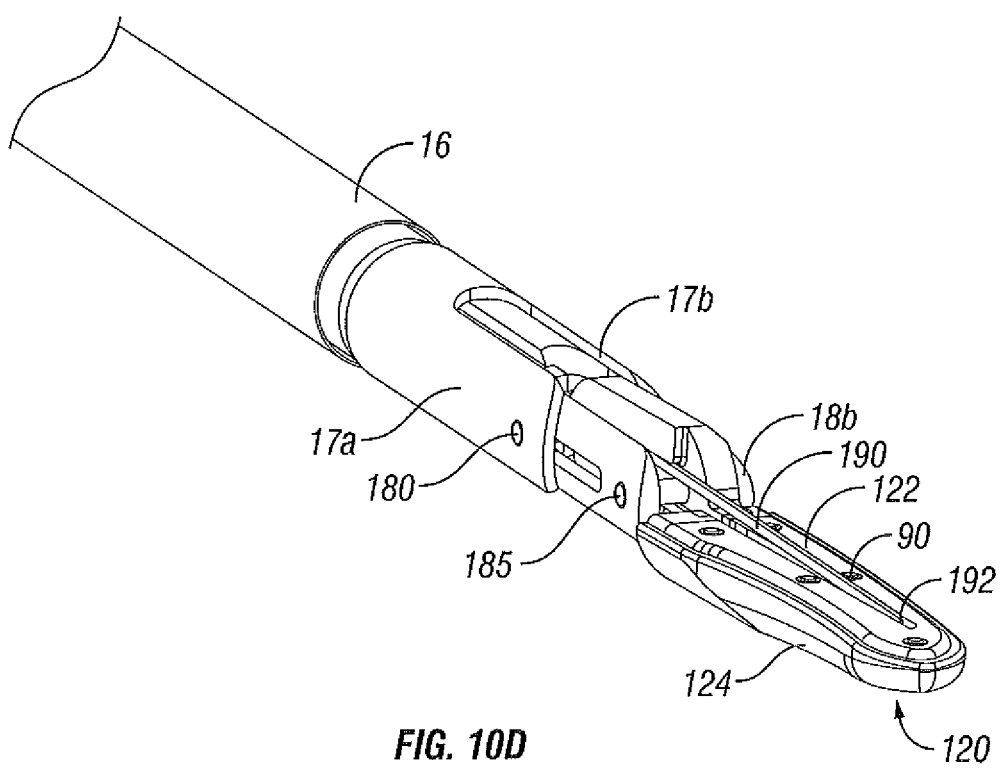
FIG. 10D is a greatly-enlarged, front perspective view of the bottom jaw member of FIG. 10C showing the position of the knife after actuation.

Turning now to FIGS. 1A-2, one embodiment of a combination endoscopic bipolar and monopolar forceps 10 is shown for use with various surgical procedures and generally includes a housing 20, a handle assembly 30, a rotating assembly 80, a knife trigger assembly 70 and an end effector assembly 100 which mutually cooperate to grasp, seal and divide tubular vessels and vascular tissue (FIGS. 10A and 10B). Although the majority of the figure drawings depict a forceps 10 for use in connection with endoscopic surgical procedures, the present disclosure may be used for more traditional open surgical procedures. For the purposes herein, the forceps 10 is described in terms of an endoscopic instrument; however, it is contemplated that an open version of the forceps may also include the same or similar operating components and features as described below.

Forceps 10 includes a shaft 12 which has a distal end 16 dimensioned to mechanically engage the end effector assembly 100 and a proximal end 14 which mechanically engages the housing 20. Details of how the shaft 12 connects to the end effector are described in more detail below. The proximal end 14 of shaft 12 is received within the housing 20 and the connections relating thereto are also described in detail below. In the drawings and in the descriptions which follow, the term "proximal", as is traditional, will refer to the end of the forceps 10 which is closer to the user, while the term "distal" will refer to the end which is further from the user.

Forceps 10 also includes an electrosurgical cable 310 which connects the forceps 10 to a source of electrosurgical energy, e.g., a generator 500 (See FIG. 16). Generators such as those sold by Valleylab—a division of Tyco Healthcare LP, located in Boulder Colo. may be used as a source of both bipolar electrosurgical energy for sealing vessel and vascular tissues as well as monopolar electrosurgical energy which is typically employed to coagulate or cauterize tissue. It is envisioned that the generator 500 may include various safety and performance features including isolated output, impedance control and/or independent activation of accessories. The electrosurgical generator 500 may also be configured to include Valleylab's Instant Response™ technology which provides an advanced feedback system to sense changes in tissue two-hundred (200) times per second and adjust voltage and current to maintain appropriate power. The Instant Response™ technology is believed to provide one or more of the following benefits to surgical procedure:

Consistent clinical effect through all tissue types;

Reduced thermal spread and risk of collateral tissue damage;

Less need to "turn up the generator"; and

Designed for the minimally invasive environment.

As best show in FIG. 16, cable 310 is divided into cable leads 310a and 310b which are configured to connect the forceps to the electrosurgical generator 500 by virtue of one or more connectors or by virtue of separate so-called "flying leads" which are configured to connect to the generator 500 at a single location and provide either bipolar, monopolar (or a combination thereof) energy as desired or based upon the particular instrument configuration set up by the surgeon prior to surgery. One example of a universal electrical connector is being currently developed by Valleylab, Inc. of Boulder, Colo. a division of Tyco Healthcare, LP and is the subject of U.S. patent application Ser. No. 10/718,114 entitled "CONNECTOR SYSTEMS FOR ELECTROSURGICAL GENERATOR" the entire contents of which is incorporated by reference herein.

Handle assembly 30 includes two movable handles 30a and 30b disposed on opposite sides of housing 20. Handles 30a and 30b are movable relative to one another to actuate the end effector assembly 100 as explained in more detail below with respect to the operation of the forceps 10.

Figure 13:
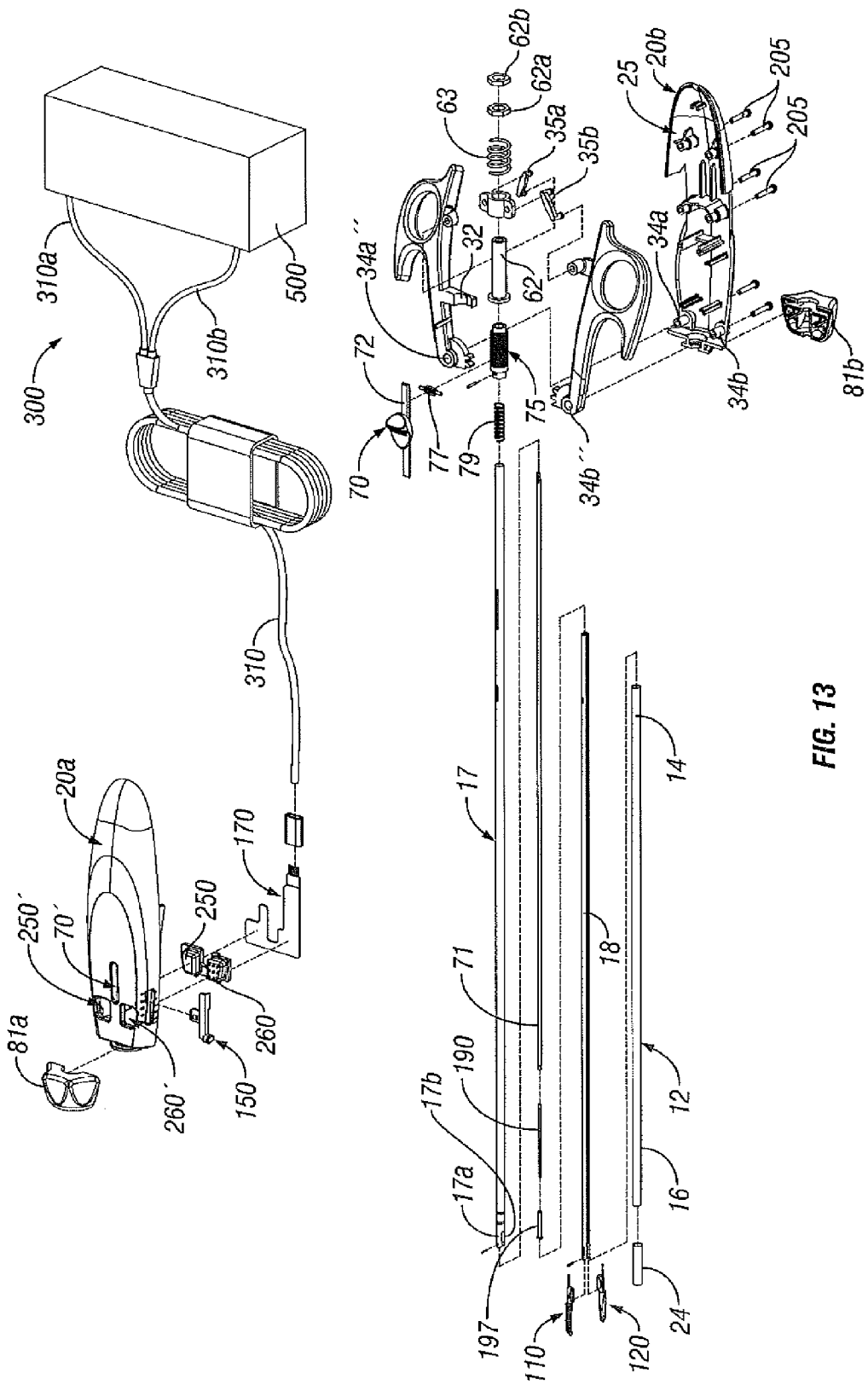
FIG. 13 is a top, perspective view of the forceps with parts separated.

As best seen in the exploded view of FIG. 13, housing 20 is formed from two (2) housing halves 20a and 20b which each include a plurality of interfaces 205 which are dimensioned to mechanically align and engage one another to form housing 20 and enclose the internal working components of forceps 10. It is envisioned that a plurality of additional interfaces (not shown) may disposed at various points around the periphery of housing halves 20a and 20b for ultrasonic welding purposes, e.g., energy direction/deflection points. It is also contemplated that housing halves 20a and 20b (as well as the other components described below) may be assembled together in any fashion known in the art. For example, alignment pins, snap-like interfaces, tongue and groove interfaces, locking tabs, adhesive ports, etc. may all be utilized either alone or in combination for assembly purposes.

Rotating assembly 80 is mechanically coupled to housing 20 and is rotatable approximately 90 degrees in either direction about a longitudinal axis "A" (See FIGS. 1A-2 and 12). Details of the rotating assembly 80 are described in more detail with respect to FIGS. 12-14. Rotating assembly 80 includes two halves 81a and 81b which, when assembled, form the rotating assembly 80 which, in turn, supports the elongated shaft 12 which houses drive assembly 60 and the knife assembly 70. Halves 81a and 81b are mechanically engaged to housing 20 atop flanges 82a and 82b, respectively, during assembly and may include other mechanical interfaces dimensioned to securely engage the two halves 81a and 81b of the rotating assembly 80, e.g., alignment pins, snap-fit interfaces, ultrasonic welding points, etc.

As mentioned above, end effector assembly 100 is attached at the distal end 16 of shaft 12 and includes a pair of opposing jaw members 110 and 120 (See FIGS. 3A-3D). Handles 30a and 30b of handle assembly 30 ultimately connect to drive assembly 60 which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue (FIGS. 10A and 10B) therebetween.

It is envisioned that the forceps 10 may be designed such that it is fully or partially disposable depending upon a particular purpose or to achieve a particular result. For example, end effector assembly 100 may be selectively and releasably engageable with the distal end 16 of the shaft 12 and/or the proximal end 14 of shaft 12 may be selectively and releasably engageable with the housing 20 and the handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed. As can be appreciated, the presently disclosed electrical connections may have to be altered to modify the instrument to a reposable forceps.

Turning now to the more detailed features of the present disclosure as described with respect to FIGS. 1A-16, handles 30a and 30b each include an aperture 33a and 33b, respectively, defined therein which enables a user to grasp and move each respective handle 30a and 30b relative to one another. Handles 30a and 30b also include ergonomically-enhanced gripping elements 39a and 39b, respectively, disposed along an outer edge thereof which are designed to facilitate gripping of the handles 30a and 30b during activation. It is envisioned that gripping elements 39a and 39b may include one or more protuberances, scallops and/or ribs to enhance gripping.

Figure 7:
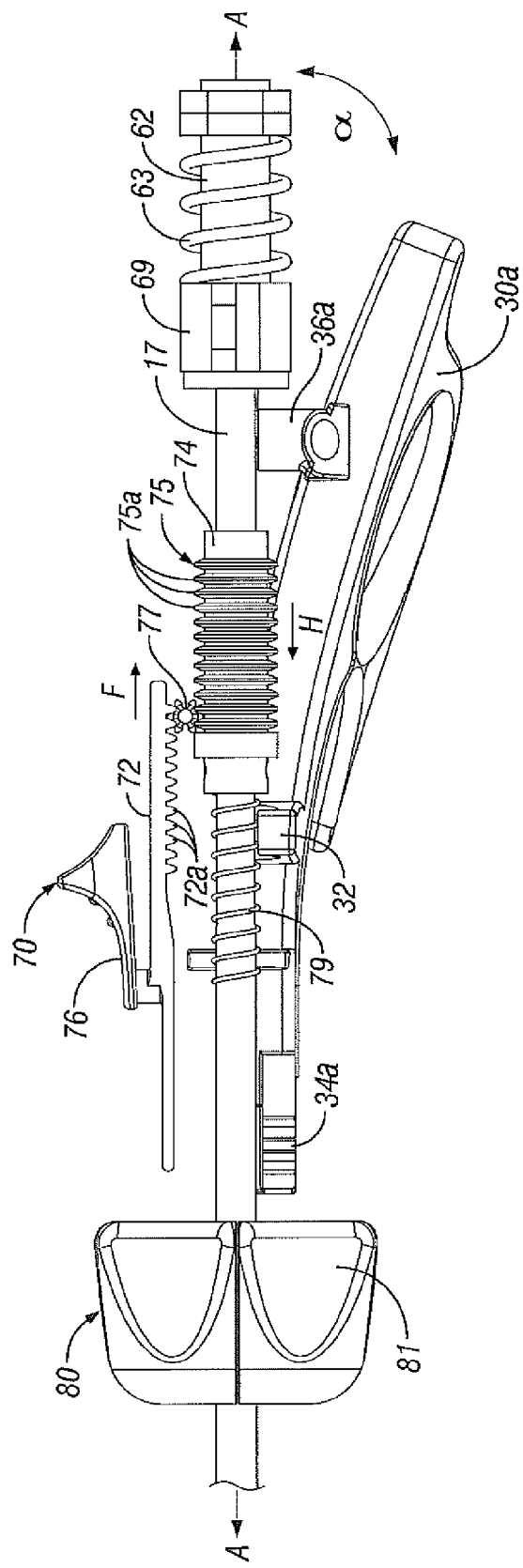
FIG. 7 is an enlarged side view of the knife actuator in an un-actuated position.

As best illustrated in FIGS. 1A and 7, handles 30a and 30b are configured to extend outwardly on opposite sides from a transverse axis "B" defined through housing 20 which is perpendicular to longitudinal axis "A". Handles 30a and 30b are movable relative to one another in a direction parallel to axis "B" to open and close the jaw members 110 and 120 as needed during surgery. This forceps style is commonly referred to as an "in-line" or hemostat style forceps as compared to a so-called "pistol grip" style forceps or endoscopic instrument. In-line hemostats or forceps are more commonly manufactured for open surgical procedures and typically include a pair of shafts having integrally coupled handles which are movable relative to one another to open and close the jaw members disposed at the distal end thereof.

Figure 5A:
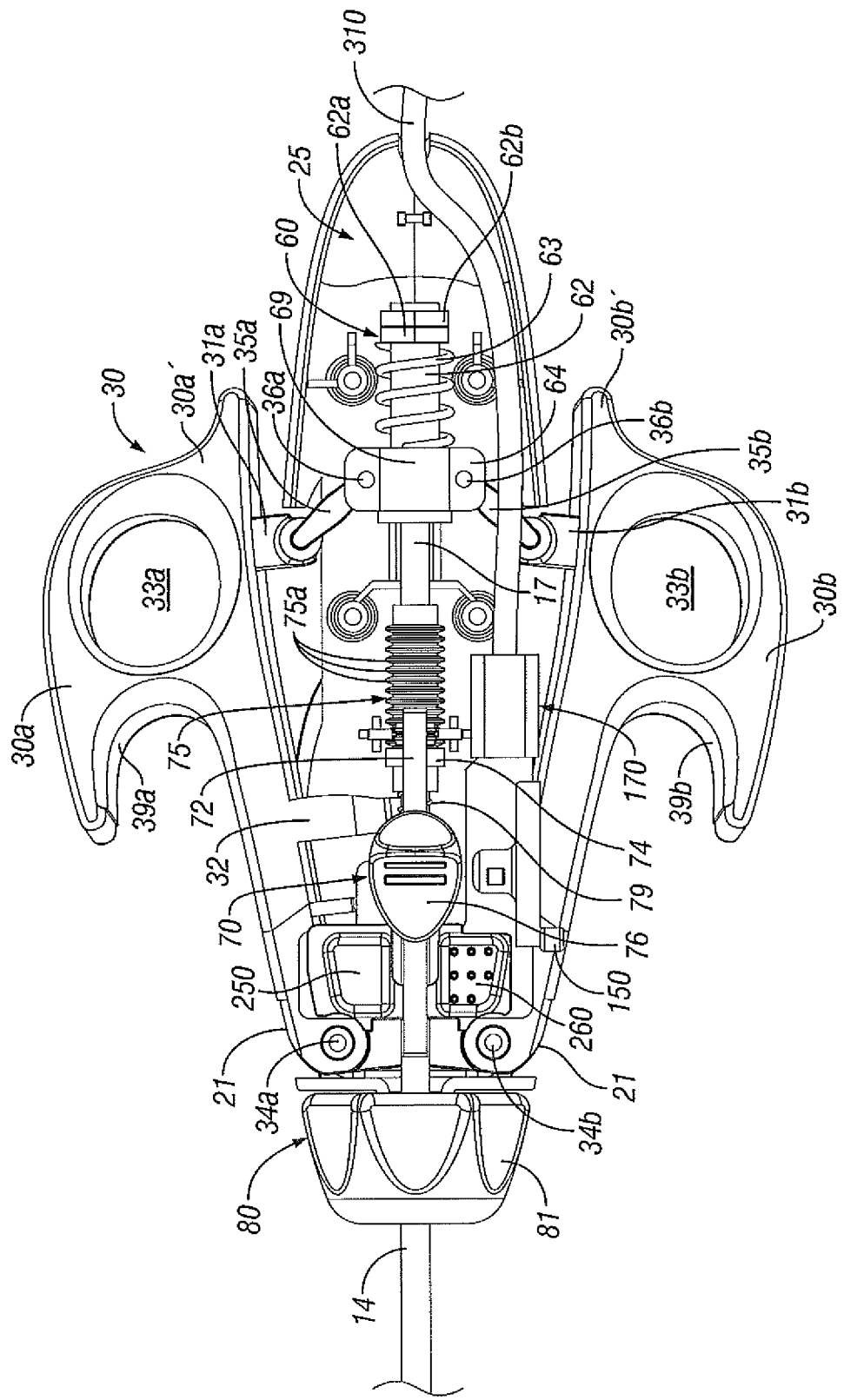
FIG. 5A is an enlarged, top view of the forceps of FIG. 1A showing the disposition of the internal components when the forceps is in an open configuration.
Figure 5B:
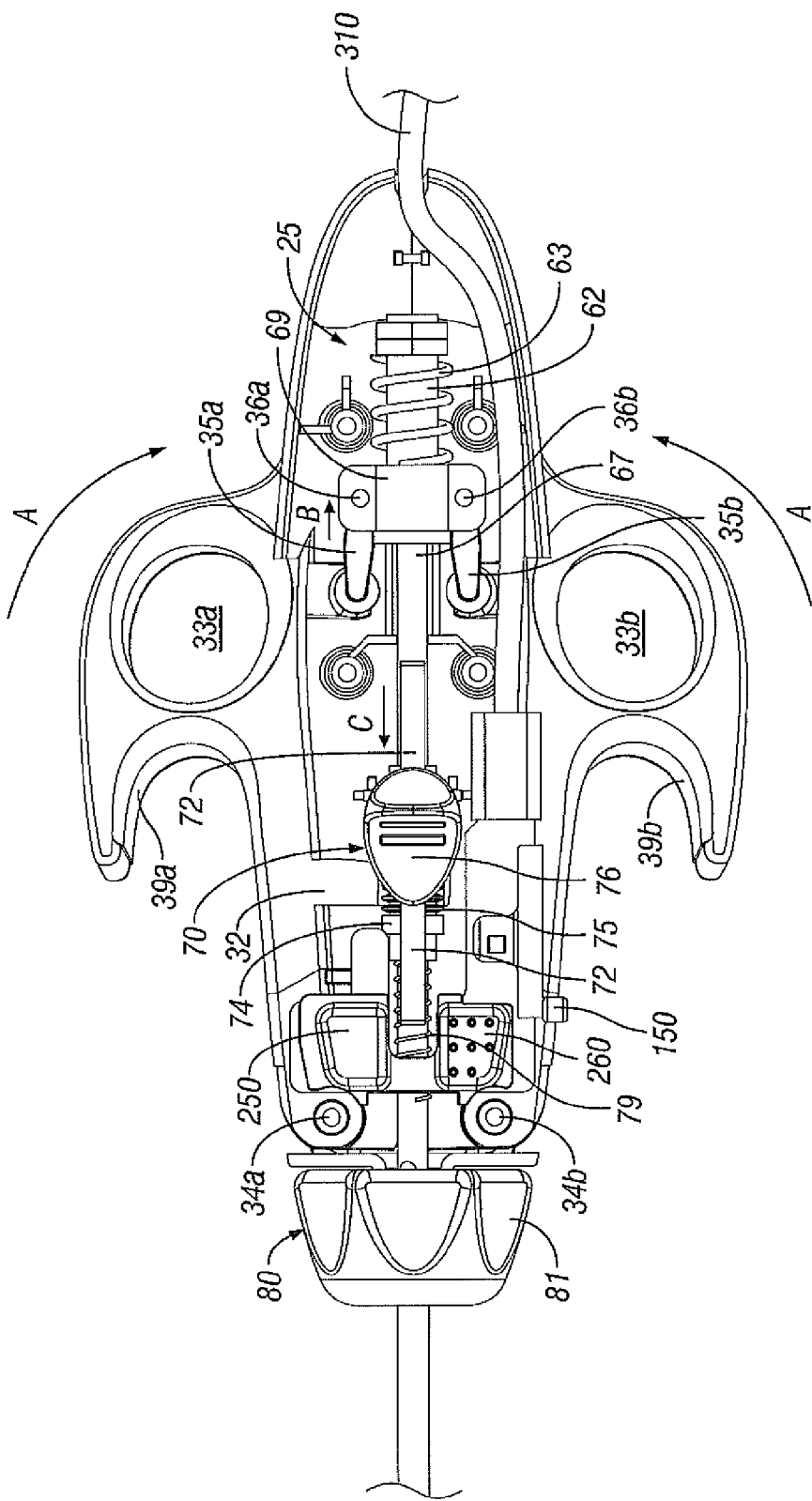
FIG. 5B is an enlarged, top view of the forceps of FIG. 1B showing the disposition of the internal components when the forceps is in a closed configuration.

As best illustrated in FIG. 5A and as mentioned above, handles 30a and 30b mechanically couple to the housing 20 and are movable relative to the housing (and each other) to affect movement of the jaw members 110 and 120 from the open or spaced configuration to a closed position about tissue. Each handle, e.g., handle 30a shown in FIG. 7, is also configured to extend downwardly at an angle alpha (α) relative to the longitudinal axis "A". It is envisioned that manufacturing the handles 30a and 30b to extend in this fashion facilitates and enhances gripping and manipulation of the forceps 10 during operating conditions. It is envisioned that the angle (α) of the handles 30a and 30b of forceps 10 may be adjustable to allow different users to essentially "customize" the handles 30a and 30b for a particular use of for a particular hand size. Alternatively, different forceps 10 may be manufactured with different pre-fixed angles (α) for use with specific surgical procedures, for particular hand sizes (i.e., small, medium and large) and/or for other surgical purposes. It is further contemplated that in a particularly useful embodiment, the angle (α) of the handle ranges from about zero degrees (0°) degrees to about thirty-five degrees (35°).

As best seen in FIGS. 5A, 5B, 13 and 14, the distal end 34 and 37 of each handle 30a and 30b, respectively, is selectively moveable about pivot pins 34a and 34b attached to a distal end 21 of the housing 20. As explained in more detail below, movement of the handles relative to one another imparts movement of the jaw members 110 and 120 relative to one another. The distal ends 34 and 37 are configured to include complimentary gear teeth 34a' and 34b' which are configured to intermesh with one another to facilitate consistent movement of the handle members 30a and 30b relative to one another and to enhance actuation of the jaw members 110 and 120.

Figure 14:
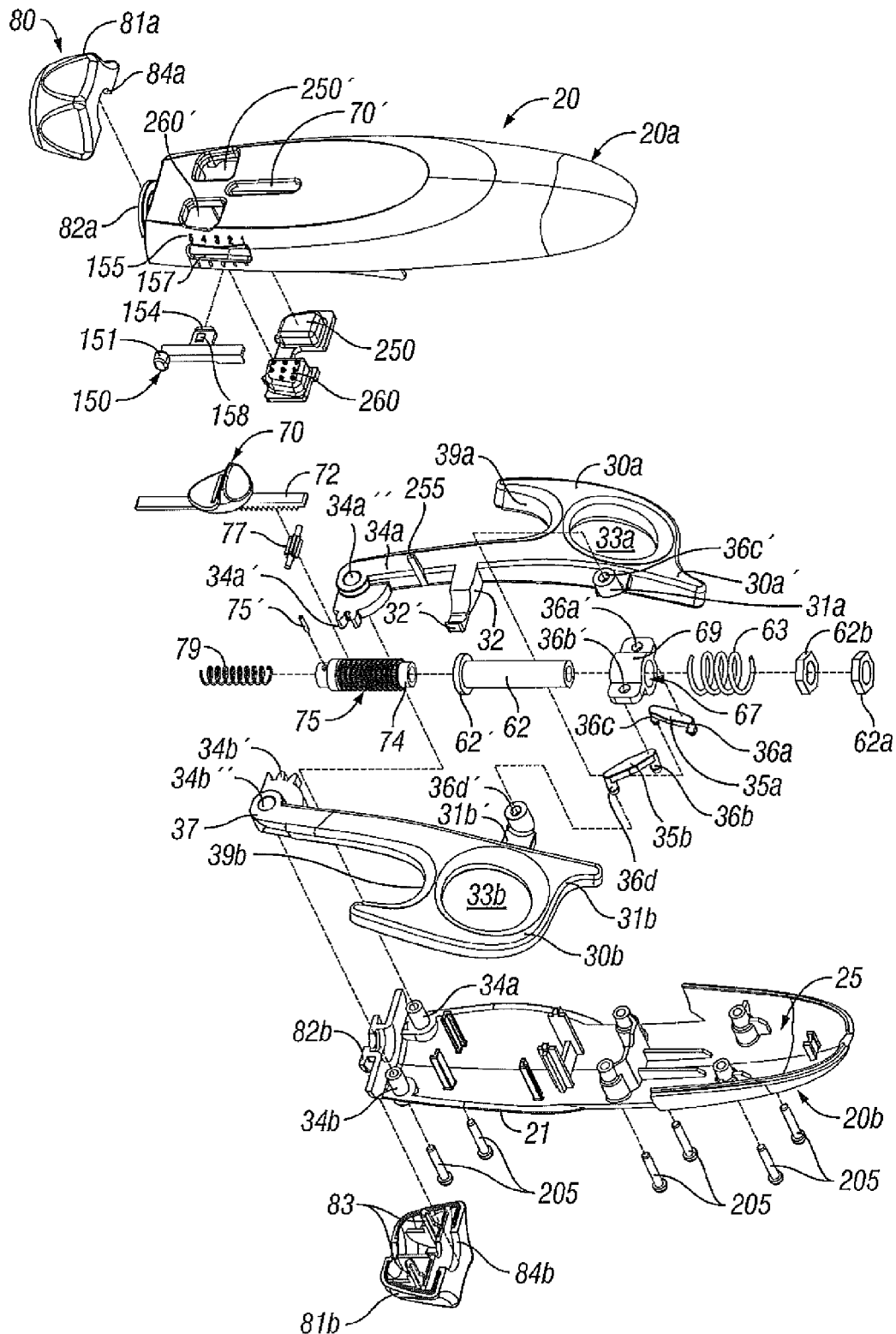
FIG. 14 is an enlarged, perspective view of the housing with parts separated.

In FIG. 14, the proximal end 30a' and 30b' of the each handle 30a and 30b, respectively, includes a flange 31a and 31b which extends from the proximal end 30a' and 30b' of each handle 30a and 30b towards the housing 20. Each of the flanges 31a and 31b includes an aperture 36c' and 36d' disposed therein for receiving an end 36c and 36d of a toggle link 35a and 35b, respectively. The opposite ends 36a and 36b of the toggle links 35a and 35b are configured to attached to an actuating or drive collar 69 of the drive assembly 60 through corresponding apertures 36a' and 36b' defined therethrough. It is envisioned that the toggle links 35a and 35b may be dimensioned in a generally S-shaped configuration to attach the handles 30a and 30b to the drive collar 69 or the toggle links 35a and 35b may be generally U-shaped (as disclosed) to accomplish this purpose. It is contemplated that dimensioning the toggle links 35a and 35b in a U-shaped configuration may reduce buckling during actuation.

Figure 28:
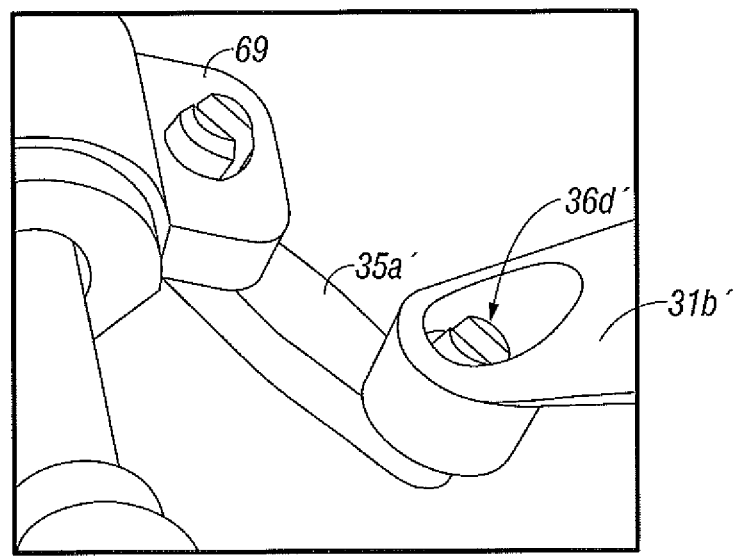
FIG. 28 is a computer-simulated perspective view showing a tapered toggle link operatively connecting the drive assembly to a handle of the handle assembly.
Figure 29:
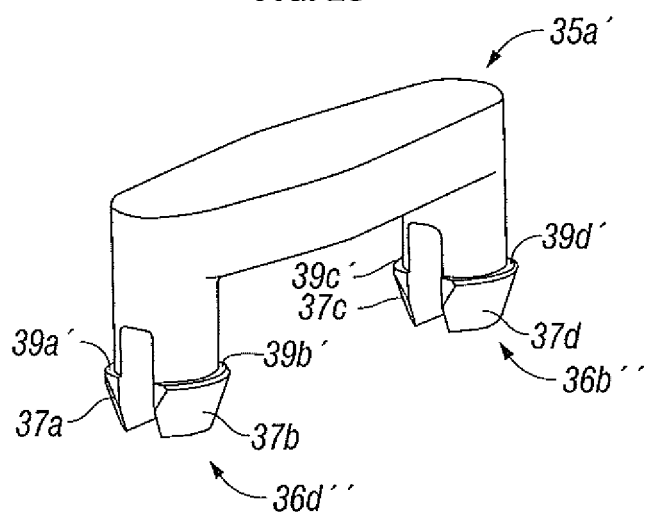
FIG. 29 is an enlarged, perspective view of one embodiment of a toggle link showing a pair double tang anchoring element.
Figure 30:
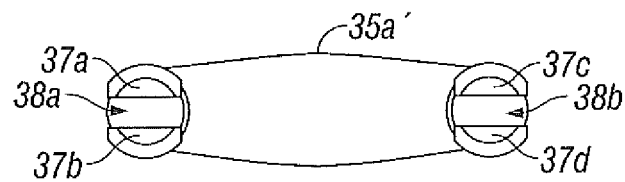
FIG. 30 is an enlarged top view showing the orientation of a pair of slots each defined between one of the pair double tang anchoring elements.

In one envisioned embodiment, the toggle links, e.g., toggle link 35a', are generally symmetrical and include snap-like mechanical interfaces at the distal ends thereof to facilitate manufacture and assembly. More particularly and as best shown in FIGS. 28-30, link 35a' includes two double tang anchoring elements 36d" and 36b" at opposite ends thereof which are designed to correspondingly engage the drive collar 69 to a respective handle, e.g., 30b. In other words, anchor element 36d" is configured to engage aperture 36d' of the handle 30b and anchor element 36b" is configured to engage aperture 36b' of drive collar 69 to link the drive collar 69 to handle 30b.

As can be appreciated, the geometry of each respective double tang anchor elements 36b" and 36d" includes a pair of tapered double tangs 37a, 37b and 37c, 37d. Each pair of double tangs 37a, 37b and 37c, 37d, respectively, includes a step 39a', 39b' and 39c' and 39d', respectively, at a proximal end thereof. Each pair of opposing tangs 37a, 37b and 37c, 37d includes a slot 38a and 38b, respectively, defined therebetween to allow each tang 37a, 37b and 37c, 37d to deflect inwardly to reduce the cross section of the anchoring element 36d" and 36b". As can be appreciated, upon assembly into a corresponding aperture, e.g., 36d and 36b, the taper of each tang 37a, 37b and 37c, 37d forces each tang 37a, 37b and 37c, 37d inwardly to reduce the cross section of each anchoring element 36d" and 36b" to facilitate engagement of the anchoring elements 36d" and 36b" within a corresponding aperture 36d' and 36b'. Once the double tangs 37a, 37b and 37c, 37d are engaged within the respective apertures 36d" and 36b" past steps 39a', 39b' and 39c' and 39d', the tangs 37a, 37b and 37c, 37d spring outwardly to engage and seat the respective anchoring element 36d" and 36b" within the corresponding apertures 36d' and 36b'. Once assembled, the slots 38a and 38b are preferably oriented such that the greatest cross sectional area of each anchoring element 36d" and 36b", i.e., the area with the most material, resides in the direction of the load when applied to close the jaw members 110 and 120 (See FIGS. 28 and 30). This prevent the toggle links 35a' and 35b' from failing due to an overstressed condition or repeated use.

As can be appreciated, movement of the handles 30a and 30b from an open or spaced apart configuration to a closed position towards the housing forces the actuating collar 69 proximally against a spring 63 which, in turn, translates a drive shaft 17 proximally to close the jaw members 110 and 120 (see FIGS. 7-9). The operative relationship of the drive collar 69 and the handle assembly 30 is explained in detail below with respect to the operation of the forceps 10.

Figure 9A:
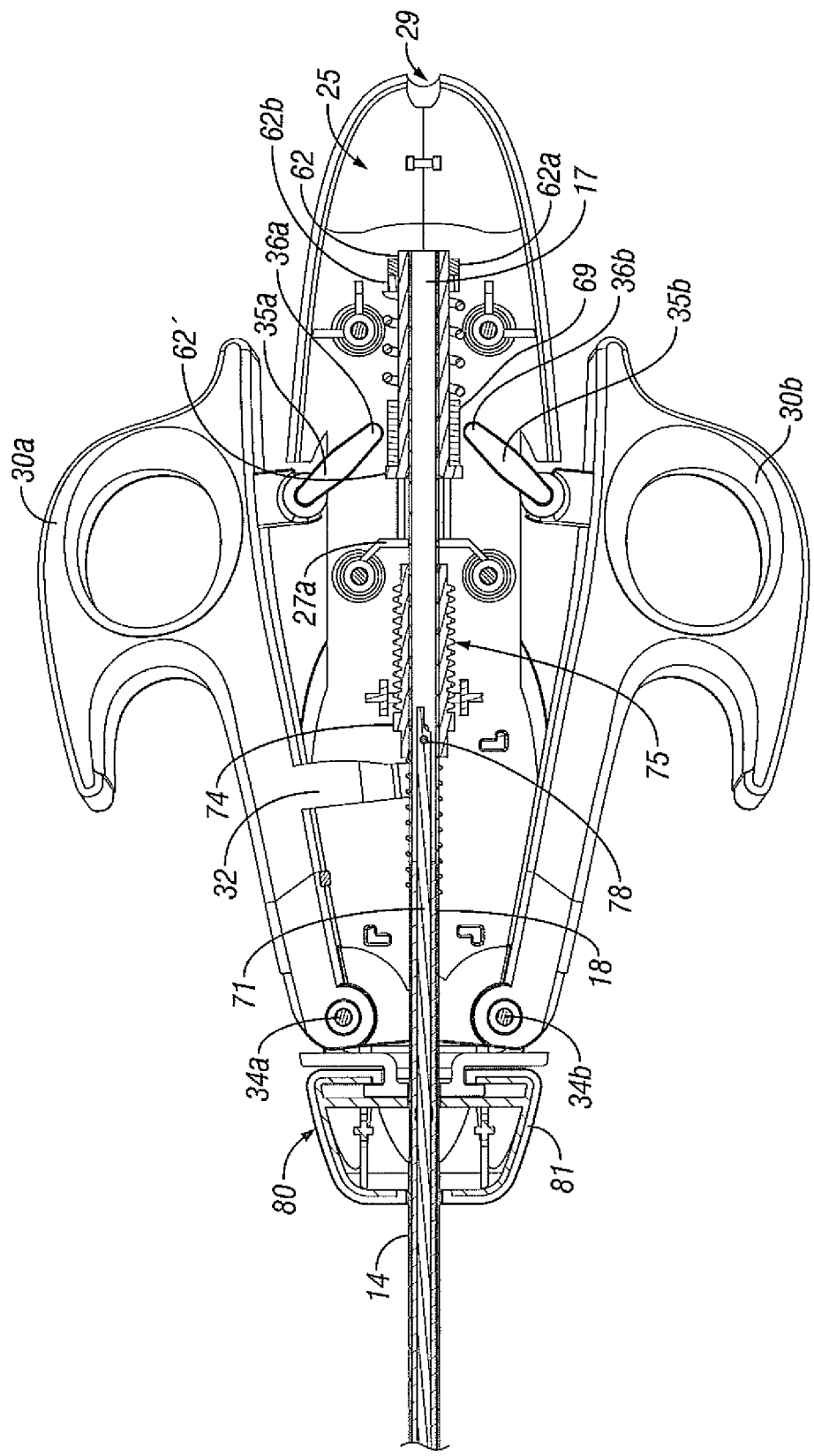
FIG. 9A is an enlarged, top view showing the handle assembly in an unactuated position.
Figure 9B:
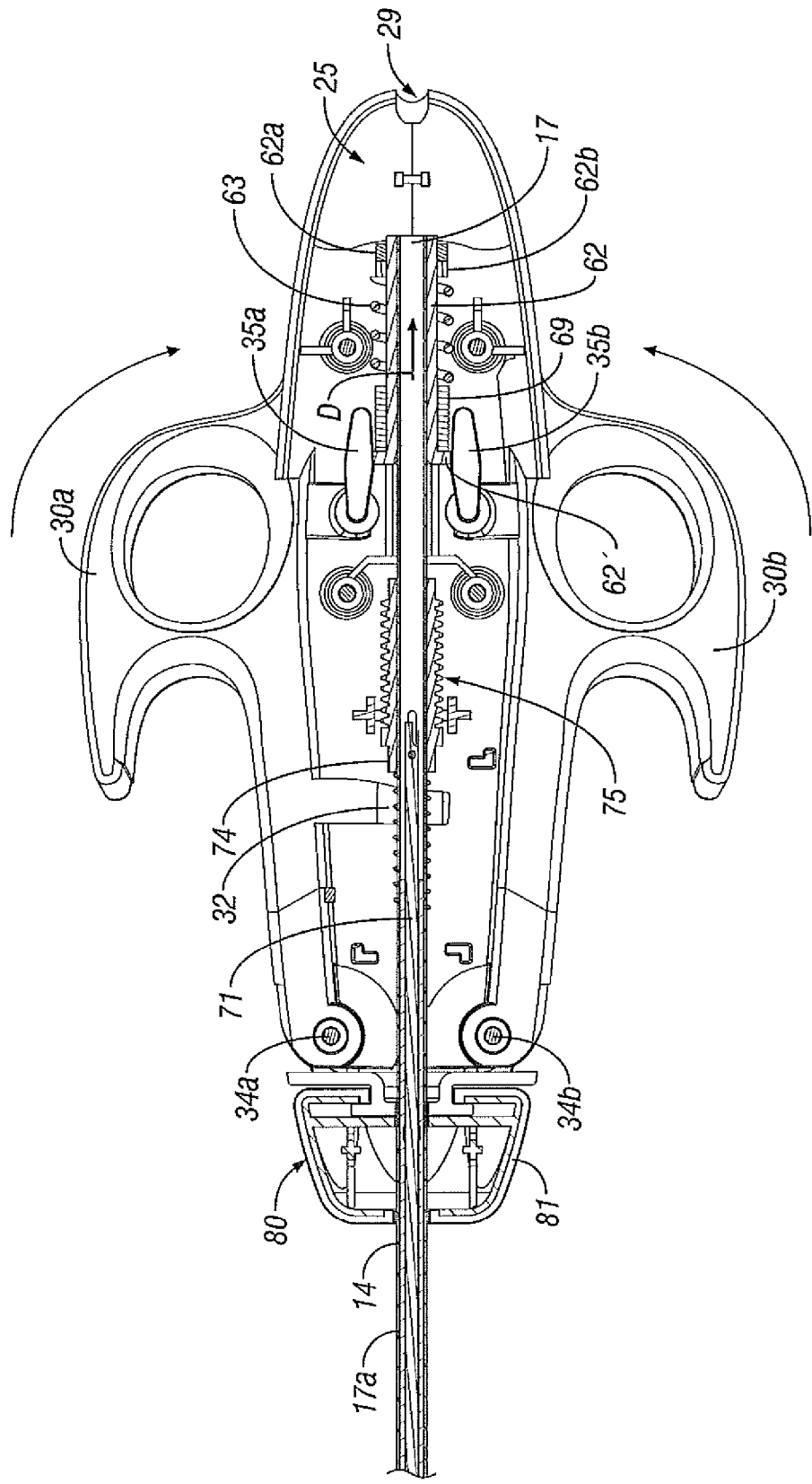
FIG. 9B is an enlarged, top view showing the handle assembly after actuation.

The handles 30a and 30b force the toggle links 35a and 35b to rotate along the longitudinal axis "A" beyond a parallel orientation with shaft 17 or longitudinal axis "A" such that, upon release, the force of spring 63 maintains the toggle links 35a and 35b in an over center or an over-extended (or past parallel) configuration thereby locking the handles 30a and 30b (and therefore the jaw members 110 and 120) relative to one another (FIG. 9B). Movement of the handles 30a and 30b away from one another (and the housing 20) unlocks and opens the handles 30a and 30b and, in turn, the jaw members 110 and 120 for subsequent grasping or re-grasping of tissue. In one embodiment, the handles 30a and 30b may be biased in an open configuration to facilitate handling and manipulation of the forceps within an operative field. Various spring-like mechanisms are contemplated which may be utilized to accomplish this purpose.

Handle 30a also includes a locking flange 32 which is disposed between the distal and proximal ends 34a' and 30a', respectively, which extends towards the housing 20 and moves relative thereto when handle 30a is actuated. Locking flange 32 includes a lockout element 32' (FIG. 14) which is dimensioned to prevent actuation of the knife assembly 70 when handle 30a is disposed in a spaced-apart or open configuration. Actuation or movement of the handle 30a towards the housing 20 disengages the lockout element 32 to allow movement of the knife assembly 70 (e.g., collar 74) to separate tissue as explained in more detail below.

Movable handles 30a and 30b are designed to provide a distinct lever-like mechanical advantage over conventional handle assemblies due to the unique position of the toggle links 35a and 35b which, when actuated, rotate along the longitudinal axis "A" to displace the actuation or drive collar 69. In other words, it is envisioned that enhanced mechanical advantage for actuating the jaw members 110 and 120 is gained by virtue of the unique position and combination of several inter-cooperating elements (i.e., opposing handles 30a, 30b, toggle links 35a, 35b and gear teeth located at the distal ends 34 and 37 of the handle members 30a, 30b, respectively) which reduce the overall user forces necessary to obtain and maintain the jaw members 110 and 120 under ideal operating pressures of about 3 kg/cm$^2$ to about 16 kg/cm$^2$. In other words, it is envisioned that the combination of these elements and their positions relative to one another enables the user to gain lever-like mechanical advantage to actuate the jaw members 110 and 120 enabling the user to close the jaw members 110 and 120 with lesser force while still generating the required forces necessary to effect a proper and effective tissue seal. The details relating to the various movements of the above-identified elements are explained below with respect to the operation of the forceps 10.

As shown best in FIGS. 3A-3D, 10A-10D and 15A-15D, the end effector assembly 100 includes opposing jaw members 110 and 120 which cooperate to effectively grasp tissue for sealing purposes. The end effector assembly 100 is designed as a bilateral assembly, i.e., both jaw members 110 and 120 pivot relative to one another about a pivot pin 185 disposed therethrough.

Figure 15A:
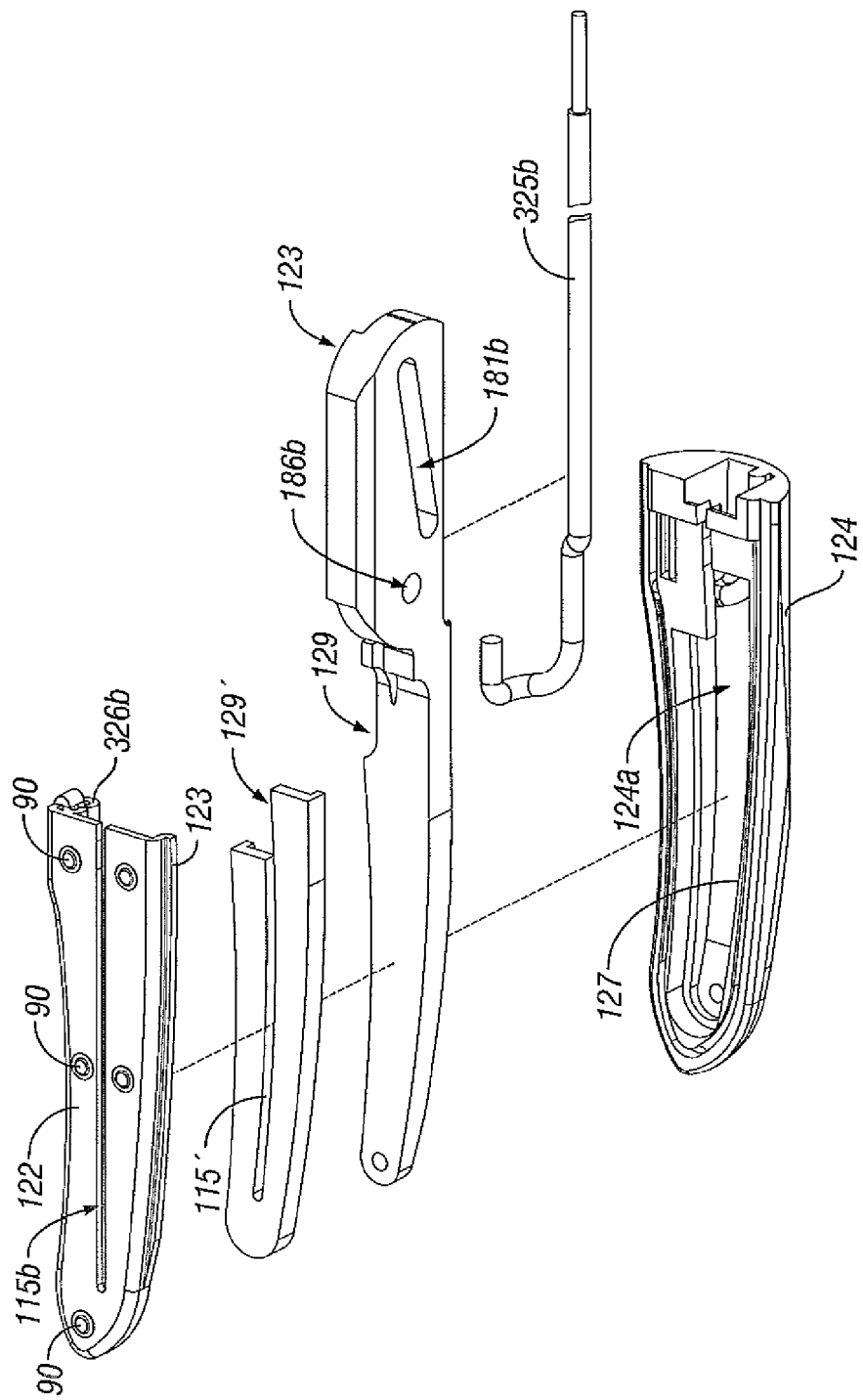
FIG. 15A is a greatly-enlarged, perspective view of the bottom jaw of the end effector assembly with parts separated.
Figure 15B:
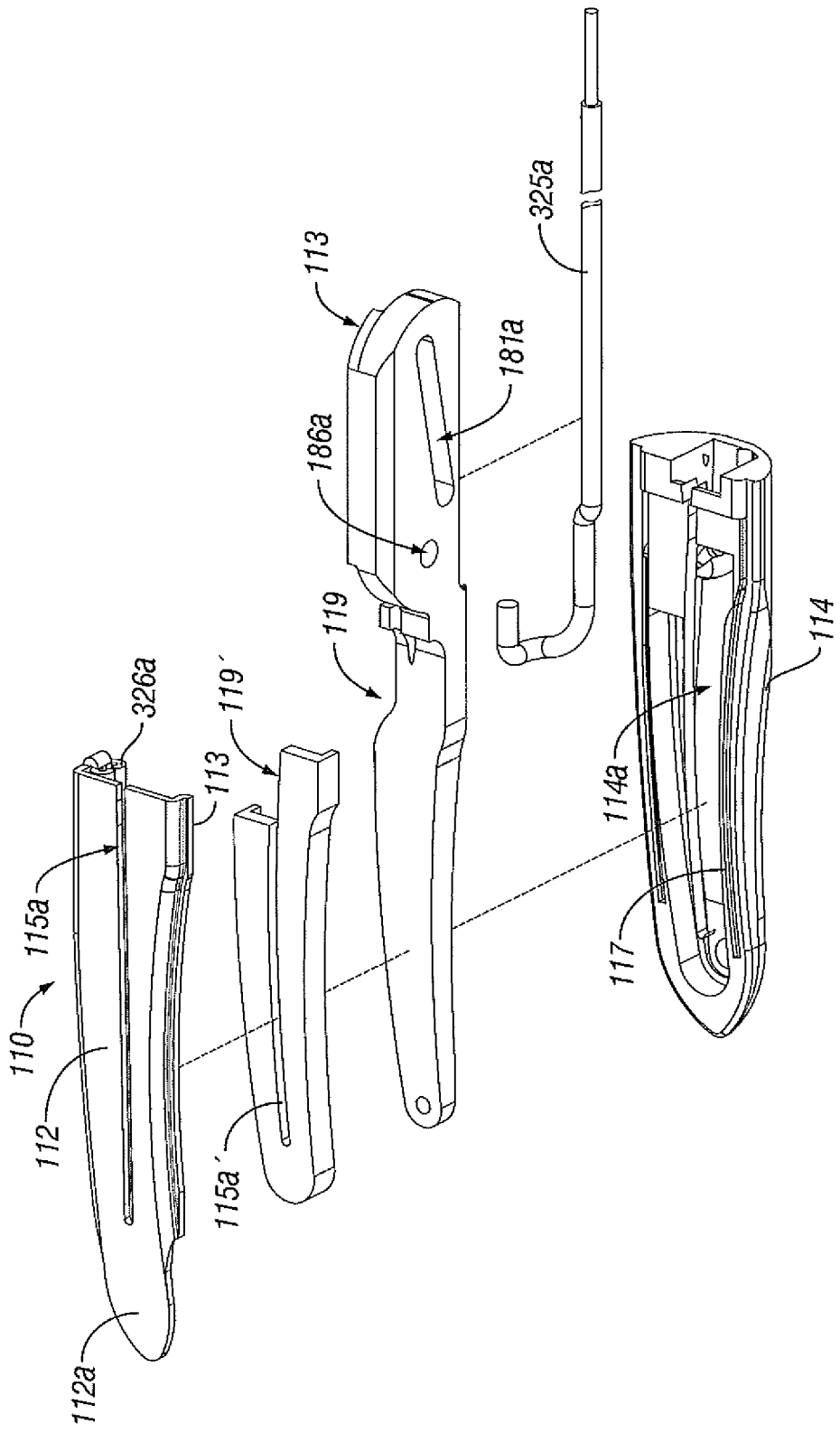
FIG. 15B is a greatly-enlarged, perspective view of the top jaw of the end effector assembly with parts separated.

A reciprocating drive sleeve 17 (See FIG. 17) is slidingly disposed within the shaft 12 and is remotely operable by the drive assembly 60 as explained in more detail below. Drive sleeve 17 includes a bifurcated distal end composed of halves 17a and 17b, respectively, which define a cavity 17' therebetween for receiving jaw members 110 and 120. More particularly and as best illustrated in FIGS. 15A and 15B, jaw members 110 and 120 include proximal flanges 113 and 123 (See FIGS. 15A and 15B), respectively, which each include an elongated angled slot 181a and 181b, respectively, defined therethrough. A drive pin 180 (See FIGS. 10A and 10B) mounts jaw members 110 and 120 to the end of a rotating shaft 18 and within cavity 17' disposed at the distal ends 17a and 17b of drive sleeve 17.

Upon actuation of the drive assembly 60, the drive sleeve 17 reciprocates which, in turn, causes the drive pin 180 to ride within slots 181a and 181b to open and close the jaw members 110 and 120 as desired. The jaw members 110 and 120, in turn, pivot about pivot pin 185 disposed through respective pivot holes 186a and 186b disposed within flanges 113 and 123. As can be appreciated, squeezing handles 30a and 30b toward the housing 20 pulls drive sleeve 17 and drive pin 180 proximally to close the jaw members 110 and 120 about tissue 420 grasped therebetween and pushing the sleeve 17 distally opens the jaw members 110 and 120 for grasping purposes.

As best shown in FIG. 15B, jaw member 110 also includes a support base 119 which extends distally from flange 113 and which is dimensioned to support an insulative plate 119' thereon. Insulative plate 119', in turn, is configured to support an electrically conductive tissue engaging surface or sealing plate 112 thereon. It is contemplated that the sealing plate 112 may be affixed atop the insulative plate 119' and support base 119 in any known manner in the art, snap-fit, over-molding, stamping, ultrasonically welded, etc. Support base 119 together with the insulative plate 119' and electrically conductive tissue engaging surface 112 are encapsulated by an outer insulative housing 114. Outer housing 114 includes a cavity 114a which is dimensioned to securely engage the electrically conductive sealing surface 112 as well as the support base 119 and insulative plate 119'. This may be accomplished by stamping, by overmolding, by overmolding a stamped electrically conductive sealing plate and/or by overmolding a metal injection molded seal plate. All of these manufacturing techniques produce jaw member 110 having an electrically conductive surface 112 which is substantially surrounded by an insulating substrate 114.

For example and as shown in FIG. 15B, the electrically conductive sealing plate 112 includes a mating portion 112a which surrounds the periphery of the sealing plate 112. Flange 112a is designed to matingly engage an inner lip 117 of the outer insulator 114. It is envisioned that lead 325a extending from circuit board 170 or generator 500 (See FIG. 16) terminates within the outer insulator 114 and is designed to electro-mechanically couple to the sealing plate 112 by virtue of a crimp-like connection 326a. For example, the insulator 119', electrically conductive sealing surface 112 and the outer, non-conductive jaw housing 114 are preferably dimensioned to limit and/or reduce many of the known undesirable effects related to tissue sealing, e.g., flashover, thermal spread and stray current dissipation.

It is envisioned that the electrically conductive sealing surface 112 may also include an outer peripheral edge which has a pre-defined radius and the outer housing 114 meets the electrically conductive sealing surface 112 along an adjoining edge of the sealing surface 112 in a generally tangential position. At the interface, the electrically conductive surface 112 is raised relative to the outer housing 114. These and other envisioned embodiments are discussed in co-pending, commonly assigned Application Ser. No. PCT/US01/11412 entitled "ELECTROSURGICAL INSTRUMENT WHICH REDUCES COLLATERAL DAMAGE TO ADJACENT TISSUE" by Johnson et al. and co-pending, commonly assigned Application Ser. No. PCT/US01/11411 entitled "ELECTROSURGICAL INSTRUMENT WHICH IS DESIGNED TO REDUCE THE INCIDENCE OF FLASH-OVER" by Johnson et al., the entire contents of both of which being hereby incorporated by reference herein.

The electrically conductive surface or sealing plate 112 and the outer housing 114, when assembled, form a longitudinally-oriented slot 115a defined therethrough for reciprocation of the knife blade 190. It is envisioned that the knife channel 115a cooperates with a corresponding knife channel 115b defined in jaw member 120 to facilitate longitudinal extension of the knife blade 190 along a preferred cutting plane to effectively and accurately separate the tissue along the formed tissue seal. As best illustrated in FIGS. 8A, 8B, 15A and 15B, knife channel 115 runs through the center of the jaw members 110 and 120, respectively, such that a blade 190 from the knife assembly 70 can cut the tissue grasped between the jaw members 110 and 120 when the jaw members 110 and 120 are in a closed position. More particularly and as mentioned above with respect to the discussion of the handle assembly 30, handle 30a includes a lockout flange which prevents actuation of the knife assembly 70 when the handle 30a is open thus preventing accidental or premature activation of the blade 190 through the tissue.

As explained above and as illustrated in FIGS. 15A and 15B, the knife channel 115 is formed when the jaw members 110 and 120 are closed. In other words, the knife channel 115 includes two knife channel halves—knife channel half 115a disposed in sealing plate 112 of jaw member 110 and knife channel half 115b disposed sealing plate 122 of jaw member 120. It is envisioned that the knife channel 115 may be configured as a straight slot with no degree of curvature which, in turn, causes the knife 190 to move through the tissue in a substantially straight fashion. Alternatively, the knife channel 115 may be dimensioned to include some degree of curvature to cause the knife 190 to move through tissue in a curved fashion. Insulating plate 119' also forms part of the knife channel 115 and includes a channel 115a' defined therein which extends along insulating plate 119' and which aligns in vertical registration with knife channel half 115a to facilitate translation of distal end 192 of the knife 190 therethrough.

The electrically conductive sealing plate 112 of jaw member 110 also includes a monopolar extension 112a which allows a surgeon to selectively coagulate tissue when disposed in a monopolar activation mode as explained in more detail below with respect to the operation of the forceps 10. Monopolar extension 112a is preferably integrally associated with conductive sealing plate 112 but may also be selectively extendible depending upon a particular purpose. The shape and dimension of the monopolar extension 112a may be dimensioned to match the overall contour of the curving contour of the jaw member 110 or the jaw housing 114. The edges of the monopolar extension 112a may be dimensioned to include radii specifically dimensioned to reduce current density along the edges thereof, e.g., smooth curves and transition points. The thickness of the monopolar extension 112a is preferably within a range of about 0.010 inches +/−0.005 inches. The width of the monopolar extension 112a is preferably about 0.084 inches +/−0.010 inches to permit the creation of an enterotomy that the jaw member(s) may pass therethrough for the purposes of mechanically spreading tissue. The length is preferably about 0.040 inches +/−0.010 inches. Commonly-owned U.S. application Ser. No. 10/970, 307 entitled "BIPOLAR FORCEPS HAVING MONOPOLAR EXTENSION" and U.S. application Ser. No. 10/988, 950 entitled "BIPOLAR FORCEPS HAVING MONOPOLAR EXTENSION" disclose various embodiments of a monopolar extension which may be configured for use with forceps 10 of the present disclosure. The entire contents of both of these applications are hereby incorporated by reference herein.

Jaw member 120 includes similar elements to jaw member 110 such as jaw housing 124 which encapsulates a support plate 129, an insulator plate 129' and an electrically conductive sealing surface 122. Likewise, the electrically conductive surface 122 and the insulator plate 129', when assembled, include respective longitudinally-oriented knife channels 115a and 115a' defined therethrough for reciprocation of the knife blade 190. As mentioned above, when the jaw members 110 and 120 are closed about tissue, knife channels 115a and 115b form a complete knife channel 115 to allow longitudinal extension of the knife 190 in a distal fashion to sever tissue along a tissue seal. It is also envisioned that the knife channel 115 may be completely disposed in one of the two jaw members, e.g., jaw member 120, depending upon a particular purpose. It is also envisioned that jaw member 120 may be assembled in a similar manner as described above with respect to jaw member 110.

As best seen in FIG. 15A, jaw member 120 includes a series of stop members 90 disposed on the inner facing surface of the electrically conductive sealing surface 122 to facilitate gripping and manipulation of tissue and to define a gap "G" (FIG. 10B) between opposing jaw members 110 and 120 during sealing and cutting of tissue. It is envisioned that the series of stop members 90 may be employed on one or both jaw members 110 and 120 depending upon a particular purpose or to achieve a desired result. A detailed discussion of these and other envisioned stop members 90 as well as various manufacturing and assembling processes for attaching and/or affixing the stop members 90 to the electrically conductive sealing surfaces 112, 122 are described in commonly-assigned, co-pending U.S. Application Ser. No. PCT/US01/ 11413 entitled "VESSEL SEALER AND DIVIDER WITH NON-CONDUCTIVE STOP MEMBERS" by Dycus et al. which is hereby incorporated by reference in its entirety herein.

Jaw member 120 is connected to a second electrical lead 325b extending from circuit board 170 or generator 500 (See FIG. 16) which terminates within the outer insulator 124 and is designed to electro-mechanically couple to the sealing plate 122 by virtue of a crimp-like connection 326b. As explained in more detail below, leads 325a and 325b allow a user to selectively supply either bipolar or monopolar electrosurgical energy to the jaw members 110 and 120 as needed during surgery.

Jaw members 110 and 120 are electrically isolated from one another such that electrosurgical energy can be effectively transferred through the tissue to form a tissue seal. For example and as best illustrated in FIGS. 15A and 15B, each jaw member, e.g., 110, includes a uniquely-designed electrosurgical cable path disposed therethrough which transmits electrosurgical energy to the electrically conductive sealing surface 112. Cable lead 325a is held loosely but securely along the cable path to permit rotation of the jaw members 110 and 120. As can be appreciated, this isolates electrically conductive sealing surface 112 from the remaining operative components of the end effector assembly 100, jaw member 120 and shaft 12. The two electrical potentials are isolated from one another by virtue of the insulative sheathing surrounding the cable leads 325a and 325b.

Figure 12:
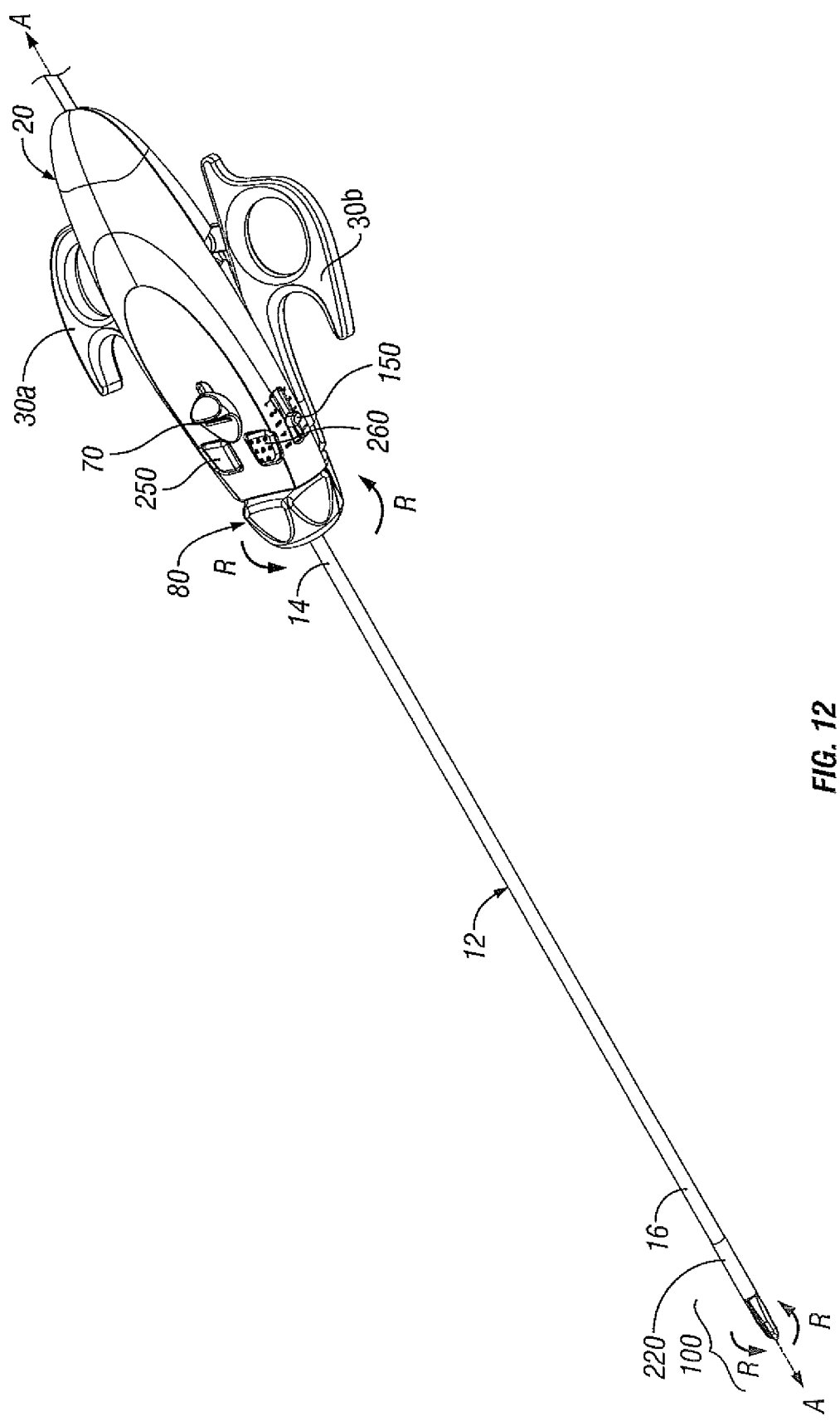
FIG. 12 is top, perspective view of the forceps of FIG. 1B showing rotation of the end effector assembly.
Figure 17:
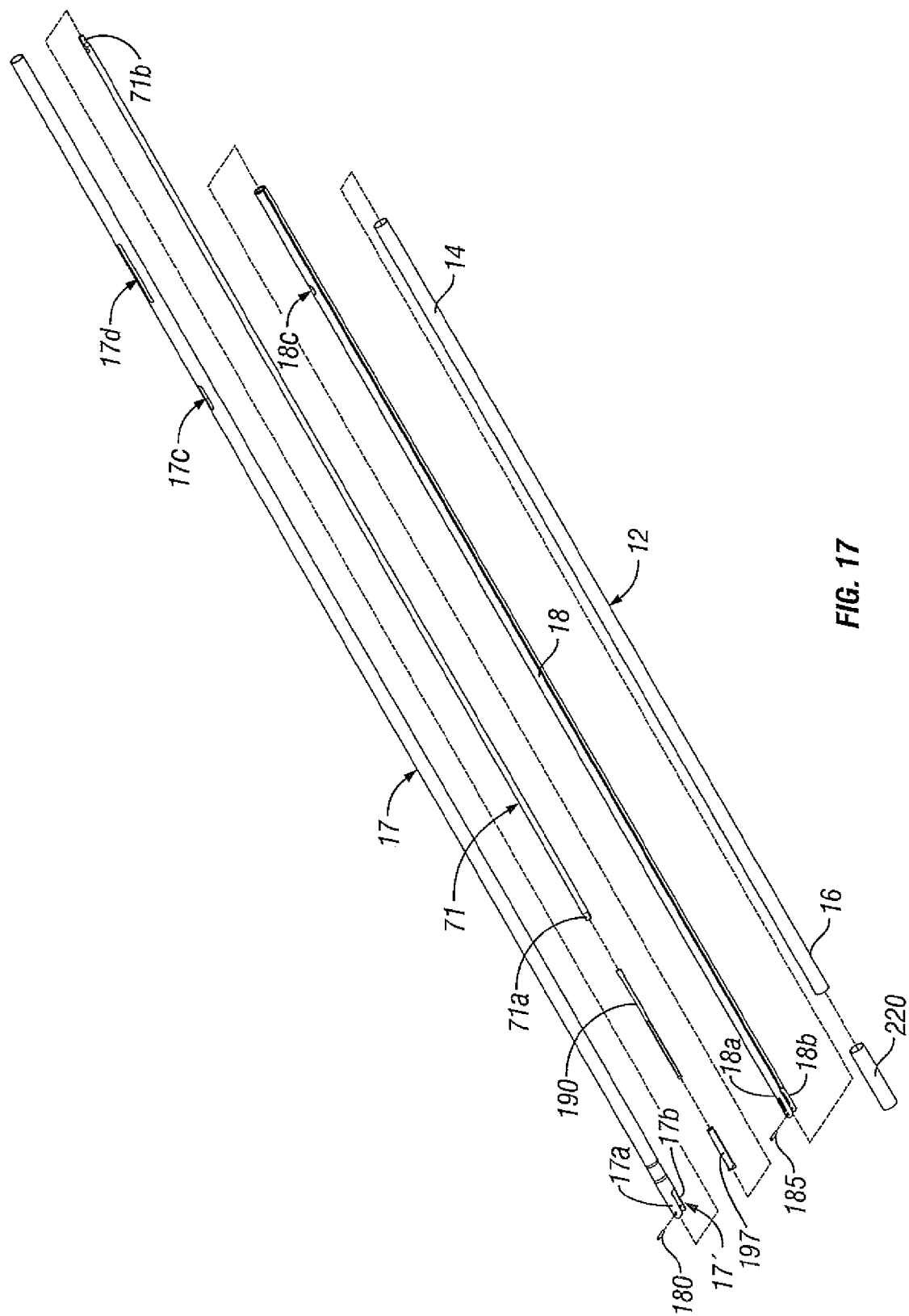
FIG. 17 is a greatly-enlarged, perspective view of the elongated shaft for housing various moving parts of the drive assembly and knife assembly.

As mentioned above, jaw members 110 and 120 are engaged to the end of rotating shaft 18 by pivot pin 185 such that rotation the rotating assembly 80 correspondingly rotates shaft 18 (along with sleeve 17 and knife drive rod 71) which, in turn, rotates end effector assembly 100 (See FIG. 12). More particularly, the distal end of rotating shaft 18 is bifurcated to include ends 18a and 18b which define a channel therein for receiving jaw members 110 and 120. Pivot pin 185 secures the jaw members 110 and 120 to ends 18a and 18b through aperture 186a and 186b defined through jaw members 110 and 120, respectively. As best seen in FIGS. 13 and 17, rotating shaft 18 is dimensioned to slidingly receive knife drive rod 71, knife 190 and a knife guide 197 therein. Rotating shaft 18, in turn, is rotatingly received within drive sleeve 17 which as mentioned above connects to the drive assembly 60. The details with respect to the knife assembly are explained in more detail with respect to FIGS. 5A, 5B, 6A, 6B, 7, 8A and 8B.

Rotating shaft 18 and drive shaft 17 are fixed to the rotating assembly 80 by two rotating tabs which are engaged through slot 18c in the rotating shaft 18 such that rotating of the rotating member correspondingly rotates the rotating shaft 18. It is envisioned that the drive shaft and the rotating shaft may be affixed to the rotating assembly in other ways known in the art, snap-fit, friction fit, etc.

FIGS. 13 and 14 show the details of the forceps 10 and the component features thereof, namely, the housing 20, the drive assembly 60, the rotating assembly 80, the knife assembly 70 and the handle assembly 30. More particularly, FIG. 13 shows the entire forceps 10 along with the above-identified assemblies and components thereof in an exploded condition and FIG. 14 shows an exploded view of the housing 20 and the components contained therein.

Housing 20 includes housing halves 20a and 20b which, when mated, form housing 20. As can be appreciated, housing 20, once formed, forms an internal cavity 25 which houses the various assemblies identified above which will enable a user to selectively manipulate, grasp, seal and sever tissue in a simple, effective, and efficient manner. Each half of the housing, e.g., half 20b, includes a series of mechanical interfacing components, e.g., 205 which align and/or mate with a corresponding series of mechanical interfaces (not shown) to align the two housing halves 20a and 20b about the inner components and assemblies. The housing halves 20a and 20b may then be sonic welded or otherwise matingly engaged to secure the housing halves 20a and 20b once assembled.

As mentioned above, the handle assembly 30 includes two movable handles 30a and 30b which each cooperate with a toggle link 35a and 35b, respectively, to actuate the actuating or drive collar 69 of the drive assembly 60. The drive collar, in turn, reciprocates drive sleeve 17 to open and close the jaw members 110 and 120 as described above. Movable handles 30a and 30b are designed to provide a distinct lever-like mechanical advantage over conventional handle assemblies due to the unique position of the toggle links 35a and 35b which, when actuated, rotate along the longitudinal axis "A" to displace the actuation collar 69. More particularly and as mentioned above, it is envisioned that enhanced lever-like mechanical advantage for actuating the jaw members 110 and 120 is gained by virtue of the unique position and combination of various inter-cooperating elements such as the toggle links 35a and 35b and the gear teeth 34a and 34b at the distal end of the handles 30a and 30b which cooperate to reduce the overall user forces necessary to obtain and maintain the jaw members under ideal operating pressures of about 3 kg/cm² to about 16 kg/cm².

As mentioned above, movement of the handles 30a and 30b from an open or spaced apart configuration to a closed position towards the housing 20 forces the actuating collar 69 proximally against spring 63 which, in turn, translates drive sleeve 17 proximally to close the jaw members 110 and 120. Moreover, as the handles 30a and 30b rotate to a closed position, the handles 30a and 30b force the toggle links 35a and 35b to rotate along the longitudinal axis "A" beyond a parallel orientation with longitudinal axis "A" such that upon release of the handles 30a and 30b from a closed position, the force of spring 63 maintains the toggle links 35a and 35b in an over-extended/over-centered (i.e., past parallel) configuration thereby locking the handles 30a and 30b (and therefore the jaw members 110 and 120) relative to one another (See FIGS. 9A and 9B). To unlock the jaw members 110 and 120, the handles 30a and 30b are moved away from one another (and the housing 20) to return the toggle links 35a and 35b to at least a parallel orientation with respect to longitudinal axis "A" which unlocks and opens the handles 30a and 30b and, in turn, the jaw members 110 and 120 for subsequent grasping or re-grasping of tissue. Once the handles 30a and 30b are opened past parallel the force of spring 63 facilitates opening of the handles 30a and 30b and the jaw members 110 and 120.

As mentioned above, handle 30a also includes a locking flange 32 which is dimensioned to prevent actuation of the knife assembly 70 when handle 30a is disposed in a spaced-apart or open configuration. Actuation or movement of the handle 30a towards the housing 20 disengages the lockout element 32 to allow movement of the knife assembly 70 to separate tissue as explained in more detail below.

As best seen in FIG. 14, the drive assembly includes drive collar 69, spring 63 and locking sleeve 62. Toggle links 35a and 35b operatively connect the drive collar 69 to the handles 30a and 30b, respectively. The locking sleeve 62 is dimensioned to fit through an opening 67 defined through the drive collar 69 and the spring 63 is dimensioned to fit over the locking sleeve 62. The spring 63, in turn, is biased between and against the drive collar 69 and a pair of locking bolts 62a and 62b which to the locking sleeve 62. Upon actuation of the handles 30a and 30b, the toggle links 35a and 35b force the drive collar 69 proximally to compress the spring 63 against the locking bolts 62a and 62b.

As best seen in FIGS. 9A and 9B, the locking sleeve 62 and sleeve 17 are clamped or welded together at assembly. Locking sleeve 62 includes a distal collar 62' which abuts drive collar 69 to ensure axial translation of the driving collar 69 upon actuation of the handles 30a and 30b. Locking sleeve 62 and sleeve 17 are also dimensioned to reciprocate through locking nuts 62a and 62b during actuation of handles 30a and 30b which enables the spring 63 to compress against locking nuts 62a and 62b which as mentioned above, facilitates locking the forceps 10 in a closed orientation within desired force ranges and facilitates opening of the handles 30a and 30b after activation of the forceps 10.

FIG. 14 also shows the rotating assembly 80 which includes two C-shaped rotating halves 81a and 81b which, when assembled about shaft 17, form a generally circular rotating member 81. More particularly, each rotating half, e.g., 81b, includes a series of mechanical interfaces 83 which matingly engage a corresponding series of mechanical interfaces (not shown) in half 81a to form rotating member 81. Half 81b also includes a tab or protrusion (Not shown) which together with a corresponding tab or protrusion (not shown) disposed on half 81a cooperate to matingly engage slots 17c and 18c on the drive shaft 17 and rotating shaft 18, respectively. As can be appreciated, this permits selective rotation of the end effector assembly 100 about axis "A" by manipulating the rotating member 80 in the direction of the arrow "R" (see FIGS. 1A and 12).

As mentioned above, the jaw members 110 and 120 may be opened, closed and rotated to manipulate tissue until sealing is desired. This enables the user to position and re-position the forceps 10 prior to activation and sealing. It is envisioned that the unique feed path of the cable leads 325a and 325b through the rotating assembly 80, along shaft 18 and, ultimately, to jaw members 110 and 120 enables the user to rotate the end effector assembly 100 about 170 degrees in both the clockwise and counterclockwise direction without tangling or causing undue strain on cable leads 325a and 325b.

Figure 11A:
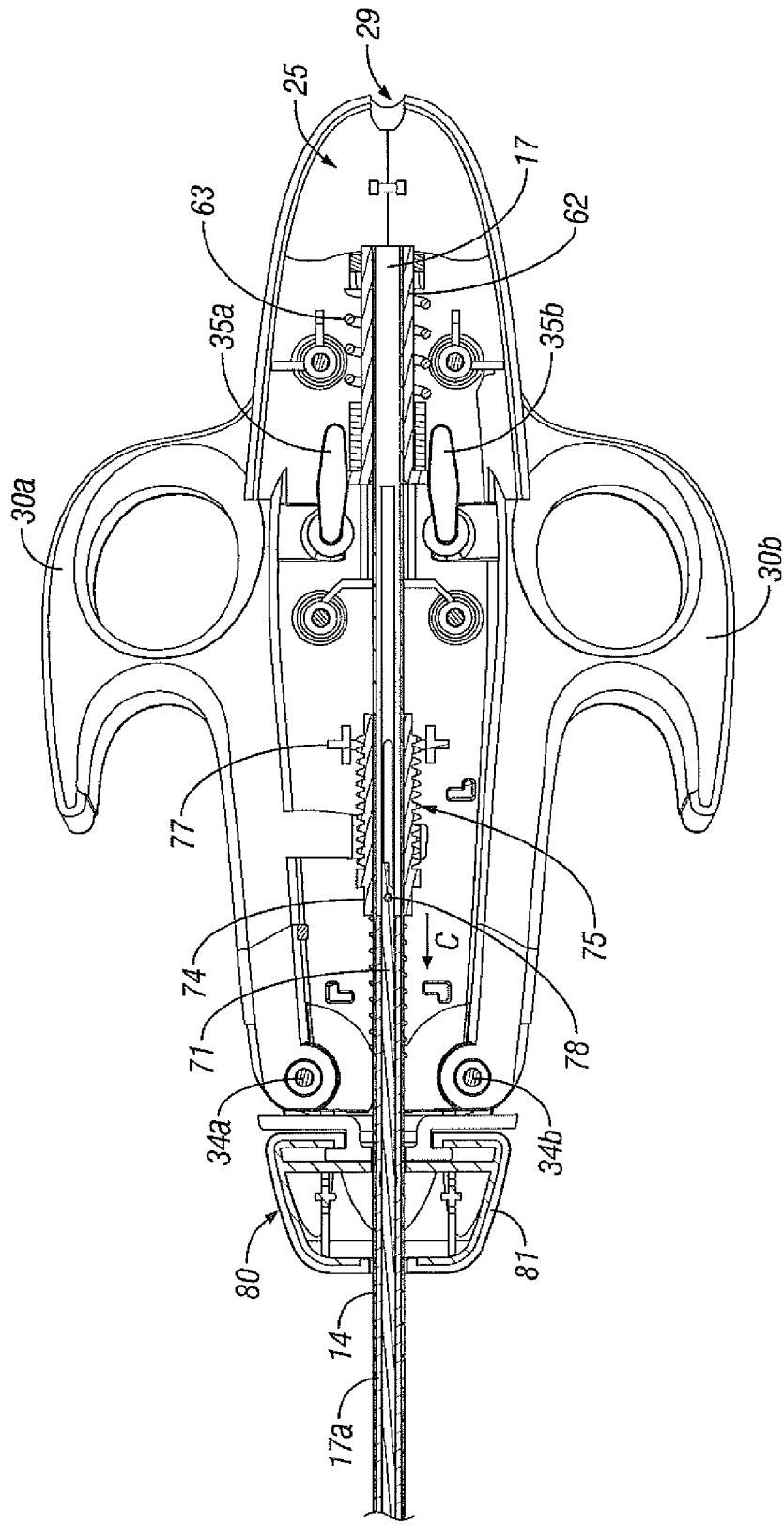
FIG. 11A is an enlarged, top view similar to FIG. 9B showing the knife actuator after actuation.
Figure 11B:
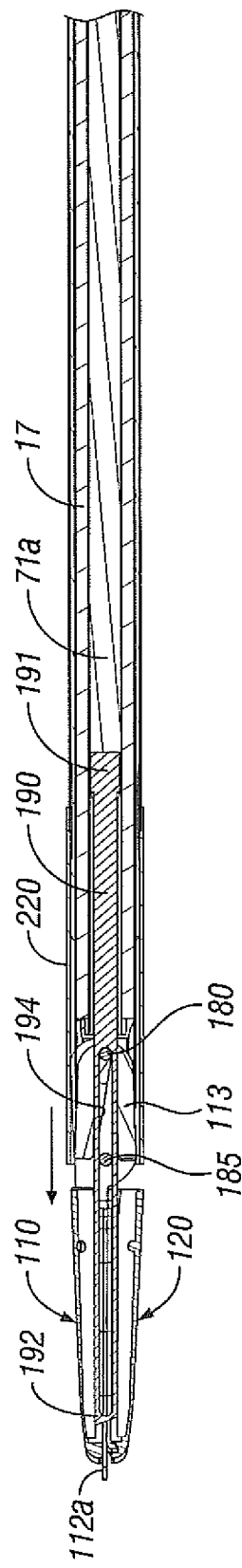
FIG. 11B is a greatly-enlarged, side cross sectional view of the end effector assembly showing the position of the knife after actuation.

As best shown in FIGS. 5A, 5B, 6A, 6B, 7, 11A, 11B and 14, the knife assembly 70 mounts atop housing 20 and is configured to selectively translate a knife bar 71 which, in turn, translates knife 190 through tissue. More particularly, the knife assembly 70 includes a finger actuator 76 having an elongated support base 72 affixed thereto which is selectively moveable parallel to longitudinal axis "A". Elongated support base 72 includes a proximal end which is configured as a gear rack having a series of gear teeth 72a which depend downwardly therefrom. Gear teeth 72a are configured to mesh with a corresponding pinion gear 77 mounted for rotation on the housing 20. The pinion gear 77 also meshes with a second gear track 75 having a plurality of gear teeth 75a disposed on a collar 74 which is slidingly translatable atop sleeve 17. As best shown in FIGS. 9A, 9B and 11A, a pin 78 attaches the collar 74 to a proximal end 71b of knife bar 71 through slot 17d defined through sleeve 17. Proximal translation of the finger actuator 76 in the direction "F" rotates the pinion gear 77 in a clockwise direction which, in turn, forces the second gear track 75a distally in the direction "H" (see FIG. 7). A spring 79 biases the collar 74 against the housing 20 to automatically return the knife assembly 70 to a pre-firing position after the finger actuator 76 is released.

The knife assembly may be configure to include a mechanical fuse to prevent excessive actuation of the knife assembly. For example, pinion gear 77 may be configured to include one or more frangible or break-away elements to prevent over extension of the finger actuator in the proximal direction. As can be appreciated, configuring the pinion gear 77 in this fashion will prevent the user from overloading and damaging the delicate knife blade 190 disposed between the jaw members 110 and 120. In one embodiment, the axle of the pinion gear 77 will fracture when an excessive force of about 9 lbf or greater is applied in the direction "F" (as shown in FIG. 7). In this instance and upon fracture of the pinion axle, the spring 79 automatically returns the knife blade 190 to a retracted position to allow the separation of the jaw members 110 and 120 which allows the forceps 10 to be safely removed from the body without damaging tissue. As can be appreciated, the fracture of the pinion axle does not contaminate the surgical field and the fractured gear 77 remains within the housing 20 of the forceps 10. In addition, it is envisioned that the internal operating components of the housing 20 may be accessible in this instance to allow replacement of the pinion gear.

It is also contemplated that other elements may be configured in a similar fashion to limit overloading of the instrument and damaging delicate parts associated with the forceps 10. For example, the teeth 72a on the rack could be dimensioned to fracture upon excessive force or the track 75a may fracture as well. Moreover, the handles 30a and 30b may be equipped with a similar overloading safety mechanism which prevents over compression of the handles 30a and 30b and the drive assembly 60 or handle assembly 30. For example, links 35a and 35b may be configured to fracture upon an overloading condition or drive collar 69.

As mentioned above, the knife assembly 70 is prevented from being actuated when the jaw members 110 and 120 are opened by virtue of flange 32 disposed on handle 30a being positioned to prevent distal activation of the collar 74 when handles 30a and 30b are opened. Upon movement of the handles 30a and 30b to a closed position, the flange 32 is positioned to allow distal translation of collar 74 to actuate the knife bar 71.

The operating features and relative movements of the internal working components of the forceps 10 are shown by phantom representation in the various figures. As the handles 30a and 30b are squeezed, the drive collar 69, through the mechanical advantage of the in-line toggle links 35a and 35b, is moved proximally which, in turn, compresses a spring 63 against the locking nuts 62a and 62b. As a result thereof, the drive collar 69 reciprocates locking sleeve 62 proximally which, in turn, reciprocates drive sleeve 17 proximally to closes jaw members 110 and 120. Once the jaw members 110 and 120 are closed about tissue the user can selectively energize the electrically conductive sealing plates for either monopolar activation or bipolar activation to treat tissue.

Figure 6A:
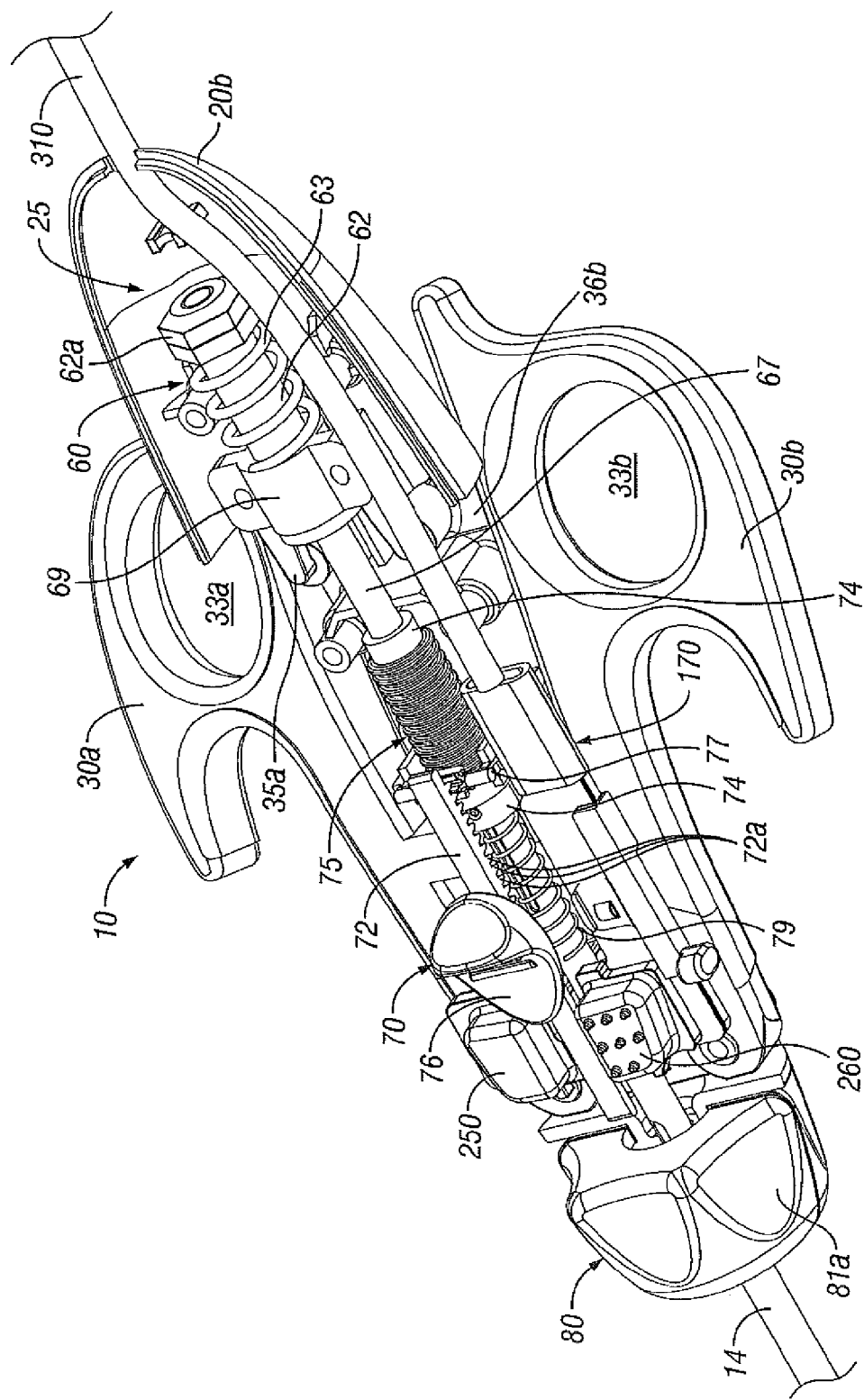
FIG. 6A is an enlarged perspective view of the internal working components of the forceps of FIG. 1B showing a knife actuator in an un-actuated position.
Figure 6B:
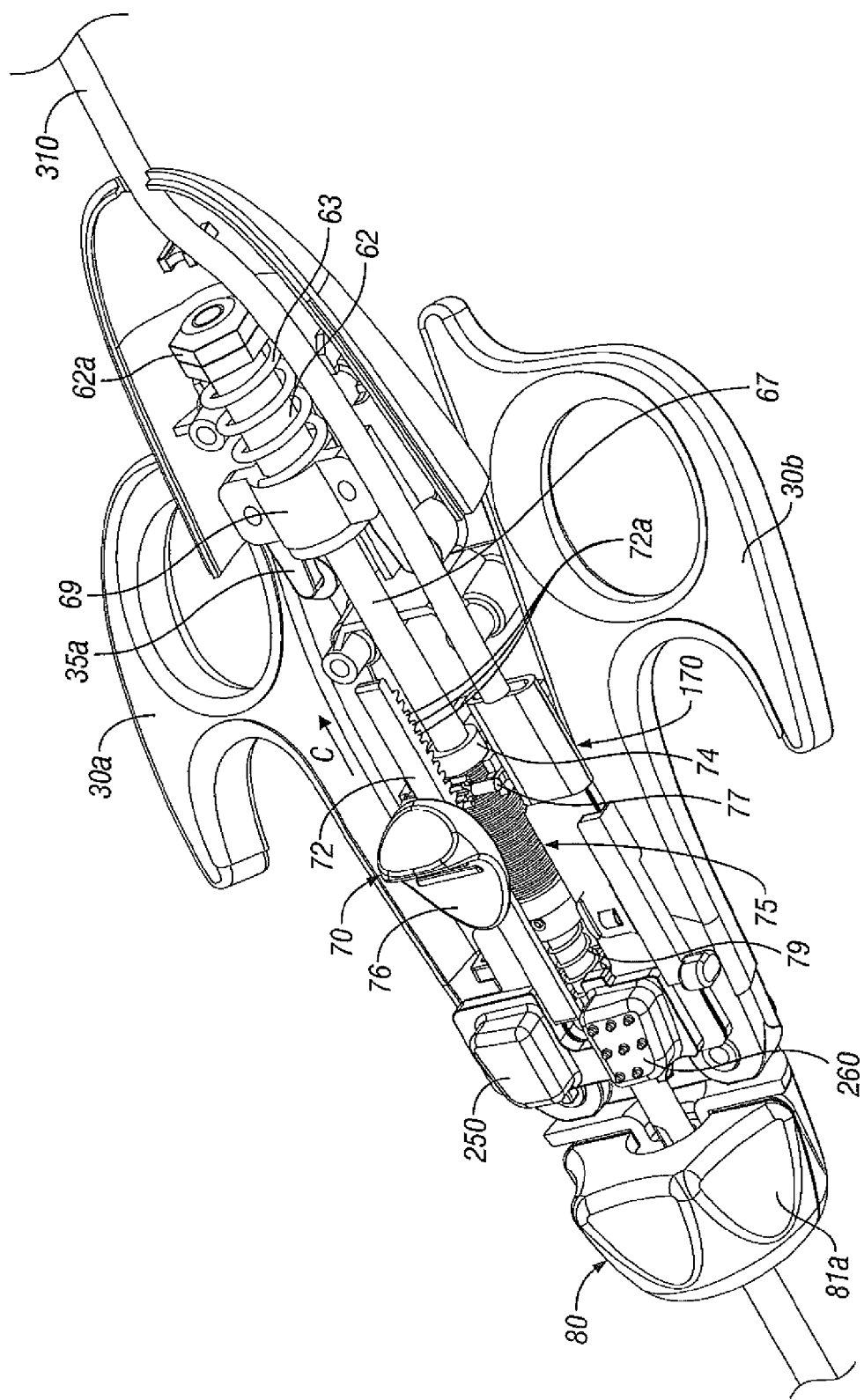
FIG. 6B is an enlarged perspective view of the internal working components of the forceps of FIG. 1B showing a knife actuator being actuated.

As best shown in FIGS. 6A, 14 and 16, the forceps 10 includes two switches 250 and 260 which are mounted within or atop the housing 20 and which allow a user to selectively activate the forceps 10 to selectively transmit bipolar energy to the jaw members 110 and 120 or selectively transmit monopolar energy to the jaw members 110 and 120 or to a single jaw member, e.g., jaw member 110. For the purposes herein, it is envisioned that either switch, e.g., switch 250, may be configured for monopolar activation and the other switch, e.g., switch 260, may be configured for bipolar activation. Further the switches 250 and 260 may include indicia or other identifying elements, e.g., raised protuberances, scallops, different shapes, etc., to distinguish the two switches 250 and 260 from one another which may prove especially useful during wet operating conditions.

In one particularly useful embodiment and as best shown in FIG. 6A, switches 250 and 260 are mounted within the housing 20 on opposite sides of longitudinal axis "A" and on opposite sides of the knife assembly 70. As can be appreciated, the knife assembly 70 (and actuation thereof) and the switches 250 and 260 (and the activation thereof) are conveniently located to facilitate actuation/activation by the user during operating conditions. For example, it is contemplated that the user may utilize the same finger to both activate the switches 250 and 260 to treat tissue and actuate the knife assembly 70 to cut tissue once treated.

As shown in FIGS. 6A and 16, cable 310 is fed through the housing 20b on one side of the drive assembly 60 and electromechanically connects to a printed circuit board 172 of the switch assembly 170. More particularly, cable 310 is internally divided into a plurality of leads 311a-311f which are secured by a crimp-like connector 174 to a series of corresponding contacts 176a-176f extending from the printed circuit board 172 or to other electrically conductive leads which ultimately connect to the jaw members. Other electromechanical connections are also envisioned which are commonly known in the art, e.g., IDC connections, soldering, etc. It is envisioned the various leads 311a-311f are configured to transmit different electrical potentials or control signals to the printed circuit board 172 which, in conjunction with generator 500, regulates, monitors and controls the electrical energy to the jaw members 110 and 120. As mentioned above with respect to the description of the jaw members, electrical leads 325a and 325b extend through the rotating member 80, along shaft 18 to ultimately connect to the jaw members 110 and 120.

Figure 23:
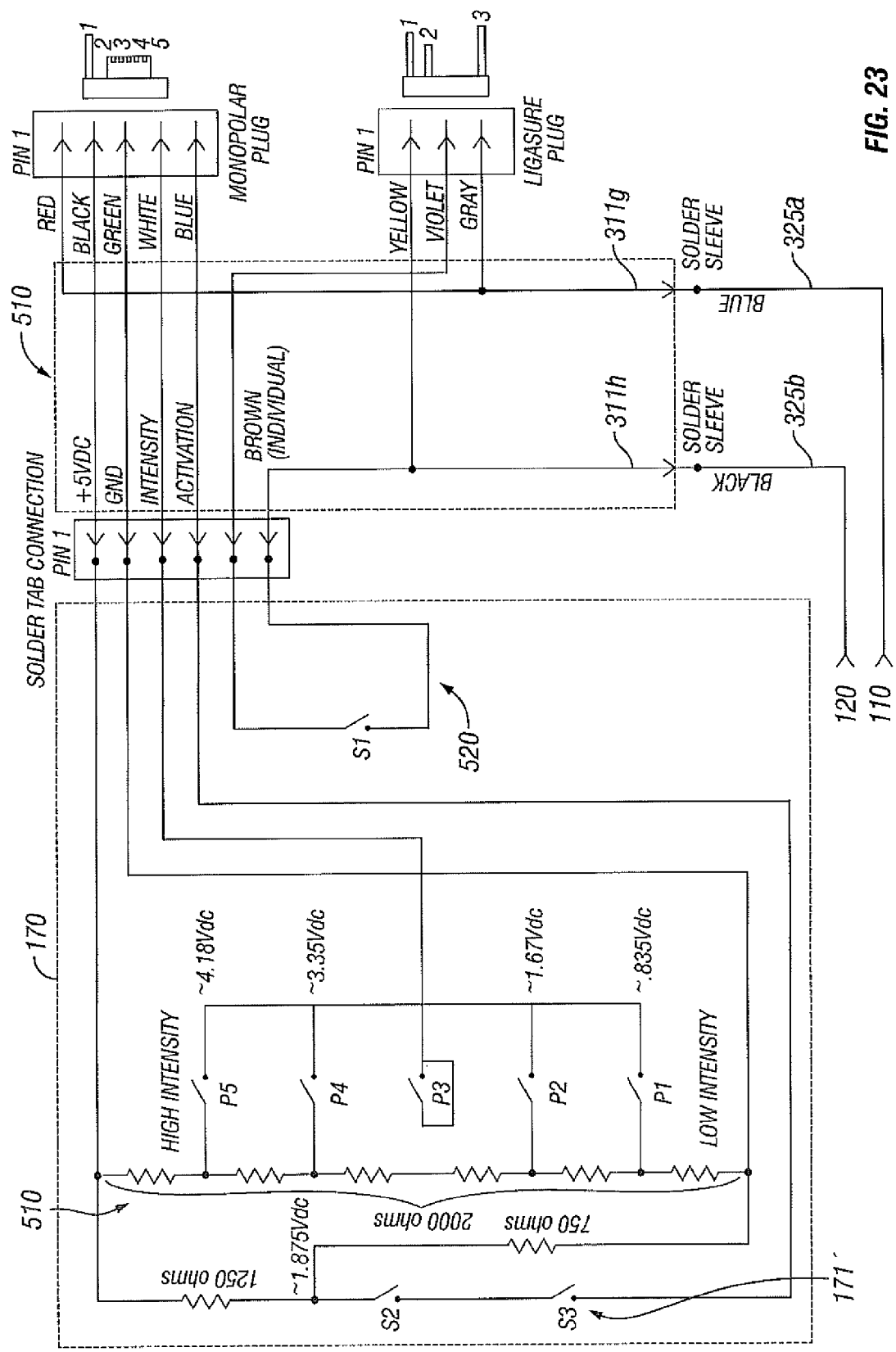
FIG. 23 is a schematic electrical diagram of the electrical switching assembly.
Figure 24:
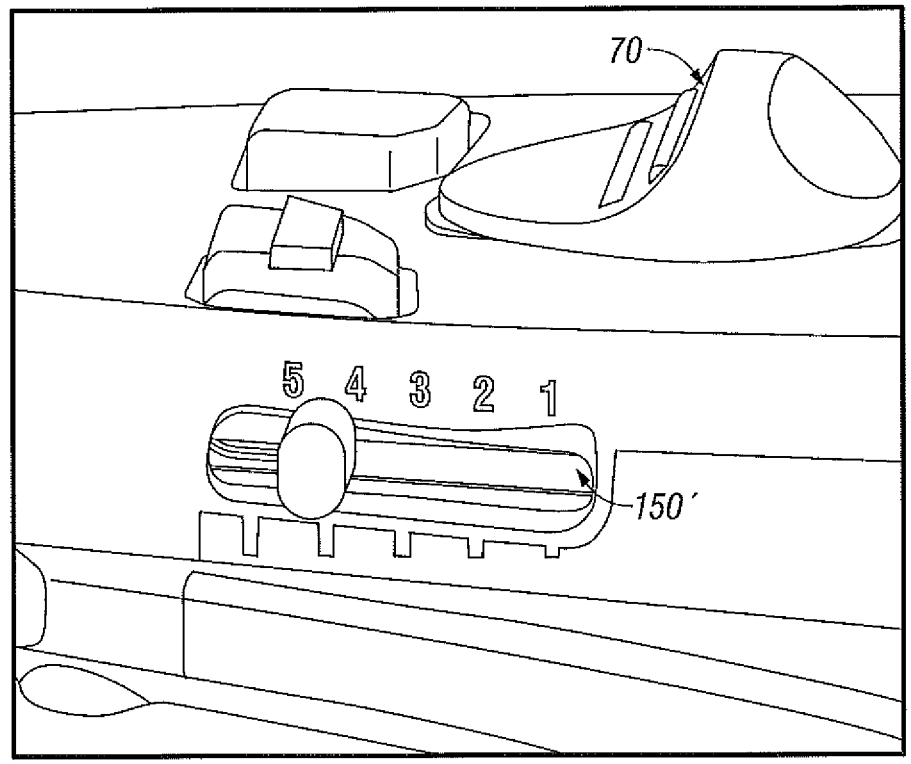
FIG. 24 is a computer simulation showing the movement of the an intensity control on the switching assembly.
Figure 25:
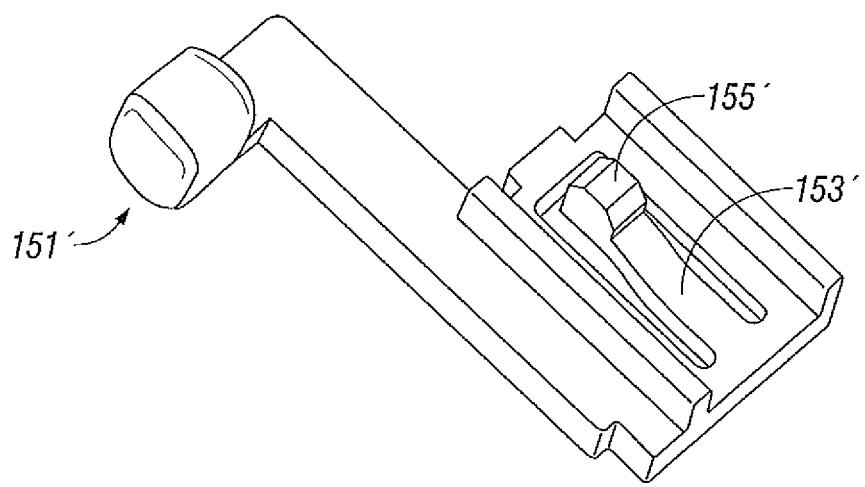
FIG. 25 is an enlarged view of the intensity control actuator.
Figure 26:
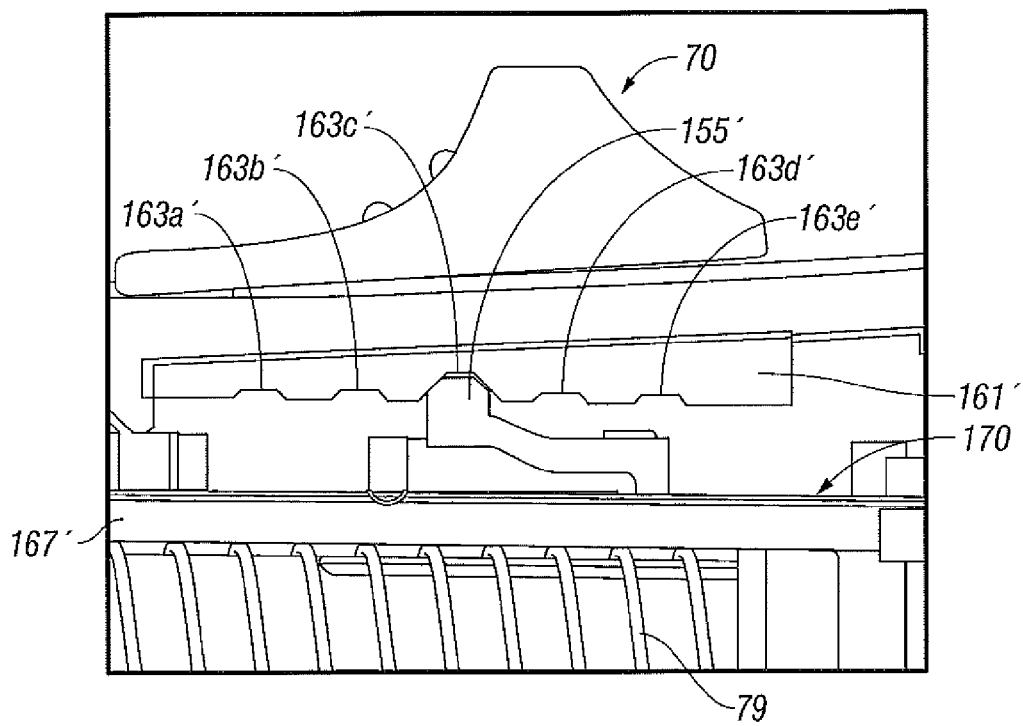
FIG. 26 is a computer-simulated, enlarged internal view of the intensity control actuator mechanically engaged within a detent track disposed in the housing.

FIG. 23 shows a schematic representation of a control circuit 510 for use with the presently disclosed forceps 10. As mentioned above, forceps 10 is configured to operate in two independent modes of operation—bipolar mode and monopolar mode for different surgical procedures. When one of the switches 250 (S1 in FIG. 19 and 23) or 260 (S2 in FIGS. 19 and 23) of switch assembly 170 is depressed, a contact (not shown) on the switches 250 and 260 activates the appropriate electrical potential (or potentials) to the jaw members 110 and 120 which is (are) carried through leads 325a and/or 325b. For example, if switch 250 (LigaSure™ activation) is depressed, the circuit board 172 signals the generator 500 to configures the forceps 10 as a bipolar forceps and lead 325a carries a first electrical potential to jaw member 110 and lead 325b carries a second electrical potential to jaw member 120. As such the jaw members 110 and 120 conduct bipolar energy through the tissue upon activation to create a tissue seal. FIG. 23 shows one example of contemplated electrical circuitry which may be utilized to accomplish this purpose.

If switch 260 (monopolar activation) is depressed, the circuit board 172 configures the forceps as a monopolar forceps and lead 325a caries a first electrical potential to jaw member 110 to coagulate or otherwise treat tissue in a monopolar fashion. As mentioned above, jaw member 110 includes a monopolar extension which facilitates monopolar treatment of various tissue types, e.g., avascular tissue structures, and/or allows quick dissection of narrow tissue planes. Activation of the monopolar extension may be controlled by an activation circuit which allows the user to selectively apply monopolar energy or bipolar energy as needed during surgery. One envisioned activation circuit is disclosed in commonly-owned U.S. patent application Ser. No. 10/970,307 entitled "BIPOLAR FORCEPS HAVING MONOPOLAR EXTENSION" and U.S. application Ser. No. 10/988,950 entitled "BIPOLAR FORCEPS HAVING MONOPOLAR EXTENSION", the entire contents of both of these applications being hereby incorporated by reference herein.

Alternatively and as best shown in FIG. 23, during the monopolar mode when switch 260 is depressed, the generator (or the printed circuit board) can direct both leads 325a and 325b to carry the same electrical potential to jaw members 110 and 120 depending upon a particular purpose or depending upon a desired surgical treatment, e.g., so-called "coagulative painting". As can be appreciated, in a monopolar mode, a return pad would be necessarily placed in contact with the patient to act as a return path (not shown) for the electrical energy. The return pad in this instance would connect to the generator 500 directly or though a return pad control mechanism (not shown) which may be configured to monitor certain parameters of the return pad. Various envisioned control systems are disclosed in commonly-owned U.S. patent application Ser. No. 10/918,984 entitled "MULTIPLE RF RETURN CABLE PAD CONTACT DETECTION SYSTEM", U.S. patent application Ser. No. 09/310,059 entitled "ELECTROSURGICAL RETURN ELECTRODE MONITOR" (now U.S. Pat. No. 6,258,085), U.S. Provisional Patent Application Ser. No. 60/616,970 entitled "DEVICE FOR DETECTING HEATING UNDER A PATIENT RETURN ELECTRODE" and U.S. Provisional Patent Application Ser. No. 60/666,798 entitled "TEMPERATURE REGULATING PATIENT RETURN ELECTRODE AND RETURN ELECTRODE MONITORING SYSTEM", the entire contents of all of which are incorporated by reference wherein.

In a bipolar mode, the circuit 510 (schematically-illustrated in FIG. 23) electrical routes energy to the two jaw members 110 and 120. More particularly, when switch 250 is depressed an isolated circuit 520 of the circuit 510 recognizes a resistance drop thereacross which is recognized by the generator to initiate electrosurgical energy to supply a first electrical potential to jaw member 110 and a second electrical potential to jaw member 120. Switch 520 acts as an insolated control circuit and is protected by circuitry within the generator from the higher current loop which supplies electrical energy to the jaw members 110 and 120. This reduces the chances of electrical failure of the switch 260 due to high current loads during activation.

As best shown in FIG. 14, handle 30a also includes a switch lockout mechanism 255 which may be configured to prevent activation of one or both switches 250 and 260 when the jaw members 110 and 120 are disposed in an open configuration. More particularly, lockout mechanism 255 extends from handle 30a towards housing 20 and is selectively moveable with the handle 30a from a first position wherein the lockout mechanism 255 prevents one or both switches 250 and 260 from being depressed to contact the circuit board 172 to a second position closer to the housing 20 wherein the lockout mechanism 255 is positioned to allow activation of switch 250 (or switches 250 and 260). It is envisioned that the lockout mechanism 255 may be configured as a purely mechanical lockout which physically prevents movement of one or both switches 250 and/or 260 or may be configured as an electromechanical lockout which includes a mechanical element which activates a safety switch to allow activation. Moreover, the switch lockout mechanism 255 may be configured such that one or both switches may be independently and exclusively activatable, i.e., only one switch may be activated at a time.

For example, flex circuit 170 may include a safety switch 171 which is activated when lockout mechanism 255 physically engages safety switch 171 to close the circuit to permit electrosurgical activation. In other words, the safety switch 171 is deflected or physically engaged (i.e., by virtue of the movement of lockout mechanism 255 when the handles 30a and 30b are closed) to close the electrical path and permit electrosurgical activation. Further details with respect to various embodiments of the safety switch are described below with respect to FIGS. 18-21D. It is also envisioned that a purely electrical safety switch (See FIG. 23) may be included which allows activation based upon the satisfaction of an electrical condition, e.g., optical alignment of points on the handle 30a (or handles (30a and 30b), magnetic or electromagnetic alignment (or misalignment) to close a switch, proximity sensors, scanners, mercury (or the like) switches, etc. Again, the safety switch 171 may be configured such that one or both switches 250 and/or 260 may be independently and exclusively activatable, i.e., only one switch may be activated at a time.

As can be appreciated, locating the switches 250 and 260 on the housing 20 is advantageous during operating conditions since this positioning reduces the amount of electrical cable in the operating room and eliminates the possibility of activating the wrong instrument or wrong switch during a surgical procedure due to "line-of-sight" activation. An automatic safety circuit or an electro-mechanical or mechanical safety lock (not shown) may be employed which prevents the switches 250 and 260 from energizing the jaw members 110 and 120 in a different mode (i.e. bipolar or monopolar mode) without de-activating a safety circuit or other safety mechanism, i.e., independent and exclusive activation. For example, it may be desirable to configure the switch assembly 70 such that it must be re-set before switching between electrical modes. Re-setting may be accomplished by re-grasping tissue, re-opening the handles 30a and 30b, a reset switch or re-set lever, or other ways customary in the art.

As can be appreciated various switching algorithms (See FIG. 23) may be employed to activate both the bipolar mode for vessel sealing and the monopolar mode for additional tissue treatments (e.g., coagulation, dissection, etc.). It is also envisioned that the safety or lockout mentioned above may be employed as part of an algorithm to either electrically, mechanically or electromechanically "lock out" one electrical mode during activation of the other electrical mode. In addition, it is contemplated that a toggle switch (or the like) may be employed to activate one mode at a time for safety reasons.

Figure 22A:
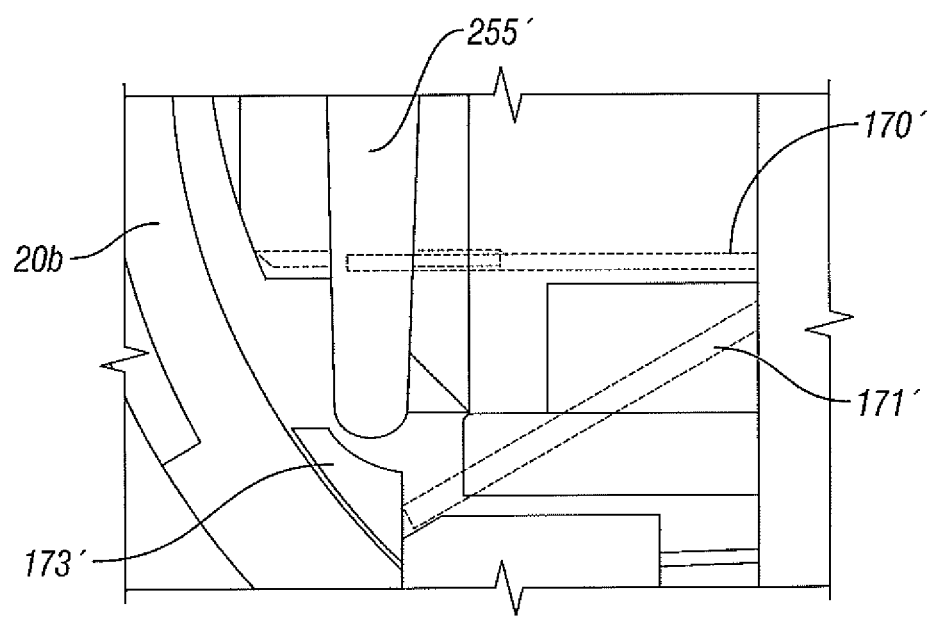
FIG. 22A-22C are internal views showing the operational movements of the safety lockout mechanism of FIG. 18 as the lockout mechanism engages the safety switch of the flex circuit board.
Figure 22B:
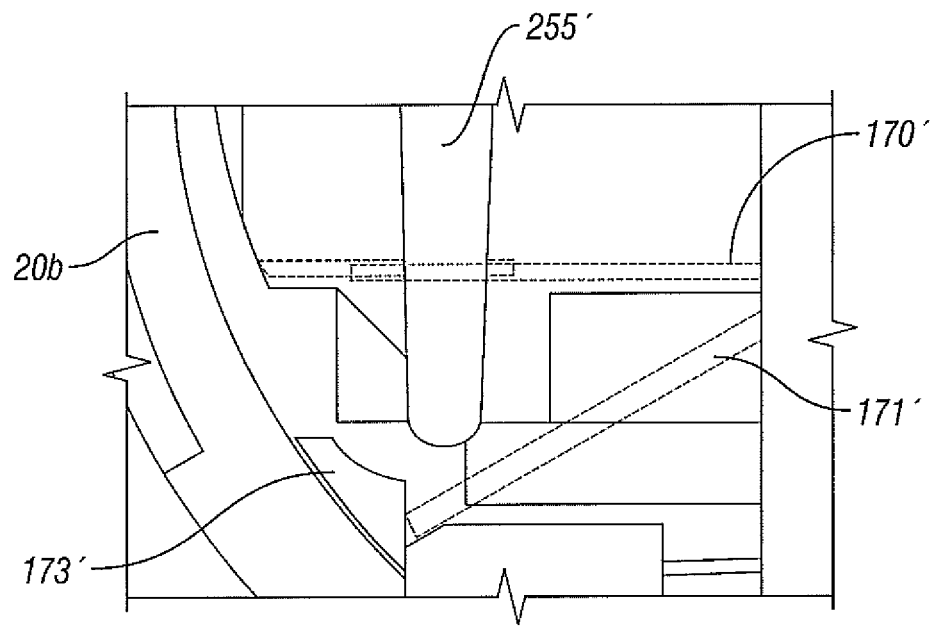

The safety switch 171 when assembled (and when the handles 30a' and 30b and jaws 110 and 120 are opened) is secured against an interior wall or ledge 173 of housing 20b as shown in FIG. 22A. Upon movement of the handle 30a toward housing 20b, safety lockout 255 moves inwardly relative to the housing 20b toward the safety switch 171 as shown in FIG. 22B. As the handles 30a and 30b move toward the closed position (as described in detail above), the safety lockout 255 engages the safety circuit 171' (S3 in FIGS. 19 and 23) to complete circuit and allow selective activation of the forceps 10 (see also FIG. 23).

As best shown in FIGS. 14 and 23-27, the switching assembly may include an intensity control 150 which electromechanically connects to the circuit board 172 and which is configured to allow the user to selectively regulate the intensity of the electrosurgical energy during operating conditions. It is envisioned that the intensity control 150 is particularly configured to regulate the intensity control when the forceps is configured in a monopolar mode. In one particularly useful embodiment, intensity control 150 is elongated and includes a contact 154 which extends transversally therefrom to electro-mechanically interface with the circuit board 172 through the housing 20. An actuating knob 151 extends transversally from the opposite side of the intensity control 150 and is dimensioned to protrude from the side of housing 20 when assembled (see FIGS. 5A, 5B, 6A and 6B). In one particularly useful embodiment, intensity control 150 is configured to slide along housing 20 to regulate the intensity level as desired.

It is envisioned that the intensity control 150 may be configured to slide along the housing 20 in a discrete or continuous manner depending upon a particular purpose. For example and as best shown in FIGS. 24-27, one envisioned intensity control 150' may be dimensioned to include an actuating knob 151' which extends transversally from one side of the intensity control 150' to protrude from housing 20 when assembled. A cantilevered extension 153' having a detent 155' at an end thereof extends generally perpendicularly to the intensity control 150' and is centrally disposed in the intensity control 150'. The detent 155' of the cantilevered extension 153' is dimensioned to engage a corresponding mechanical interface or track 161' disposed within the housing 20 (See FIG. 26). As can be appreciated mechanical advantage is created by the cantilevered extension 153' to facilitate actuation of the detent 155' within the housing 20.

The detent 155' is selectively moveable (by selectively actuating the intensity knob 150') to engage various recesses 163a', 163b', 163c', 163d' and 163e' disposed in the track 161' to lock the intensity control knob 150' at a discrete intensity setting as desired for a particular surgical purpose. It is envisioned that the track 161' may include one or more larger recesses, e.g., recess 163c', to facilitate returning the intensity control 150' to a central (as shown), proximal-most or distal-most position.

The opposing end of the intensity control 150' opposite detent 155' includes a slider bump or other mechanical interface 167' which is operatively engaged atop the flexible circuit board 170 and 170'. The slide bump 167' is configured to deflect the flexible circuit board 170 (or 170') at varying positions as the intensity control 150' is moved. Deflecting the circuit board 170 (or 170') at different locations adjusts the intensity settings by controlling the impedance of the flexible printed circuit 170 or 170' as described below. In other words, the slide bump 167' creates enough depression force to switch the flexible circuit 170 to a different control setting. The switch occurs when one conductive layer on the flexible circuit board 170 flexes to touch another conductive layer to create an electrical connection. As can be appreciated this allows the user to selectively regulate the intensity of the electrosurgical energy during operating conditions. As shown, the forceps 10 includes five (5) different intensity settings.

Figure 27:
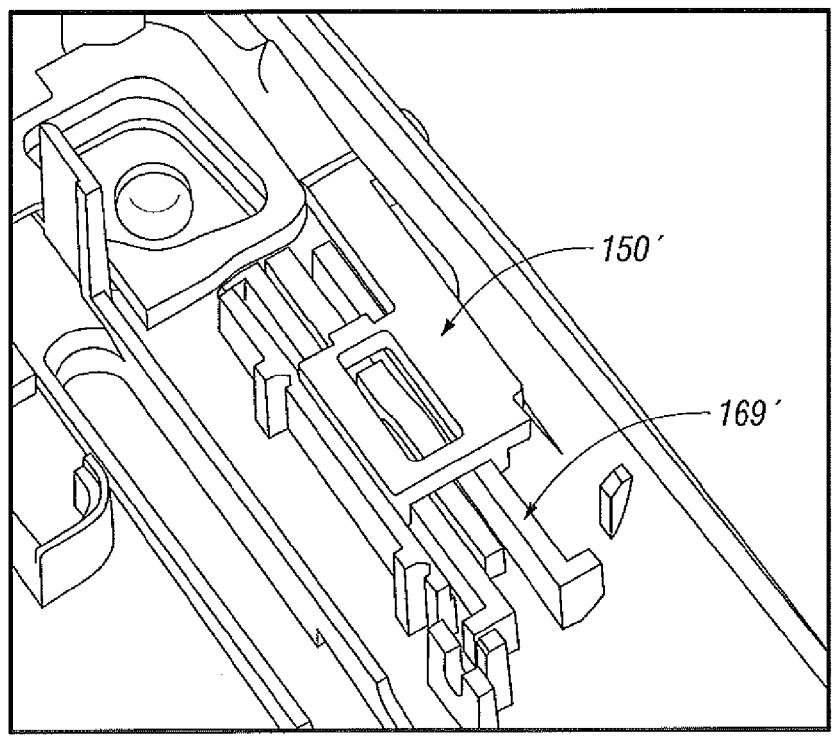
FIG. 27 is a computer-simulated, enlarged internal top view of the intensity control actuator mechanically engaged atop a railway defined in the housing.

As best shown in FIG. 27, the intensity control 150' may be positioned atop a railway 169' defined with the housing 20. The railway 169' is configured to facilitate translational movement of the intensity control 150' from a proximal-most position to a distal-most position atop the flexible circuit 170 (or 170') and within the various recesses 163a'-163e'.

Various types of indicia 155 and/or tactile feedback elements (not shown) may be utilized to denote the position and/or intensity level of the electrical energy, e.g., numbers, graphical indicia, mechanical interfaces, etc. It is also envisioned that the user may configure the initial intensity level on the generator 500 (See FIG. 16) and the intensity control 150 on the forceps 10 may be utilized to increase or decrease the pre-set level by a certain percentage by moving knob 151.

Intensity controller 150 may be configured to function as a slide potentiometer, sliding over and along the flexible or printed circuit board (which may be configured to function as a voltage divider network or "VDN"). For example, the intensity controller 150 may be configured to have a first position wherein knob 151 is disposed at a proximal-most position (e.g., closest to the user) which corresponds to a relative low intensity setting, a second position wherein knob 151 is disposed at a distal-most position (e.g., furthest from the user) corresponding to a relative high intensity setting, and a plurality of intermediate positions wherein knob 151 is disposed at varying positions therebetween corresponding to various intermediate intensity settings. As can be appreciated, the intensity settings from the proximal end to the distal end may be reversed, e.g., high to low. One embodiment of an intensity controller 150 is disclosed in commonly-owned U.S. patent Ser. No. 11/337,990 entitled "ELECTROSURGICAL PENCIL WITH ADVANCED ES CONTROLS", the entire contents of which being incorporated by reference herein.

As illustrated in FIG. 14 and as mentioned above, knob 151 may be dimensioned to ride along a guide channel 157 disposed within housing 20a which is provided with a series of discrete or detented positions defining a series of positions, e.g., five, to allow easy selection of the output intensity from the low intensity setting to the high intensity setting. The series of cooperating discrete or detented positions also provide the surgeon with a degree of tactile feedback. Accordingly, in use, as intensity controller 150 slides distally and proximally, a mechanical interface 158 disposed atop contact 154 selectively engages a series of corresponding detents (not shown) to set the intensity level as well as to provide the user with tactile feedback as to when the intensity controller 150 has been set to the desired intensity setting. Alternatively, audible feedback can be produced from intensity controller 150 (e.g., a "click"), from electrosurgical energy source 500 (e.g., a "tone") and/or from an auxiliary sound-producing device such as a buzzer (not shown).

Intensity controller 150 may also be configured and adapted to adjust the power parameters (e.g., voltage, power and/or current intensity) and/or the power verses impedance curve shape to affect the perceived output intensity. For example, the greater intensity controller 150 is displaced in a distal direction the greater the level of the power parameters transmitted to the jaw members 110 and 120 (or simply jaw member 110 when disposed in a monopolar configuration). When the forceps is disposed in a monopolar mode, current intensities can range from about 60 mA to about 240 mA with tissue having an impedance of about 2 k ohms. An intensity level of 60 mA may provide very light and/or minimal cutting/dissecting/hemostatic effects. An intensity level of 240 mA provides very aggressive cutting/dissecting/hemostatic effects.

Intensity settings are typically preset and selected from a look-up table based on a desired surgical effect, surgical specialty and/or surgeon preference. The selection may be made automatically or selected manually by the user.

It is envisioned that when the forceps 10 is changed from one mode to another mode, the intensity controller 150 may be configured such that it must be reset (e.g., the knob 151 is re-positioned to the proximal-most end of guide channels 157 thus re-setting the intensity level to the preset configuration. After being reset, intensity controller 150 may be adjusted as needed to the desired and/or necessary intensity level for the mode selected.

It is envisioned and contemplated that the circuit board 172 or generator 500 may also include an algorithm which stores the last intensity level setting for each mode. In this manner, intensity controller 150 does not have to be reset to the last operative value when the particular mode is re-selected.

The present disclosure also relates to a method for treating tissue with electrosurgical energy from the electrosurgical generator 500 which includes the steps of: providing an endoscopic forceps 10 including a housing 20 having a shaft 12 affixed thereto. The shaft 12 includes first and second jaw members, 110 and 120, respectively, attached proximate a distal end of the shaft 12. An actuator or handle assembly 30 is included for moving jaw members 110 and 120 relative to one another from a first position wherein the jaw members 110 and 120 are disposed in spaced relation relative to one another to a second position wherein the jaw members 110 and 120 cooperate to grasp tissue therebetween. The switch assembly 170 is included on the housing 20 which permits the user to selectively energize the jaw members 110 and 120 in a monopolar or bipolar mode to treat tissue.

As can be appreciated and as mentioned above, the switch assembly 170 includes switches 250 and 260, printed circuit board 172 and connectors 176a-d. An intensity control 150 may also be included with the switch assembly 170 to regulate the intensity level of the electrosurgical energy when disposed in either mode. In this particular method, the steps further include: grasping tissue between the jaw members 110 and 120; selectively activating the jaw members 110 and 120 to treat tissue disposed between the jaw members 110 and 120 in a bipolar or monopolar fashion; and selectively regulating the intensity of the electrosurgical energy by controlling the intensity control 150.

Other steps of the method may include the steps of: providing a knife assembly 70 which is configured for selective actuation of a knife and the step of selectively actuating the knife assembly 70 to advance the knife 190 to divide tissue after tissue treatment. Still other steps may include: adjusting the intensity of the electrosurgical energy as needed during operating conditions; unlocking the knife assembly 70 prior to actuation or unlocking the knife assembly 70 simultaneously when actuating the handles 30a and 30b from the first and second positions.

As best shown in FIG. 17, the distal end 71a of the elongated knife bar 71 of the knife assembly 70 attaches to the knife 190 at a proximal end thereof. It is envisioned that the knife 190 may be attached to the knife bar 71 in any way known in the art, e.g., snap-fit, fiction-fit, pinned, welded, glued, etc. In the particular embodiment shown in FIG. 17, a clamp collar 197 is used to retain the knife 190 securely engaged with the knife bar 71.

Switches 250 and 260 are typically push-button-type and ergonomically dimensioned to seat within respective apertures 250' and 260' of housing 20 (once assembled). It is envisioned that the switches 250 and 260 permit the user to selectively activate the forceps 10 for surgical treatment of tissue. More particularly, when either switch 250 or 260 is depressed, electrosurgical energy is transferred through leads 325a and/or 325b to respective jaw members 110 and 120.

Again and as noted above, a safety switch 255 (or circuit or algorithm (not shown)) may be employed such that one or both of the switches 250 and 260 cannot fire unless the jaw members 110 and 120 are closed and/or unless the jaw members 110 and 120 have tissue held therebetween. In the latter instance, a sensor (not shown) may be employed to determine if tissue is grasped between jaw members. In addition, other sensor mechanisms may be employed which determine pre-surgical, concurrent surgical (i.e., during surgery) and/or post surgical conditions. These sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 entitled "METHOD AND SYSTEM FOR CONTROLLING OUTPUT OF RF MEDICAL GENERATOR", the entire contents of which being hereby incorporated by reference herein.

Turning back to FIG. 14 which shows the exploded view of the housing 20, rotating assembly 80, drive assembly 70, handle assembly 30 and switch assembly 170, it is envisioned that all of these various component parts along with the shaft 12 and the end effector assembly 100 are assembled during the manufacturing process to form a partially and/or fully disposable forceps 10. For example and as mentioned above, the shaft 12 and/or end effector assembly 100 may be disposable and, therefore, selectively/releasably engagable with the housing 20 and rotating assembly 80 to form a partially disposable forceps 10 and/or the entire forceps 10 may be disposable after use.

It is envisioned that the opposing jaw members 110 and 120 may be rotated and partially opened and closed without unlocking the knife assembly 70 which, as can be appreciated, allows the user to grip and manipulate the tissue without premature activation of the knife 190. As mentioned below, only a substantially fully closed position of the handles 30a and 30b will unlock the knife assembly 70 for actuation.

Once the desired position for the sealing site is determined and the jaw members 110 and 120 are properly positioned, handles 30a and 30b may be squeezed to actuate the drive assembly 60 to close the jaw members 110 and 120 about tissue. As mentioned above, when the handles 30a and 30b are fully closed about tissue the toggle links 35a and 35b over-rotate past parallel with the longitudinal axis "A" such that slightly releasing the handles 30a and 30b biases the spring 63 to lock the handles 30a and 30b relative to one another. As can be appreciated, when the handles 30a and 30b lock relative to one another, the jaw members 110 and 120, in turn, lock and secure about tissue within a pressure range of about 3 kg/cm$^2$ to about 16 kg/cm$^2$ and, preferably, with a pressure range of about 7 kg/cm$^2$ to about 13 kg/cm$^2$. The forceps 10 is now ready for selective application of electrosurgical energy and subsequent separation of the tissue (if desired).

It is envisioned that the combination of the mechanical advantage gained by the disposition of the toggle links 35a and 35b relative to the longitudinal axis "A" along with the mechanical advantage gained by configuring the distal ends 34a' and 34b' as inter-engaging gear teeth will facilitate and assure consistent, uniform and accurate closure pressure about the tissue within the desired working pressure range of about 3 kg/cm$^2$ to about 16 kg/cm$^2$ and, in one particularly useful embodiment, about 7 kg/cm$^2$ to about 13 kg/cm$^2$. By controlling the intensity, frequency and duration of the electrosurgical energy applied to the tissue, the user can either cauterize, coagulate/desiccate, seal and/or simply reduce or slow bleeding by activating either or both switches 250 and 260.

In one or more particularly useful embodiments, the electrically conductive sealing surfaces 112, 122 of the jaw members 110, 120, respectively, are relatively flat to avoid current concentrations at sharp edges and to avoid arcing between high points. In addition and due to the reaction force of the tissue when engaged, jaw members 110 and 120 are preferably manufactured to resist bending. For example, the jaw members 110 and 120 may be tapered along the width thereof which is advantageous since the thicker proximal portion of the jaw members 110 and 120 will resist bending due to the reaction force of the tissue.

As mentioned above, at least one jaw member, e.g., 120, may include one or more stop members 90 which limit the movement of the two opposing jaw members 110 and 120 relative to one another. The stop member(s) 90 may be dimensioned to extend from the sealing surface 122 a predetermined distance according to the specific material properties (e.g., compressive strength, thermal expansion, etc.) to yield a consistent and accurate gap distance "G" during sealing. The gap distance between opposing sealing surfaces 112 and 122 during sealing ranges from about 0.001 inches to about 0.006 inches and, in one particularly useful embodiment, between about 0.002 and about 0.003 inches. The non-conductive stop member(s) 90 may be molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material (or the like) onto the surfaces of one or both jaw members 110 and 120 to form the stop member(s) 90. Several thermal spraying techniques are contemplated which involve depositing a broad range of heat resistant and insulative materials on various surfaces to create stop members 90 for controlling the gap distance between electrically conductive surfaces 112 and 122.

As energy is being selectively transferred to the end effector assembly 100, across the jaw members 110 and 120 and through the tissue, a tissue seal forms isolating two tissue halves. At this point and with other known vessel sealing instruments, the user must remove and replace the forceps 10 with a cutting instrument (not shown) to divide the tissue halves along the tissue seal. As can be appreciated, this is both time consuming and tedious and may result in inaccurate tissue division across the tissue seal due to misalignment or misplacement of the cutting instrument along the ideal tissue cutting plane.

As explained in detail above, the present disclosure incorporates knife assembly 70 which, when activated via the trigger knob 76, progressively and selectively divides the tissue along an ideal tissue plane in precise manner to effectively and reliably divide the tissue into two sealed halves with a tissue gap therebetween. The knife assembly 70 allows the user to quickly separate the tissue immediately after sealing without substituting a cutting instrument through a cannula or trocar port. As can be appreciated, accurate sealing and dividing of tissue is accomplished with the same forceps 10.

It is envisioned that knife blade 190 may also be coupled to the same or an alternative electrosurgical energy source to facilitate separation of the tissue along the tissue seal. Moreover, it is envisioned that the angle of the knife blade tip 192 may be dimensioned to provide more or less aggressive cutting angles depending upon a particular purpose. For example, the knife blade tip 192 may be positioned at an angle which reduces "tissue wisps" associated with cutting. Moreover, the knife blade tip 192 may be designed having different blade geometries such as serrated, notched, perforated, hollow, concave, convex etc. depending upon a particular purpose or to achieve a particular result. It is also contemplated that the forceps 10 may be activated in a monopolar mode to divide tissue after formation of a tissue seal.

Once the tissue is divided into tissue halves, the jaw members 110 and 120 may be opened by re-grasping the handles 30a and 30b moving each handle 30a and 30b outwardly relative to the housing 20. It is envisioned that the knife assembly 70 generally cuts in a progressive, uni-directional fashion (i.e., distally).

Figure 3A:
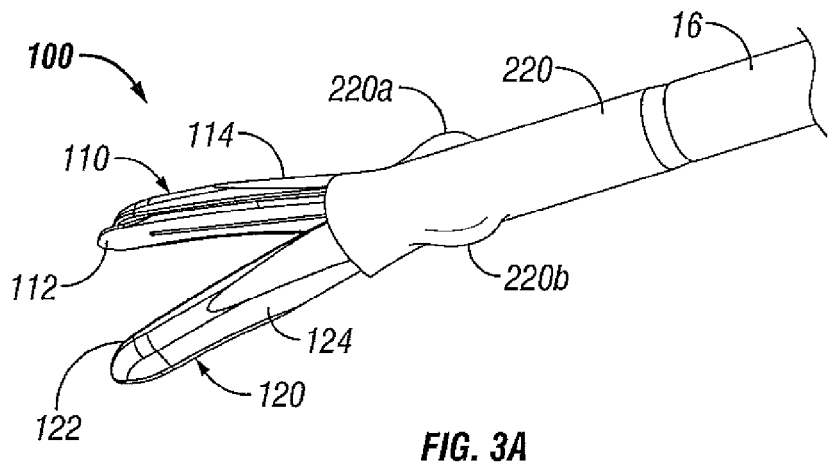
FIG. 3A is an enlarged left, perspective view of the end effector assembly of FIG. 1A.
Figure 3B:
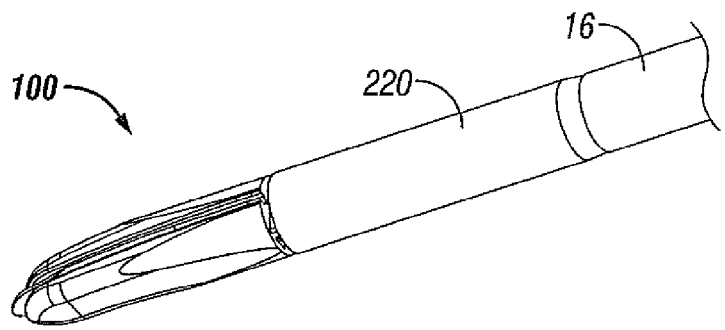
FIG. 3B is an enlarged left, perspective view of the end effector assembly of FIG. 1B.
Figure 3C:
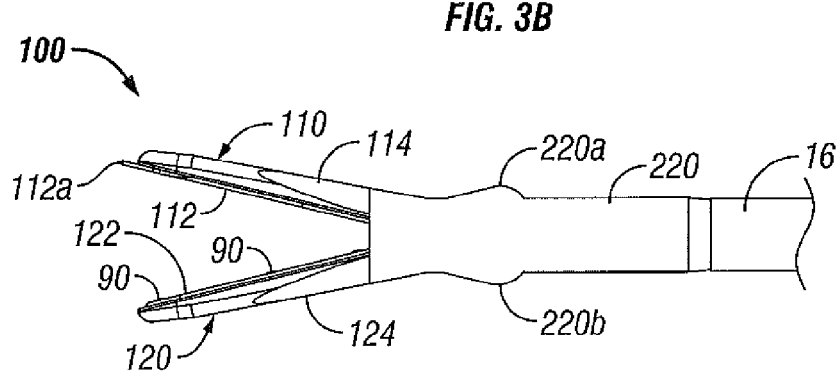
FIG. 3C is an enlarged side view of the end effector assembly of FIG. 1A.
Figure 3D:
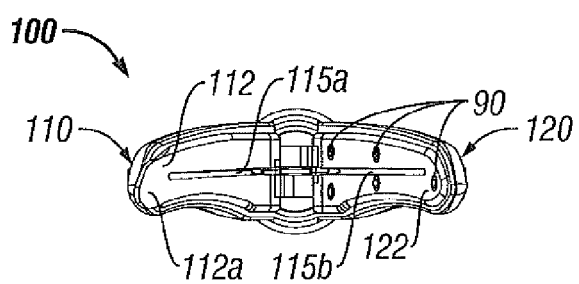
FIG. 3D is an enlarged end view of the end effector assembly of FIG. 1A.
Figure 4:
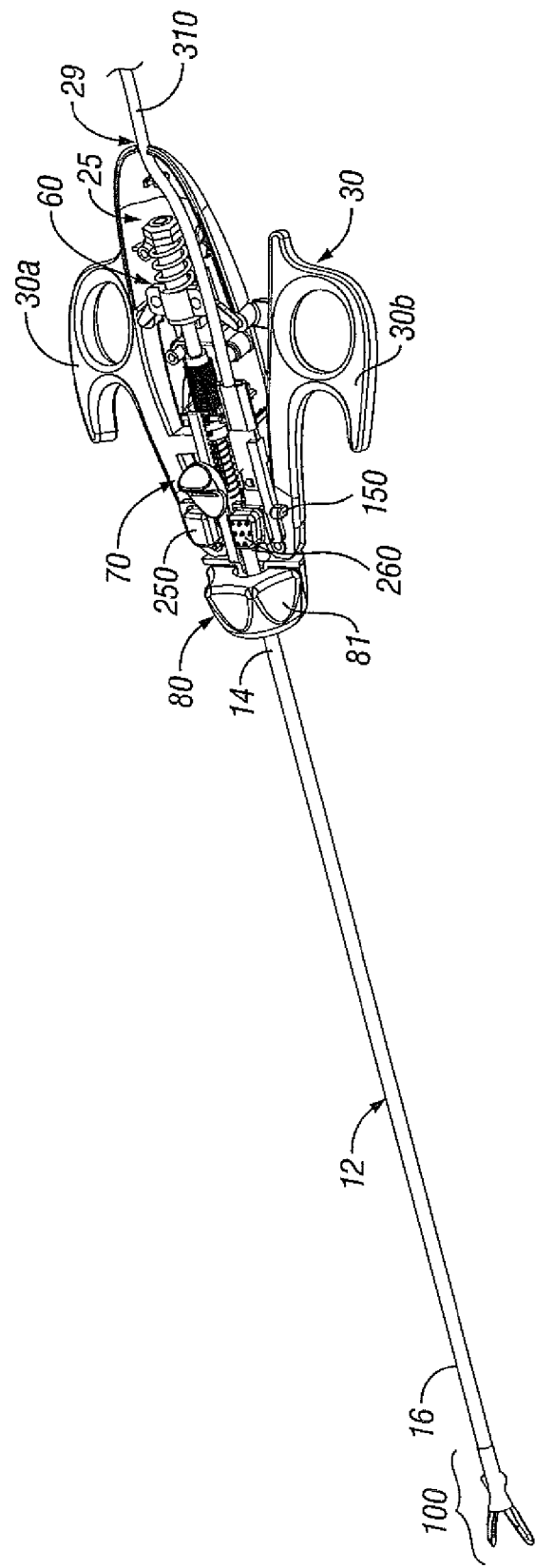
FIG. 4 is a top, internal perspective view of the forceps of FIG. 1A shown without a housing cover.

As best shown in FIGS. 3A-3C, the proximal portions of the jaw members 110 and 120 and the distal end 16 of shaft 12 may be covered by a resilient or flexible insulating material or boot 220 to reduce stray current concentrations during electrosurgical activation especially in the monopolar activation mode. More particularly, the boot 220 is flexible from a first configuration (See FIG. 3B) when the jaw members 110 and 120 are disposed in a closed orientation to a second expanded configuration (See FIGS. 3A and 3C) when the jaw members 110 and 120 are opened. As can be appreciated, when the jaw members 110 and 120 open, the boot flexes or expands at areas 220a and 220b to accommodate the movement of the proximal flanges 113 and 123. Further details relating to one envisioned insulating boot 220 are described with respect to commonly-owned and concurrently-filed U.S. Application Provisional Application Ser. No. 60/722,213 entitled "INSULATING BOOT FOR ELECTROSURGICAL FORCEPS", the entire contents of which being incorporated by reference herein.

FIGS. 18-22C show one particularly useful embodiment of a safety lockout mechanism 255' for use with a flex circuit 170'. Much like the above described safety lockout 255, lockout mechanism 255' is disposed on handle 30a' at a point distal to trigger lockout 32'. This particular safety lockout 255' is configured to extend normally to the longitudinal axis "A" as shown best in FIG. 18. Movement of handle 30a' towards housing 20 causes the safety lockout 255' to move towards the housing 20 in a similar manner as described above. Safety lockout 255' is configured to engage a safety switch 171' of the flex circuit 170' to allow activation only when handle 30a' (and, in turn, jaw members 110 and 120) is moved relative to housing 20 (i.e., both handles 30a' and 30b are closed to grasp tissue).

Figure 20:
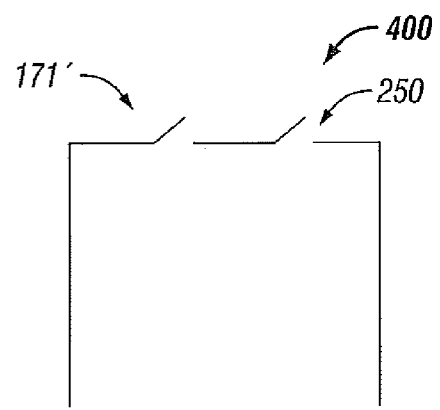
FIG. 20 is a schematic diagram showing the operational features of a safety switch of the flex circuit board of FIG. 19.
Figure 21:
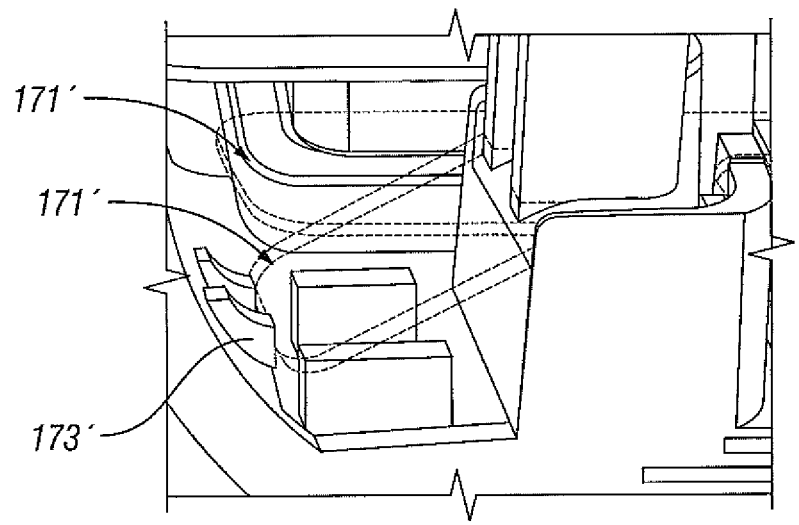
FIG. 21 is an internal perspective view showing the assembly of the safety switch of FIG. 19 in the housing of the forceps.

As best shown in schematic illustration of FIG. 20, safety switch 171' is designed as part of a circuit 400 such that circuit 400 remains open until the safety switch 171' is activated. FIG. 21 shows the position of safety switch 171' prior to and after assembly. More particularly, upon assembly, the safety switch 171' is flexed into position (see phantom representation) by the top portion 20a of housing 20 such that the distal portion of the safety switch 171' is biased and wedged against an interior wall or ledge 173' disposed within housing 20b. It is envisioned that the safety switch 171' will remain secured in place for the useful life of the forceps 10.

Figure 22C:
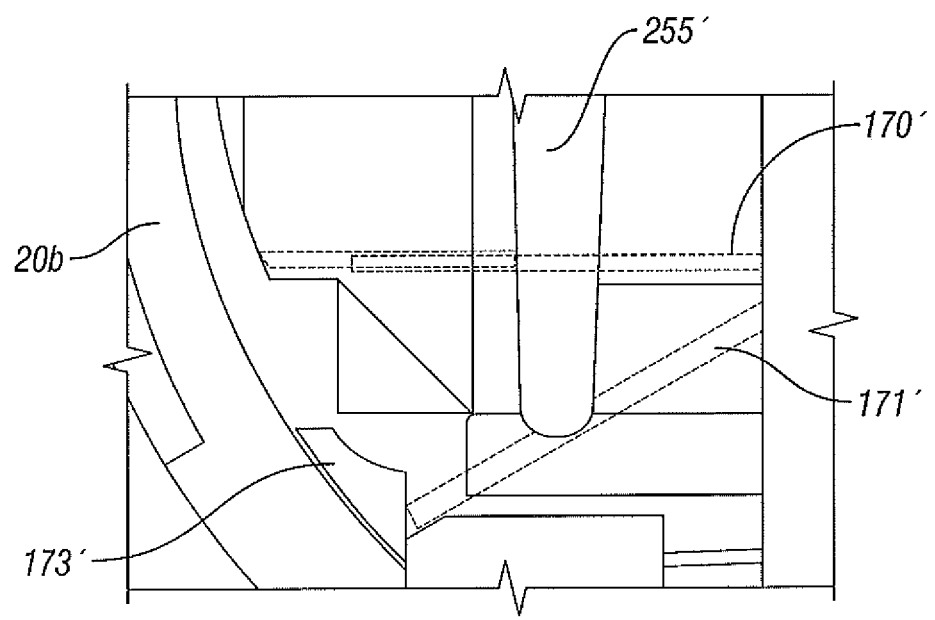

FIGS. 22A-22C show the activation sequence of the safety switch 171'. More particularly and as mentioned above, the safety switch 171' when assembled (and when the handles 30a' and 30b and jaws 110 and 120 are opened) is secured against an interior wall or ledge 173' of housing 20b as shown in FIG. 22A. Upon movement of the handle 30a' toward housing 20b, safety lockout 255' moves inwardly relative to the housing 20b toward the safety switch 171' as shown in FIG. 22B. As the handles 30a' and 30b move toward the closed position (as described in detail above), the safety lockout 255' engages the safety circuit 171' to complete circuit 400 and allow selective activation of the forceps 10.

It is envisioned that the safety switch 171' may be configured to allow both bipolar and monopolar activation once closed or configured in a more restrictive fashion, e.g., only permit one type of electrical activation at a time without re-setting the safety switch 171' (i.e., opening and re-grasping the handles 30*a*' and 30*b*, a separate toggle switch (not shown), etc.). Moreover, it is also envisioned that the safety switch 171' may be configured to simply safeguard against the activation of one of the modes (i.e., the monopolar mode) depending upon a particular purpose and the other mode (i.e., the bipolar mode) is not restricted by the safety switch 171'.

From the foregoing and with reference to the various figure drawings, those skilled in the art will appreciate that certain modifications can also be made to the present disclosure without departing from the scope of the same. For example, it may be preferable to add other features to the forceps 10, e.g., an articulating assembly to axially displace the end effector assembly 100 relative to the elongated shaft 12.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120. Examples of such sensor systems are described in commonly-owned U.S. patent application Ser. No. 10/427,832 entitled "METHOD AND SYSTEM FOR CONTROLLING OUTPUT OF RF MEDICAL GENERATOR", the entire contents of which being incorporated by reference herein.

Moreover, it is contemplated that the knife assembly 70 may include other types of recoil mechanisms which are designed to accomplish the same purpose, e.g., gas-actuated recoil, electrically-actuated recoil (i.e., solenoid), etc. It is also envisioned that the forceps 10 may be used to cut tissue without sealing. Alternatively, the knife assembly 70 may be coupled to the same or alternate electrosurgical energy source to facilitate cutting of the tissue.

Although the figures depict the forceps 10 manipulating an isolated vessel, it is contemplated that the forceps 10 may be used with non-isolated vessels as well. Other cutting mechanisms are also contemplated to cut tissue along the ideal tissue plane.

It is envisioned that the outer surface of the end effector assembly 100 may include a nickel-based material, coating, stamping, metal injection molding which is designed to reduce adhesion between the jaw members 110 and 120 with the surrounding tissue during activation and sealing. Moreover, it is also contemplated that the conductive surfaces 112 and 122 of the jaw members 110 and 120 may be manufactured from one (or a combination of one or more) of the following materials: nickel-chrome, chromium nitride, Med-Coat 2000 manufactured by The Electrolizing Corporation of OHIO, Inconel 600 and tin-nickel. The tissue conductive surfaces 112 and 122 may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 122 made from or coated with Ni200, Ni201 (~100% Ni) also showed improved non-stick performance over typical bipolar stainless steel electrodes.

Figure 18:
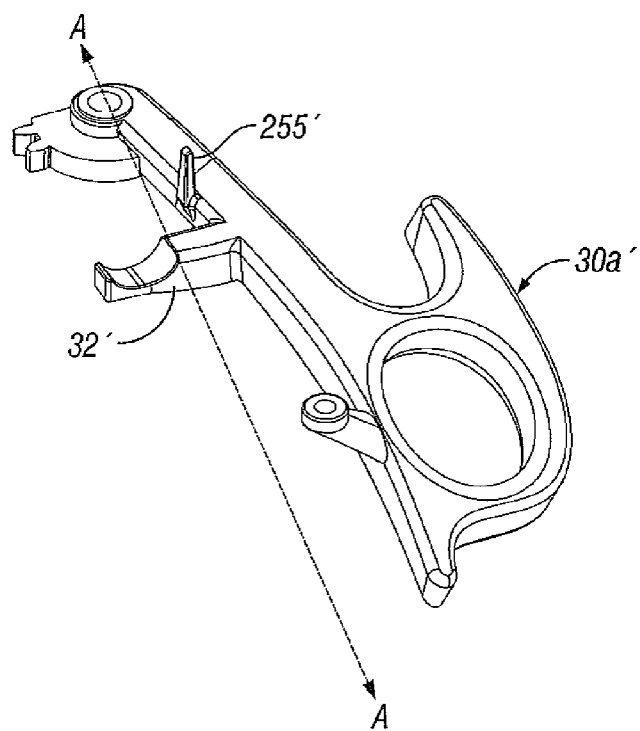
FIG. 18 is a top, perspective view of an alternate safety lockout mechanism for use with the forceps of FIG. 1A.
Figure 19:
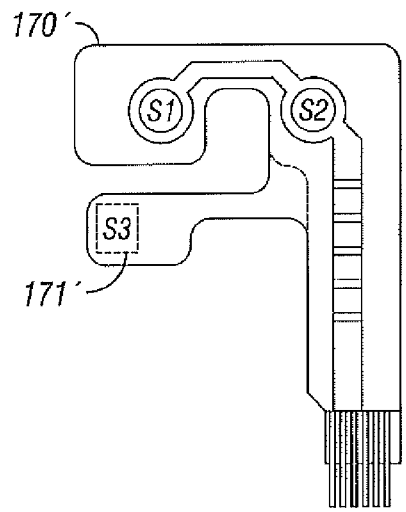
FIG. 19 is a top view of a flex circuit board for use with the forceps of FIG. 1A.

While the drawings show one particular type of monopolar lockout or safety mechanism 255 for use with the presently disclosed forceps, FIGS. 18 and 19 show an alternative safety lockout mechanism which may be employed with the forceps 10.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An endoscopic forceps, comprising:
a housing having a shaft attached thereto, the shaft including a pair of jaw members disposed at a distal end thereof;
a drive assembly disposed in the housing operable to move the jaw members relative to one another from a first position, wherein the jaw members are disposed in spaced relation relative to one another, to a second position, wherein the jaw members are closer to one another, for manipulating tissue;
a pair of handles operatively connected to the drive assembly, the handles movable relative to the housing to actuate the drive assembly to move the jaw members;
each jaw member adapted to connect to a source of electrical energy such that the jaw members are capable of conducting energy for treating tissue; and
a switch disposed on the housing and activatable to selectively deliver energy of a first electrical potential to at least one jaw member for treating tissue, the switch operatively coupled to an intensity control mechanism disposed within the housing that is selectively adjustable to regulate the level of electrosurgical energy to at least one jaw member, wherein the intensity control mechanism includes a slide bump configured to deflect a flexible circuit board to regulate the level of electrosurgical energy to at least one jaw member.

2. An endoscopic forceps according to claim 1, wherein the intensity control mechanism is selectively adjustable in discrete increments.

3. An endoscopic forceps according to claim 1, wherein the intensity control mechanism includes a first mechanical interface configured to engage a series of corresponding mechanical interfaces defined in the housing to regulate the level of electrosurgical energy in discrete increments.

4. An endoscopic forceps according to claim 3, wherein the first mechanical interface includes a detent and the corresponding mechanical interfaces defined within the housing include recesses.

5. An endoscopic forceps according to claim 4, wherein the intensity control mechanism includes a second mechanical interface that cooperates with the detent to mechanically engage a circuit board disposed within the housing at discrete locations when the detent engages a corresponding one of the series of recesses.

6. An endoscopic forceps according to claim 4, wherein the detent is disposed in a cantilevered fashion atop the intensity control mechanism.

7. An endoscopic forceps according to claim 1, wherein the intensity control is positioned atop a railway defined within the housing.

* * * * *